United States Patent
Clauson et al.

(10) Patent No.: US 11,737,681 B2
(45) Date of Patent: *Aug. 29, 2023

(54) METAL DETECTION DEVICE AND METHODS OF OPERATION THEREOF

(71) Applicant: Melzi Corporation, Reno, NV (US)

(72) Inventors: Luke W. Clauson, Reno, NV (US); Matthew Byrnes Newell, Reno, NV (US); Nicholas G. Lewis, Sparks, NV (US); Michael A. Raye, Reno, NV (US); Jesse D. Adams, Mars, PA (US); Samuel A. Weprin, Richmond, VA (US)

(73) Assignee: Melzi Corporation, Reno, NV (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/649,779

(22) Filed: Feb. 2, 2022

(65) Prior Publication Data

US 2022/0151507 A1 May 19, 2022

Related U.S. Application Data

(63) Continuation of application No. 16/950,119, filed on Nov. 17, 2020, now Pat. No. 11,272,857, which is a
(Continued)

(51) Int. Cl.
*A61B 5/00* (2006.01)
*A61B 5/06* (2006.01)
(Continued)

(52) U.S. Cl.
CPC .............. *A61B 5/064* (2013.01); *A61B 34/20* (2016.02); *A61B 90/98* (2016.02); *A61B 2034/2051* (2016.02)

(58) Field of Classification Search
CPC ......... A61B 34/20; A61B 5/064; A61B 90/98; A61B 2034/2051
See application file for complete search history.

(56) References Cited

U.S. PATENT DOCUMENTS

| | | |
|---|---|---|
| 4,913,152 A | 4/1990 | Ko et al. |
| 5,436,440 A | 7/1995 | Barkan |
| (Continued) | | |

FOREIGN PATENT DOCUMENTS

| | | |
|---|---|---|
| WO | WO 2008/131391 | 10/2008 |
| WO | WO 2021/050174 | 3/2021 |

OTHER PUBLICATIONS

Cima, Robert R., et al. "Using a data-matrix-coded sponge counting system across a surgical practice: impact after 18 months." The Joint Commission Journal on Quality and Patient Safety, vol. 37, No. 2, pp. 51-AP3, Feb. 2011.
(Continued)

*Primary Examiner* — Rajeev P Siripurapu
(74) *Attorney, Agent, or Firm* — Levine Bagade Han LLP

(57) ABSTRACT

Disclosed are methods and devices for detecting retained surgical items or other objects having a magnetic signature within a corpus of a patient. The device can comprise a handle, a shaft extending from the handle, and a distal sensing portion positioned distally of the shaft. The distal sensing portion can comprise one or more gradiometers comprising a plurality of magnetometers. The device can further comprise one or more output components configured to generate a user output to alert a user of a detected object.

3 Claims, 24 Drawing Sheets

Related U.S. Application Data continuation of application No. 16/983,793, filed on Aug. 3, 2020, now Pat. No. 10,881,323, which is a continuation of application No. PCT/US2020/044649, filed on Jul. 31, 2020.

(60) Provisional application No. 62/927,702, filed on Oct. 30, 2019, provisional application No. 62/900,385, filed on Sep. 13, 2019.

(51) Int. Cl.
*A61B 90/98* (2016.01)
*A61B 34/20* (2016.01)

(56) References Cited

U.S. PATENT DOCUMENTS

| | | |
|---|---|---|
| 6,268,725 B1 | 7/2001 | Vernon et al. |
| D490,002 S | 5/2004 | Sanchez |
| D496,292 S | 9/2004 | Sowers |
| 6,819,109 B2 | 11/2004 | Sowers et al. |
| D614,981 S | 5/2010 | Junes |
| D624,445 S | 9/2010 | Heckhausen |
| D774,404 S | 12/2016 | Piro |
| 10,188,310 B2 | 1/2019 | Derichs et al. |
| 10,342,623 B2 | 7/2019 | Huelman et al. |
| 10,881,323 B1 | 1/2021 | Clauson et al. |
| 2007/0052411 A1 | 3/2007 | McClure et al. |
| 2010/0168270 A1 | 7/2010 | Guo et al. |
| 2013/0066136 A1 | 3/2013 | Palese et al. |
| 2013/0082816 A1 | 4/2013 | Pusateri et al. |
| 2013/0158655 A1 | 6/2013 | Sutton et al. |
| 2015/0141806 A1 | 5/2015 | Smith et al. |
| 2016/0262844 A1 | 9/2016 | Cohen et al. |
| 2017/0020392 A1 | 1/2017 | Xu |
| 2017/0347915 A1 | 12/2017 | Weprin et al. |
| 2019/0150779 A1 | 5/2019 | Derichs et al. |
| 2019/0192044 A1 | 6/2019 | Ravi et al. |
| 2019/0205001 A1 | 7/2019 | Messerly et al. |
| 2021/0076976 A1 | 3/2021 | Clauson et al. |

OTHER PUBLICATIONS

Jayadevan, Rajiv et al. "A protocol to recover needles lost during minimally invasive surgery." JSLS : Journal of the Society of Laparoendoscopic Surgeons vol. 18, issue 4, Oct.-Dec. 2014.

Kim, et al., "Development of a SQUID-Based 3He Co-Magnetometer Readout for a Neutron Electric Dipole Moment Experiment", IEEE Transactions on Applied Superconductivity, vol. 23, No. 3, Jun. 2013.

METAL DETECTION DEVICE AND METHODS OF OPERATION THEREOF

CROSS-REFERENCE TO RELATED APPLICATIONS

This application is a continuation of U.S. patent application Ser. No. 16/950,119 filed on Nov. 17, 20209, which is a continuation of U.S. patent application Ser. No. 16/983,793 filed on Aug. 3, 2020 (now U.S. Pat. No. 10,881,323 issued Jan. 5, 2021), which is a continuation of PCT Application No. PCT/US2020/044649 filed on Jul. 31, 2020, which claims the benefit of U.S. Provisional Application No. 62/900,385 filed on Sep. 13, 2019 and U.S. Provisional Application No. 62/927,702 filed on Oct. 30, 2019, the entireties of which are incorporated herein by reference. This application also incorporates by reference U.S. Patent Publication No. US 2017/0347915 A1, published on Dec. 7, 2017.

TECHNICAL FIELD

The present disclosure relates generally to the field of magnetometer-based metal detection, and, more specifically, to an improved magnetometer-based metal detector for detecting retained surgical items such as sharps or RFID-tagged sponges, metallic implants, metallic wires, and other objects having a magnetic signature within a corpus of a patient.

BACKGROUND

Surgeons and other operating room (OR) professionals spend a significant amount of time and resources locating retained surgical items (RSIs) such as lost surgical needles, broken parts of surgical instruments, or other types of sharps in their patients. The growth of minimally invasive laparoscopic and robotic procedures have made it harder for surgeons to find lost needles, broken instruments, and other types of sharps and fragments. Retained objects can cause serious harm to patients including potential chronic pain or organ injury. As a result, surgeons and other OR professionals go to great lengths to ensure all tools and instruments are accounted for. However, when dealing with an average of 300 tools per surgery, multiple rotations of staff, and parts of instruments breaking off, searching for RSIs have become more common. According to one study, 63.8% of all surgeons surveyed experienced a lost needle event during minimally invasive surgery within the last 12 months. Moreover, 89.6% of surgeons surveyed reported one to five needle loss incidents during their careers. Furthermore, over 13% of events required more than 30 minutes to locate and recover the lost needle and in 3% of cases, surgeons were unable to recover such needles after conducting a search. See Jayadevan, Rajiv et al. "A protocol to recover needles lost during minimally invasive surgery." JSLS: Journal of the Society of Laparoendoscopic Surgeons vol. 18,4 (2014).

Surgeons and other OR professionals often rely initially on a visual search for any metallic RSIs such as needles, sharps, and broken tools. If the item is not found, patients typically receive an X-ray scan and more anesthesia as OR staff spend more time searching. This results in greater exposure to radiation for patients and staff and an increased risk of complications from prolonged anesthesia time. When surgeons cannot ultimately locate the lost needle or sharp, patient disclosure is required and both hospitals and surgeons are at risk of reputational damage or litigation. In addition, RSI events are not reimbursable, leaving hospitals to absorb the costs of any further procedures or settlements.

Traditional metal detection devices often lack the ability to determine, with high precision, the exact location of a metallic RSI within a body of a patient. Moreover, such devices are often not suitable for in vivo detection, not portable, and cannot be easily rotated to allow for navigation through tortuous anatomy. Moreover, such traditional metal detection devices cannot properly remove the effects of background magnetic field interferences or can only remove such interferences through rudimentary single point measurements or subtraction algorithms that may result in inaccurate detection.

Therefore, a solution is needed which addresses the above shortcomings and disadvantages. Such a solution should be portable and allow a surgeon to easily move and rotate the device within the body of a patient. Such a solution should also not be overly complicated and be cost-effective and easy to manufacture.

SUMMARY

Disclosed are magnetometer-based metal detectors, metal detection systems, and methods of operation thereof for detecting metallic objects (e.g., RSIs, metallic implants, metallic wires, etc.) within a corpus of a patient. In one aspect, a metal detection device is disclosed comprising a handle, a shaft extending from the handle, and a distal sensing portion positioned distally of the shaft. The distal sensing portion can comprise a proximal gradiometer comprising a first proximal magnetometer and a second proximal magnetometer, and a distal gradiometer comprising a first distal magnetometer and a second distal magnetometer. The metal detection device can also comprise an output component configured to generate a user output to alert a user of a detected object and a microcontroller comprising one or more processors and memory units. The one or more processors can be programmed to execute instructions stored in the memory units to calculate a differential signal from magnetic field measurements obtained from the first proximal magnetometer, the second proximal magnetometer, the first distal magnetometer, and the second distal magnetometer. The one or more processors can be programmed to execute further instructions to apply at least one of a signal filter and a derivative to the differential signal calculated to obtain a detection signal.

The signal filter can comprise a high-pass filter and a low-pass filter (e.g., a second order or two-pole filter). For example, the high-pass filter can get rid of drift and offset and bring the average signal back to zero. The low-pass filter or second order filter (also known as a two-pole filter) can more aggressively cut off high-frequency noise. For example, the high-pass filter can have a cutoff of 5.5 Hz and the low-pass filter can have a cutoff of 10 Hz.

The one or more processors can be programmed to execute further instructions to compare the detection signal against a threshold and instruct the output component to generate the user output when the detection signal exceeds the threshold.

Additionally, in another mode, the threshold can be removed or set below zero in order to render it un-used for a given level or for a given period of time or for a given product such that the sound or tone is always on and the tone and or light can chance frequency and/or intensity as the signal grows and shrinks. This mode could allow for signals below a threshold to be observed for response.

The first proximal magnetometer, the second proximal magnetometer, the first distal magnetometer, and the second distal magnetometer can be two-axis magnetometers. The first proximal magnetometer, the second proximal magnetometer, the first distal magnetometer, and the second distal magnetometer can each have an x-axis and a y-axis. The first proximal magnetometer and the second proximal magnetometer can each comprise at least a +x-axis and a +y-axis. The +x-axis of the first proximal magnetometer can be oriented opposite the +x-axis of the second proximal magnetometer. The +y-axis of the first proximal magnetometer can be oriented opposite the +y-axis of the second proximal magnetometer.

The first distal magnetometer and the second distal magnetometer can each comprise at least a +x-axis and a +y-axis. The +x-axis of the first distal magnetometer can be oriented opposite the +x-axis of the second distal magnetometer. The +y-axis of the first distal magnetometer can be oriented opposite the +y-axis of the second distal magnetometer.

The second distal magnetometer and the first proximal magnetometer can each comprise at least a +x-axis and a +y-axis. The +x-axis of the second distal magnetometer can be oriented opposite the +x-axis of the first proximal magnetometer. The +y-axis of the second distal magnetometer can be oriented opposite the +y-axis of the first proximal magnetometer.

In some variations, axes of the first proximal magnetometer and the second proximal magnetometer can be either aligned or orthogonal to axes of the first distal magnetometer and the second distal magnetometer.

Although reference is made to each of the magnetometers or magnetic sensors comprising an x-axis (e.g., +x-axis) and a y-axis (e.g., +y-axis), it is contemplated by this disclosure that any reference to a x-axis (e.g., +x-axis) or a y-axis (e.g., +y-axis) can also refer to a single-axis magnetometer where the magnetometer or magnetic sensor only has an x-axis or y-axis. Therefore, any references to four two-axis magnetometers can also be applied to eight one-axis magnetometers.

In other variations, at least one of the axes of the first proximal magnetometer and the second proximal magnetometer can be not orthogonal to (or oriented at an oblique angle with respect to) at least one of the axes of the first distal magnetometer and the second distal magnetometer. For example, the distal sensing portion can comprise a proximal rigid printed circuit board (PCB), a distal rigid PCB, and a distal flexible circuit disposed in between the proximal rigid PCB and the distal rigid PCB and connecting the proximal rigid PCB to the distal rigid PCB. The first proximal magnetometer and the second proximal magnetometer can be coupled to the proximal rigid PCB. The first distal magnetometer and the second distal magnetometer can be coupled to the distal rigid PCB. The distal rigid PCB can be angularly rotated with respect to the proximal rigid PCB about the distal flexible circuit by a twist angle. In some variations, the twist angle can be about 45 degrees. In other variations, the twist angle can be about 60 degrees or about 30 degrees.

The distal sensing portion can be covered by a sensor housing. The sensor housing can have a housing diameter. The housing diameter can be between about 3.0 mm to about 10.0 mm. For example, the housing diameter can be about 5.0 mm. The sensor housing can also have a housing length dimension between about 40.0 mm to 50.0 mm.

In some variations, the microcontroller can be housed within the handle. The distal sensing portion can further comprise one or more operational amplifiers. The one or more operational amplifiers can be configured to amplify raw output signals from the at least one of the first proximal magnetometer, the second proximal magnetometer, the first distal magnetometer, and the second distal magnetometer before such signals are transmitted to an analog-to-digital converter (ADC) or an ADC component of the microcontroller within the handle.

The metal detection device can also comprise a flexible portion coupling or connecting the distal sensing portion to the shaft. The flexible portion can be bendable and comprise a straightened configuration and a bent configuration. The distal sensing portion can be positioned closer to the shaft when the flexible portion is in the bent configuration. The flexible portion can be made in part of a thermoplastic elastomer. For example, the flexible portion can be made in part of Pebax®.

The handle can further comprise a trigger configured to control bending of the flexible portion. The trigger can be connected to the flexible portion by a pull cable extending through the shaft and the flexible portion. Squeezing the trigger can pull the pull cable to bend the flexible portion toward the shaft.

The handle can further comprise a trigger potentiometer coupled to the trigger. The one or more processors of the microcontroller can be programmed to execute instructions to determine a trigger speed based on data obtained from the trigger potentiometer.

The shaft can be rotatable with respect to a longitudinal axis of the shaft. The handle can also comprise a clocking ring coupled to the shaft. The shaft can be rotatable in response to a rotation of the clocking ring.

The handle can further comprise a locking ring. The locking ring can comprise a plurality of locking splines configured to obstruct the clocking ring from rotating. The clocking ring can be configured to be pushed in a distal direction to free the clocking ring from the locking splines of the locking ring. The clocking ring can be rotatable after being pushed in the distal direction.

The metal detection device can also comprise a test rod configured to translate into and retract out of a sensor housing covering the distal sensing portion. The test rod can be used to verify a functionality of the metal detection device. In some variations, the test rod can be made in part of a ferromagnetic metal.

The test rod can be partially housed within a spring tube. The spring tube can extend through the shaft and a flexible portion coupling the shaft to the distal sensing portion. The flexible portion can be bendable such that a flexible portion distal end bends toward the shaft when a trigger on the handle is squeezed. The spring tube can be configured to bias the flexible portion back to an unbent configuration when the trigger is released.

The spring tube can be made in part of a thermoplastic. For example, the spring tube can be made in part of polyethylene terephthalate.

The handle can further comprise a test rod slider. The test rod slider can be configured to be actuated distally or proximally to translate the test rod axially within the shaft. The handle can also comprise a slider potentiometer coupled via gears to part of the test rod slider. The one or more processors of the microcontroller can be programmed to execute further instructions to determine a slider position based on data obtained from the slider potentiometer. The slider position can be indicative of a relative positioning of the test rod with respect to at least one of the first proximal magnetometer, the second proximal magnetometer, the first distal magnetometer, and the second distal magnetometer.

The one or more processors of the microcontroller can be programmed to execute further instructions to adjust the threshold when the test rod is positioned in proximity to at least one of the first proximal magnetometer, the second proximal magnetometer, the first distal magnetometer, and the second distal magnetometer in order to test an operability or functionality of the metal detection device.

The handle can comprise a sensitivity wheel. The one or more processors of the microcontroller can be programmed to execute further instructions to adjust the threshold in response to a rotation of the sensitivity wheel. The handle further comprise a sensitivity rotary potentiometer coupled to the sensitivity wheel. The one or more processors of the microcontroller can be programmed to execute instructions to determine a wheel rotational direction based on data obtained from the sensitivity rotary potentiometer.

The one or more processors of the microcontroller can be programmed to execute further instructions to apply either the signal filter or the derivative to the differential signal calculated based on the wheel rotational direction. The one or more processors of the microcontroller can be programmed to execute additional instructions to adjust the threshold based on the wheel rotational direction.

In some implementations, the one or more processors of the microcontroller can be programmed to execute further instructions to apply both the signal filter and the derivative to the differential signal calculated based on the wheel rotational direction. The one or more processors of the microcontroller can be programmed to execute additional instructions to adjust the threshold based on the wheel rotational direction.

The distal sensing portion can further comprise an inertial measurement unit (IMU) comprising a three-axis accelerometer and a three-axis gyroscope. In some implementations, an IMU can also be housed within the handle. The one or more processors of the microcontroller can be programmed to execute further instructions to adjust the threshold based on acceleration data obtained from the three-axis accelerometer and rotational data obtained from the three-axis gyroscope.

The distal sensing portion can comprise a distal light-emitting diode (LED) and the handle can comprise a proximal LED. At least one of the distal LED and the proximal LED can be an instance of the output component and lights emitted by the at least one of the distal LED and the proximal LED can be an instance of the user output.

The handle can comprise a speaker. The speaker can be another instance of the output component. Sound (e.g., a beeping sound) transmitted by the speaker can be an instance of the user output.

The distal sensing portion can be housed within a sensor housing. The sensor housing and the shaft can be made of a biocompatible material to allow for intracorporeal detection within a body of a patient.

The shaft can be made in part of stainless steel. The sensor housing can be made in part of at least one of titanium and a polymeric material. In other variations, the sensor housing can be made in part of aluminum or aluminum alloy.

At least one of the first proximal magnetometer, the second proximal magnetometer, the first distal magnetometer, and the second distal magnetometer can be an anisotropic magnetoresistance (AMR) sensor. The first proximal magnetometer can be separated from the second proximal magnetometer by a proximal magnetometer separation distance. The proximal magnetometer separation distance can be between about 4.00 mm and 5.00 mm.

The first distal magnetometer can be separated from the second distal magnetometer by a distal magnetometer separation distance. The distal magnetometer separation distance can be between about 4.00 mm and 5.00 mm.

The second distal magnetometer can be separated from the first proximal magnetometer by a gradiometer separation distance. The gradiometer separation distance can be between about 18.00 mm and 20.00 mm.

The handle can be sized to allow the handle to be grasped with one hand.

In some variations, the detected object can be a surgical needle. The detected object can also be a portion of a metallic surgical equipment. Moreover, the detected object can be at least one of an RFID-tagged sponge and a metallic-marked sponge. The distal sensing portion can further comprise an RFID reader configured to read an RFID tag embedded within the RFID-tagged sponge.

The detected object can be at least one of a non-ferromagnetic medical equipment tagged with a ferromagnetic tag or plate. The detected object can also be at least one of a surgical wire, a guidewire, and an intravascular wire. The detected object can be a stent, a vascular scaffold, or a combination thereof.

The metal detection device can also comprise a conductive element extending from at least one of the distal sensing portion and the shaft. A linking cable can be electrically coupled to the conductive element. The linking cable can extend out of the handle of the metal detection device. The linking cable can be coupled to a closed-circuit indicator.

A metal detection system is disclosed comprising a magnetic blanket configured to cover a body part of a patient and the metal detection device disclosed herein. As previously discussed, the metal detection device can comprise a handle, a shaft extending from the handle, and a distal sensing portion comprising a plurality of magnetometers. The distal sensing portion can be covered by a sensor housing.

The metal detection device can further comprise an output component configured to generate a user output to alert a user of a detected object based on magnetic field measurements obtained from the plurality of magnetometers. At least one of the shaft and the sensor housing can be configured to be inserted into the body part of the patient when the body part is covered by the magnetic blanket.

A method of detecting a magnetic object within a body of a patient is also disclosed. The method can comprise introducing a part of the metal detection device into the body of the patient. As previously discussed, the metal detection device can comprise a handle, a shaft extending from the handle, a microcontroller comprising one or more processors and memory units, an output component, and a distal sensing portion positioned distally of the shaft.

The distal sensing portion can comprise a proximal gradiometer and a distal gradiometer. The proximal gradiometer can comprise a first proximal magnetometer and a second proximal magnetometer. The distal gradiometer can comprise a first distal magnetometer and a second distal magnetometer.

The method can further comprise calculating, using the one or more processors, a differential signal from magnetic field measurements obtained from the first proximal magnetometer, the second proximal magnetometer, the first distal magnetometer, and the second distal magnetometer. The method can also comprise applying, using the one or more processors, at least one of a signal filter and a derivative to the differential signal calculated to obtain a detection signal. When a derivative is taken of the differential signal, the method can further comprise scaling down the derivative of the differential signal with a motion blocking signal.

The method can also comprise comparing, using the one or more processors, the detection signal against a sensitivity or detection threshold. The method can further comprise generating a user output, using the output component, when the detection signal exceeds the sensitivity or detection threshold.

Another method of detecting a magnetic object within a body of a patient is also disclosed. The method can comprise introducing a part of the metal detection device into the body of the patient. As previously discussed, the metal detection device can comprise a handle, a shaft extending from the handle, a distal sensing portion positioned distally of the shaft, a flexible portion connecting the shaft to the distal sensing portion, a microcontroller comprising one or more processors and memory units, and an output component. The distal sensing portion can comprise a plurality of magnetometers.

The method can also comprise squeezing a trigger on the handle to bend the flexible portion when the distal sensing portion and at least part of the flexible portion are within the body of the patient. The method can further comprise calculating, using the one or more processors, a detection signal from magnetic field measurements obtained from the plurality of magnetometers. The method can also comprise comparing, using the one or more processors, the detection signal against a threshold. The method can further comprise generating a user output, using the output component, when the detection signal exceeds the threshold.

Another method of testing a functionality of a metal detection device is disclosed. The method can comprise providing a metal detection device. The metal detection can comprise a handle, a shaft extending from the handle, a microcontroller comprising one or more processors and memory units, an output component, a distal sensing portion positioned distally of the shaft, and a sensor housing covering the distal sensing portion. The distal sensing portion can comprise a plurality of magnetometers.

The method can also comprise sliding a test rod slider on the handle in a distal direction toward the shaft. Sliding the test rod slider can cause a distal segment of a test rod housed within a lumen extending through the shaft to be translated into the sensor housing. The method can further comprise calculating, using the one or more processors, a detection signal from magnetic field measurements obtained from the plurality of magnetometers when the distal segment of the test rod is translated into the sensor housing.

The method can also comprise comparing, using the one or more processors, the detection signal against a threshold. The method can further comprise generating a user output, using the output component, when the detection signal exceeds the threshold. The method can also comprise adjusting the threshold when the distal segment of the test rod is within the sensor housing.

DETAILED DESCRIPTION

Figure 1A:
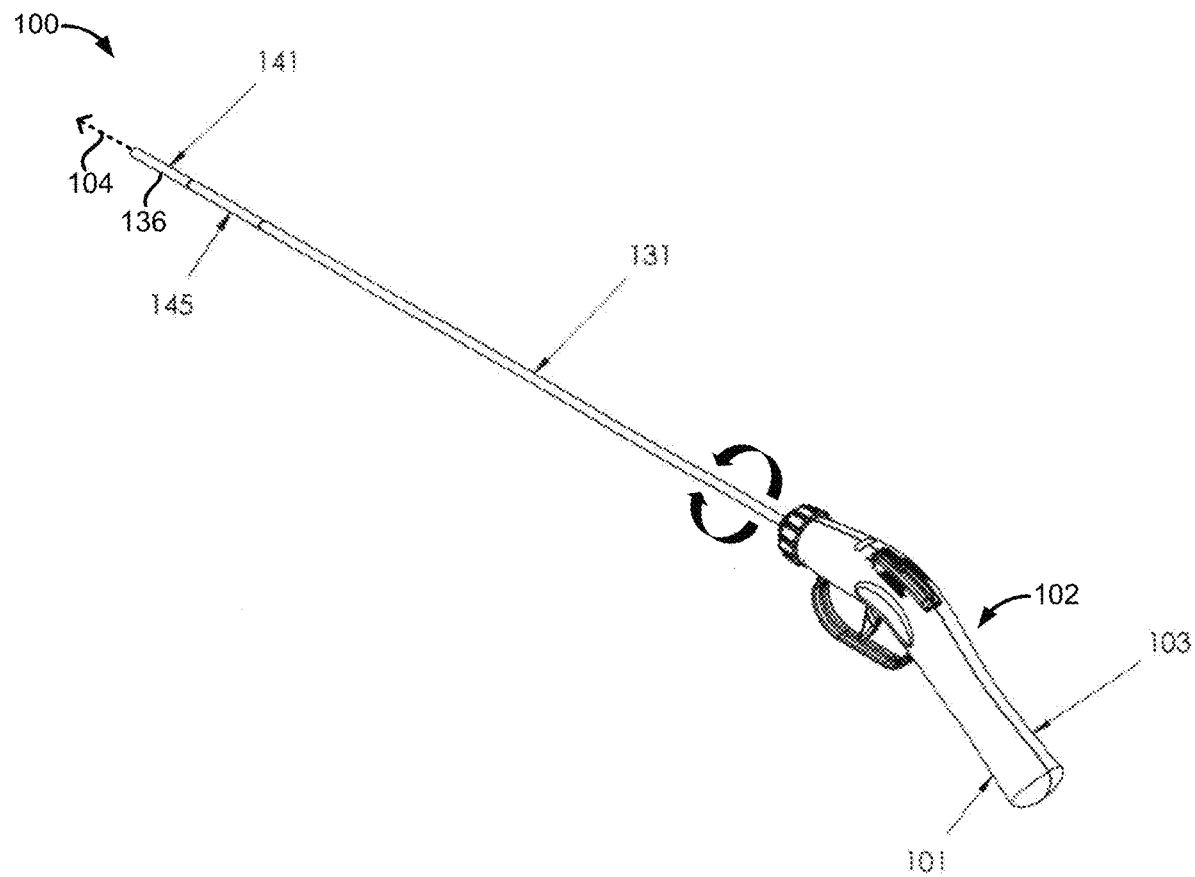
FIG. 1A illustrates an isometric view of a metal detection device.
Figure 1B:
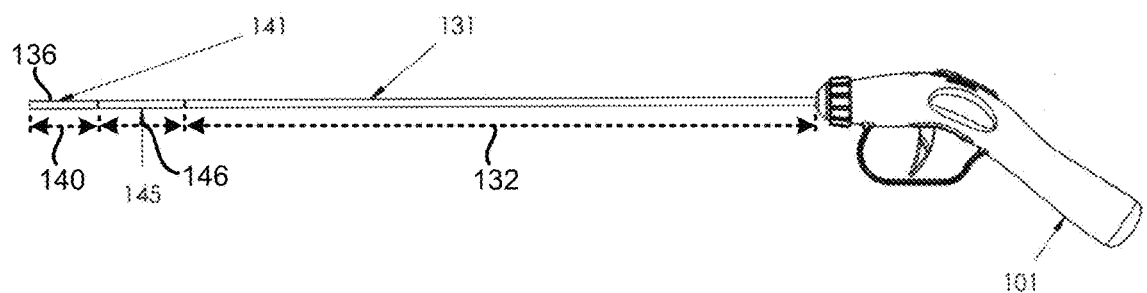
FIG. 1B illustrates a side view of the metal detection device.

FIGS. 1A-1B illustrate a metal detection device 100 comprising a handle 102, a shaft 131 extending from the handle 102, and a distal sensing portion 136 positioned distally of the shaft 131. The distal sensing portion 136 can be covered by a sensor housing 141. The metal detection device 100 can also be referred to as a sharps finder, a surgical metal detector, an RSI detector, or any combination thereof.

The distal sensing portion 136 can serve as a distal tip or distal end of the device 100. As shown in FIGS. 1A-1B, a flexible portion 145 can connect the shaft 131 to the distal sensing portion 136 or the sensor housing 141 of the distal sensing portion 136. As will be discussed in more detail in the following sections, the flexible portion 145 can be configured to bend or curve such that the distal sensing portion 136 is brought closer to the shaft 131 when the flexible portion 145 is bent.

FIG. 1A also illustrates that the shaft 131 is rotatable with respect to a longitudinal axis 104 of the shaft 131. The bending of the flexible portion 145 and the rotation of the shaft 131 can allow an operator of the device 100 (e.g., a surgeon or other medical professional) to undertake intracorporeal detection of RSIs or other ferromagnetic objects by navigating through bodily lumen or around organs of the patient.

The sensor housing 141, the flexible portion 145, and the shaft 131 can be made of a biocompatible material. In some variations, the shaft 131 can be made in part of a metallic material, a polymeric material, or a combination thereof. The shaft 131 can be made in part of a ferromagnetic metal. The shaft 131 can be made in part of stainless steel.

The sensor housing 141 can be made of a material that does not interfere with magnetic field measurements undertaken by sensors within the sensor housing 141. In some variations, the sensor housing 141 can be made of a non-ferromagnetic metallic material, a polymeric material, or a combination thereof. For example, the sensor housing 141 can be made in part of titanium. In other variations, the sensor housing 141 can be made in part of aluminum or an aluminum alloy. In additional variations, the sensor housing 141 can be made in part of a liquid crystal polymer. The sensor housing 141 can be made in part of a surgical or medical grade polytetrafluoroethylene (PTFE), polycarbonate (PC), polyether ether ketone (PEEK), or a combination thereof.

The flexible portion 145 can be made in part of a biocompatible elastomeric material. In some variations, the flexible portion 145 can be made in part of a thermoplastic elastomer. For example, the flexible portion 145 can be made in part of a polyether block amide. More specifically, the flexible portion 145 can be made in part of PEBAX®. In other variations, the flexible portion 145 can be made of a surgical grade rubber.

FIG. 1B illustrates that the sensor housing 141 can have a housing length dimension 140. The housing length dimension can be between about 40.0 mm to about 50.0 mm. For example, the housing length dimension 140 can be about 45.0 mm (more specifically, about 45.70 mm).

In other variations, the housing length dimension 140 can be less than 40.0 mm or greater than 50.0 mm. As will be discussed in more detail in the following sections, the sensor housing 141 can be sized to fit two gradiometers or at least four magnetometers, a plurality of operational amplifiers, an inertial measurement unit, a LED, and other electronic components.

The flexible portion 145 can have a flexible portion length dimension 146. The flexible portion length dimension 146 can be between about 40.0 mm to about 60.0 mm. In some variations, the flexible portion length dimension 146 can be about 50.0 mm. For example, the flexible portion length dimension 146 can be about 50.8 mm.

The shaft 131 can have a shaft length dimension 132. The shaft length dimension 132 can be a length of the exposed segment of the shaft 131. The shaft length dimension 132 can between about 300.0 mm to about 400.0 mm. In some variations, the shaft length dimension 132 can be between about 325.0 mm to about 375.0 mm. For example, the shaft length dimension 132 can be about 350.0 mm.

A segment of the shaft 131 can extend into the handle 102. The entire length of the shaft 131 can be between about 400.0 mm to about 500.0 mm (e.g., about 450.0 mm) when including the segment of the shaft 131 within the handle 102.

The shaft 131 can be hollow or include at least one lumen suitable for cables, rods, wires, or communication lines to pass through the shaft 131 and permit mechanical and/or electrical communication between the handle 102 and the distal sensing portion 136, the flexible portion 145, or a combination thereof. In other variations, the shaft 131 can comprise multiple lumens.

The shaft 131 can be entirely rigid along its length. In other variations, the shaft 131 can be flexible along its entire length such that the shaft can bend or conform to the shape of a bodily lumen. The shaft 131 can be rigid except for one or more regions of flexibility along its length.

In some variations, the shaft 131 can be directly connected to the distal sensing portion 136 or the sensor housing 141 covering the distal sensing portion 136 without the flexible portion 145. In other variations, the device 100 can comprise multiple instances of the flexible portion 145 such that a distal segment of the device 100 beyond the shaft 131 can bend in multiple directions. In some variations, the multiple instances of the flexible portion 145 can be interspersed along the length of the shaft 131 such that rigid segments of the shaft 131 are connected by flexible portion 145.

The handle 102 can comprise a left handle casing 101 and a right handle casing 103. The left handle casing 101 and the right handle casing 103 can be coupled together via fasteners (e.g., screws), adhesive, an interference fit, or a combination thereof to form the handle 102. The handle 102 can comprise a handle cavity for housing certain electronic and/or mechanical components for operating the device 100. The handle 102 can be sized to allow the handle 102 to be grasped with one hand.

The handle 102, including the left handle casing 101 and the right handle casing 103, can be made in part of a polymeric material, a metallic material, or a combination thereof. For example, the handle 102 can be made of a rigid polymeric material such as polycarbonate.

It should be appreciated that there is no limitation to the actual size, shape, or configuration of the handle 102, the shaft 131, the flexible portion 145, the sensor housing 141, or a combination thereof. For example, the device 100 can be designed or sized for hand-held use by a surgeon or other medical professional such that the handle 102 can be grasped by one hand of the surgeon or medical professional. In other variations, the device 100 can be modified specifically for implementation via a robotic surgical system such that any portion of the device 100 can be integrated with or is easily graspable by a robotic arm.

Figure 2A:
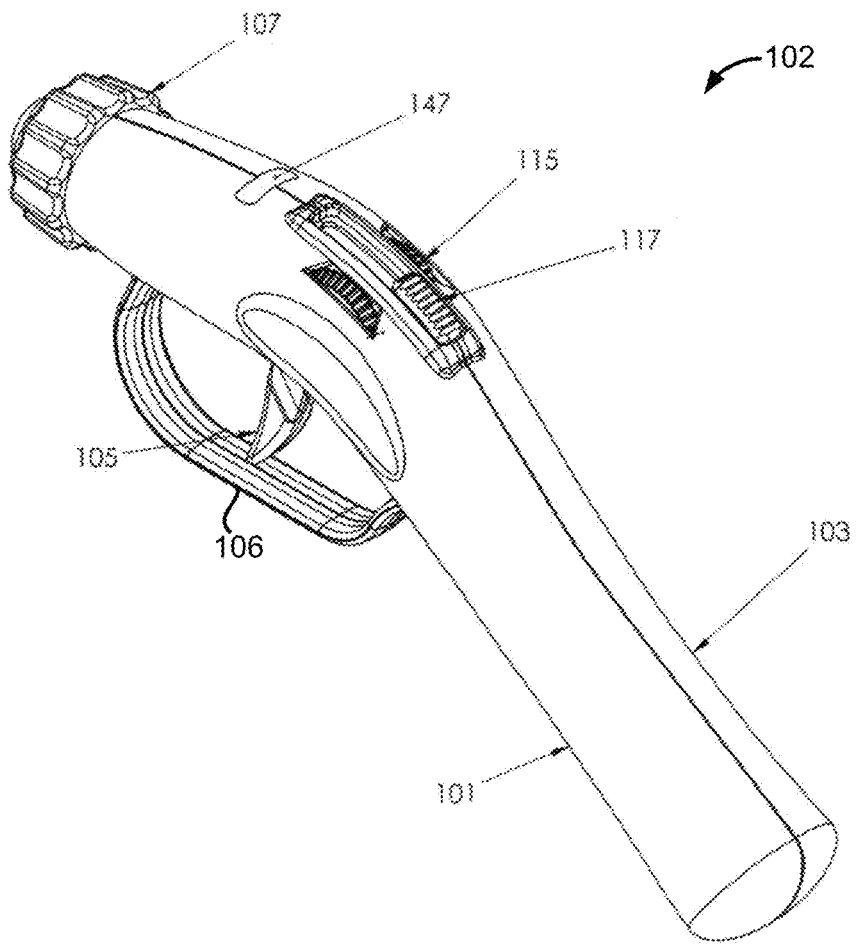
FIG. 2A illustrates an isometric view of a handle of the metal detection device.
Figure 2B:
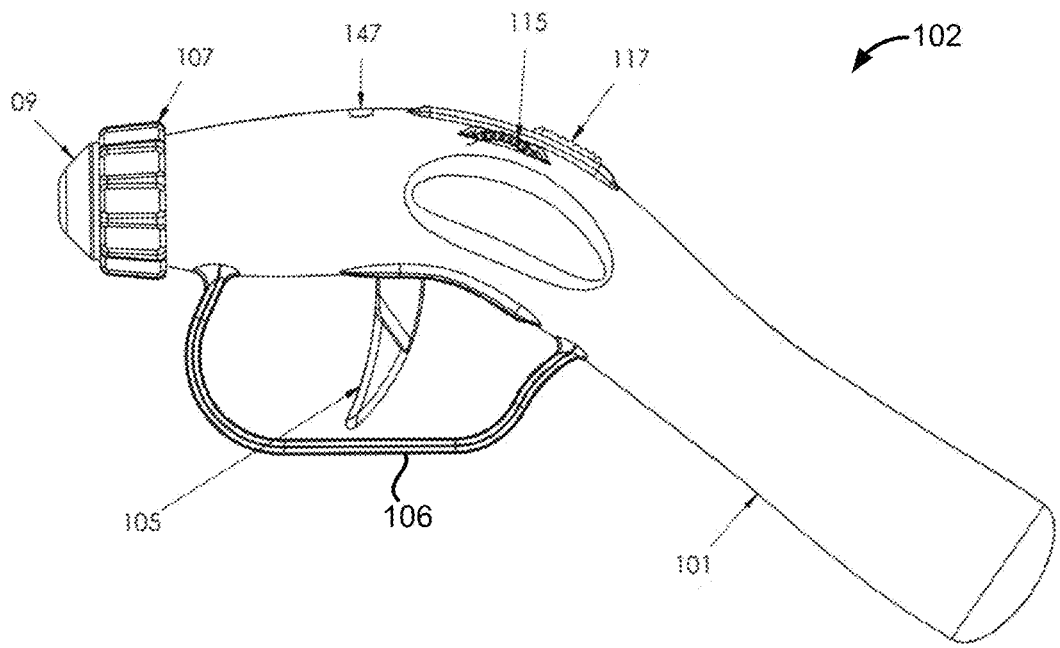
FIG. 2B illustrates a side view of the handle of the metal detection device.

FIGS. 2A-2B illustrate that the handle 102 can comprise a trigger 105, a clocking ring 107, a nose cap 109, one or more sensitivity wheels 115, a test rod slider 117, and a light transmittance window 147. The trigger 105 can be positioned on an underside of the handle 102. The trigger 105 can be protected by a trigger guard 106.

As will be discussed in more detail in the following sections, a user can squeeze the trigger 105 to control the bending of the flexible portion 145. The flexible portion 145 can be bent up to 90° (see, for example, FIG. 3B) or beyond in response to a squeezing of the trigger 105. When the flexible portion 145 is bent, the distal sensing portion 136 can be positioned closer to a distal end of the shaft 131.

The metal detection device 100 can be configured to undertake intracorporeal detection of ferromagnetic RSIs or other ferromagnetic objects even when the flexible portion 145 is bent. For example, the metal detection device 100 can be configured to undertake intracorporeal detection of ferromagnetic RSIs or other items even when the flexible portion 145 is bent between about 1° to about 90° or beyond 90°. One technical problem with traditional surgical metal detectors is that such detectors are often rigid and inflexible and an operator of such a detector (e.g., a surgeon or other medical professional) can only manipulate the detector by translating it axially or rotating the detector along its longitudinal axis by hand. This limits the range of motion of such detectors and their detection capability. For example, such detectors often cannot detect around organs or cannot extend into certain vessels. One technical advantage offered by the metal detection device 100 disclosed herein is the ability to undertake detection even when part of the elongated segment of the device 100 is bent or curved.

The clocking ring 107 can be configured to rotate when urged into an unlocked position. The clocking ring 107 can be coupled to the shaft 131. Rotating the clocking ring 107 can rotate the shaft 131. Rotating and unlocking the clocking ring 107 will be discussed in more detail in the following sections.

The nose cap 109 can serve as a distal cap of the handle 102. The nose cap 109 can also serve as a receiving and bearing surface for the clocking ring 107 when the clocking ring 107 rotates.

The one or more sensitivity wheels 115 and the test rod slider 117 can be positioned above the trigger 105 to allow for an operator (e.g., a surgeon or other medical professional) to manipulate the test rod slider 117, the sensitivity wheel 115, or a combination thereof while the operator is holding the handle 102 and squeezing the trigger 105 at the same time.

FIG. 2A illustrates that the device 100 can comprise two sensitivity wheels 115 positioned on opposite lateral sides of the test rod slider 117. This can allow the device 100 to be easily held and manipulated by both right-handed and left-handed operators.

The sensitivity wheel(s) 115 can be dialed (e.g., rotated forward or distally and rotated backward or proximally) to adjust a detection sensitivity. As will be discussed in more detail in the following sections, adjusting the sensitivity wheel(s) 115 can adjust a detection sensitivity of the device 100. For example, adjusting the sensitivity wheel(s) 115 can raise or lower a programmed threshold of detection. Also, for example, adjusting the sensitivity wheel(s) 115 can adjust a mode of operation of the device 100 such that detection signals are processed in different ways. Moreover, an operator or user of the device 100 can also switch between different modes of operation (e.g., a high speed and high sensitivity mode or a low speed and low sensitivity mode) during the course of a detection.

The test rod slider 117 can be slid forward (distally) or backward (proximally) to translate a test rod 133 (see e.g., FIGS. 4A-4B and 5B-5D) into or out of the sensor housing 141. The test rod slider 117 can be mounted between the left handle casing 101 and the right handle casing 103. The test rod 133 and the test rod slider 117 will be discussed in more detail in the following sections.

The light transmittance window 147 can allow the light generated by a lighting component (e.g., an LED) within the handle 102 to be made visible to an operator. The light transmittance window 147 can also be referred to as a light pipe or light bar. The light transmittance window 147 can be made of a light-transmitting polymeric material (e.g., an acrylic polymer), a ceramic material, or a combination thereof. The light viewable through the light transmittance window 147 can provide useful information to an operator concerning a battery life, a standby indication, an error warning, a detection status, or a combination thereof.

Figure 3A:
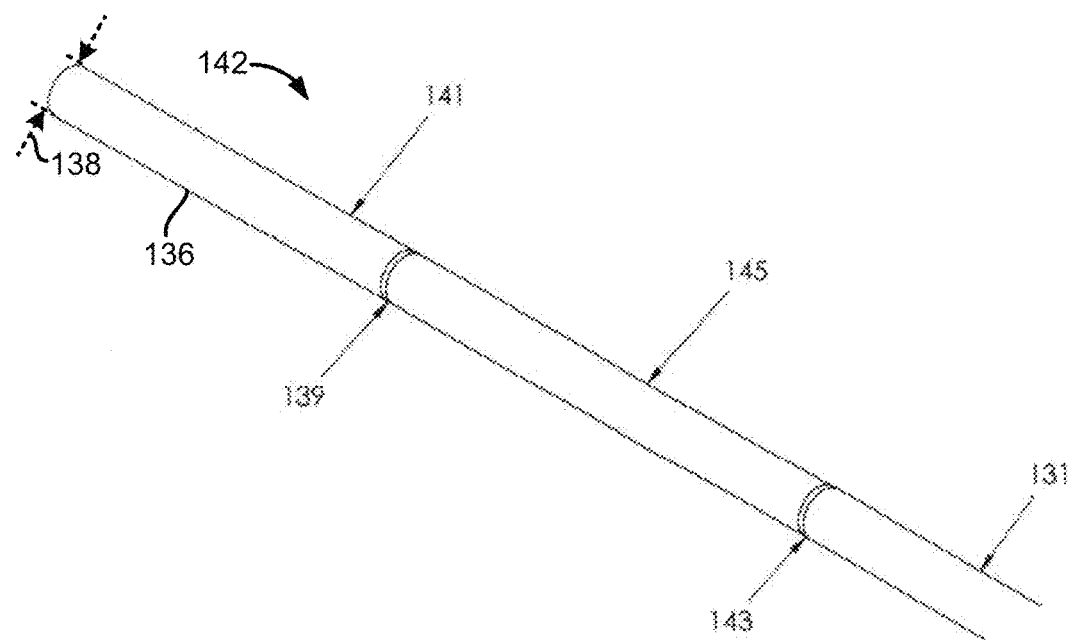
FIG. 3A illustrates a flexible portion of the metal detection device in a straightened configuration.
Figure 3B:
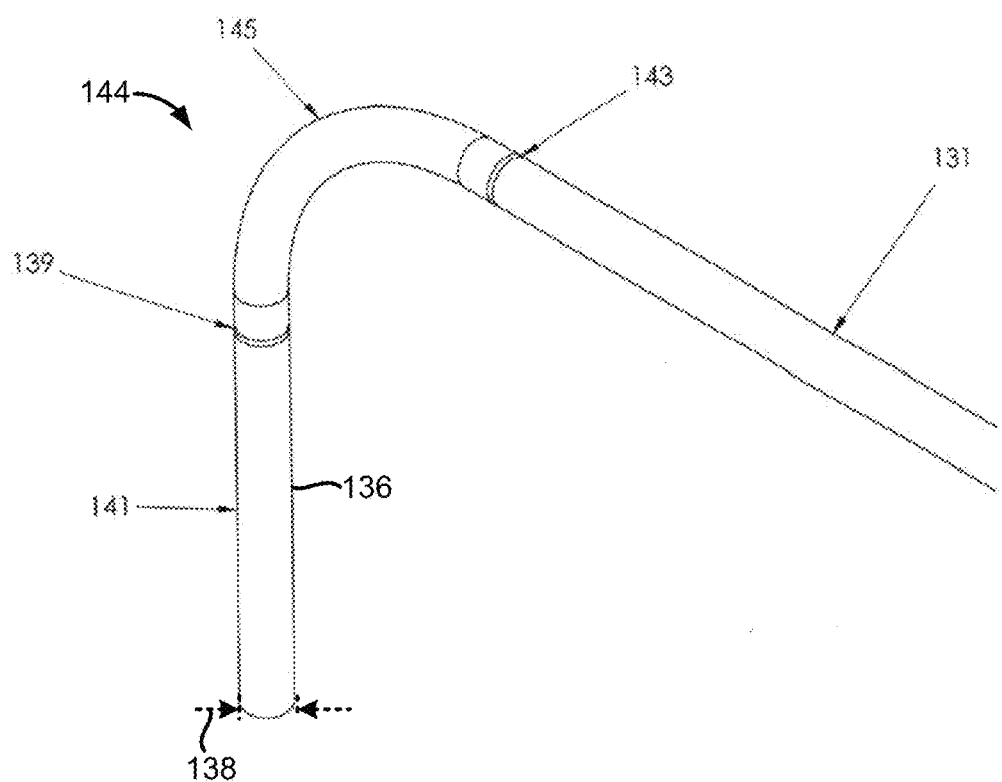
FIG. 3B illustrates a flexible portion of the metal detection device in a bent configuration.

FIGS. 3A and 3B illustrate the flexible portion 145 of the device 100 in a straightened configuration 142 and a bent configuration 144, respectively. As shown in FIG. 3B, the distal sensing portion 136 can be positioned closer to the shaft 131 (i.e., a distal segment of the shaft 131) when the flexible portion 145 is in the bent configuration 144.

The flexible portion 145 can be bracketed by a distal tube fitting 139 and a proximal tube fitting 143. The distal tube fitting 139 can couple the flexible portion 145 to the distal sensing portion 136 or the sensor housing 141 covering the distal sensing portion 136. The proximal tube fitting 143 can couple the flexible portion 145 to the shaft 131. The distal tube fitting 139 and the proximal tube fitting 143 can serve as ends of the flexible portion 145.

As will be discussed in more detail in the following sections, a pull cable 135 (see, for example, FIGS. 4B and 5D) within the shaft 131 can run the lengths of the shaft 131 and the flexible portion 145 and a distal end of the pull cable 135 can be grounded or otherwise coupled to the distal tube fitting 139. For example, the pull cable 135 can be thread through a hole defined in the distal tube fitting 139 and a knot can be tied to secure the distal end of the pull cable 135 to the distal tube fitting 139. In other variations, a ferrule or other type of ring, cap, or clip can be used to affix the distal end of the pull cable to the distal tube fitting 139.

A proximal end of the pull cable 135 can be coupled to the trigger 105. For example, the proximal end of the pull cable 135 can be wound around a spool within the trigger 105.

Squeezing the trigger 105 can pull the pull cable 135 and bend the flexible portion 145 into the bent configuration 144. The flexible portion 145 can be flexible enough to allow flexure in any desired direction.

When the trigger 105 is released, the flexible portion 145 can be biased back into the straightened configuration 142 by one or more structures within the flexible portion 145. For example, the flexible portion 145 can be biased or otherwise pushed back into the straightened configuration 142 by a spring tube 137 (see, for example, FIGS. 4A-4B, 5A-5B, and 5D) extending through the flexible portion 145.

The flexible portion 145 can be bent up to 90° or beyond in response to a squeezing of the trigger 105. For example, the flexible portion 145 can be bent about 30°, about 45°, about 60°, or about 90° with respect to its straightened configuration 142 when the trigger 105 is squeezed. The flexible portion 145 can also be bent about 95°, about 100°, about 105°, about 110°, about 115°, or about 120° when the trigger 105 is squeezed even harder.

In other variations, the trigger 105 can be replaced with another type of mechanical actuator such as one or more levers, wheels, knobs, pulls, or a combination thereof. In additional variations, the trigger 105 can be replaced with an electrical actuator such as one or more buttons, switches, or a combination thereof.

FIGS. 3A and 3B also illustrate that the sensor housing 141 can have a housing diameter 138. The housing diameter 138 can be between about 3.0 mm to about 10.0 mm. For example, the housing diameter 138 can be about 5.0 mm.

The flexible portion 145 can have a flexible portion diameter. The flexible portion diameter can be between about 3.0 mm to about 10.0 mm. For example, the flexible portion diameter can be about 5.0 mm.

The shaft 131 can have a shaft diameter. The shaft diameter can be between about 3.0 mm to about 10.0 mm. For example, the shaft diameter can be about 5.0 mm.

When the housing diameter 138, the flexible portion diameter, and the shaft diameter are all about 5.0 mm, the elongate segment of the device 100 (including the sensor housing 141, the flexible portion 145, and the shaft 131) can fit within a standard surgical trocar. This can allow the device 100 to be used for laparoscopic surgeries, open surgeries, or robotic surgeries.

Figure 4A:
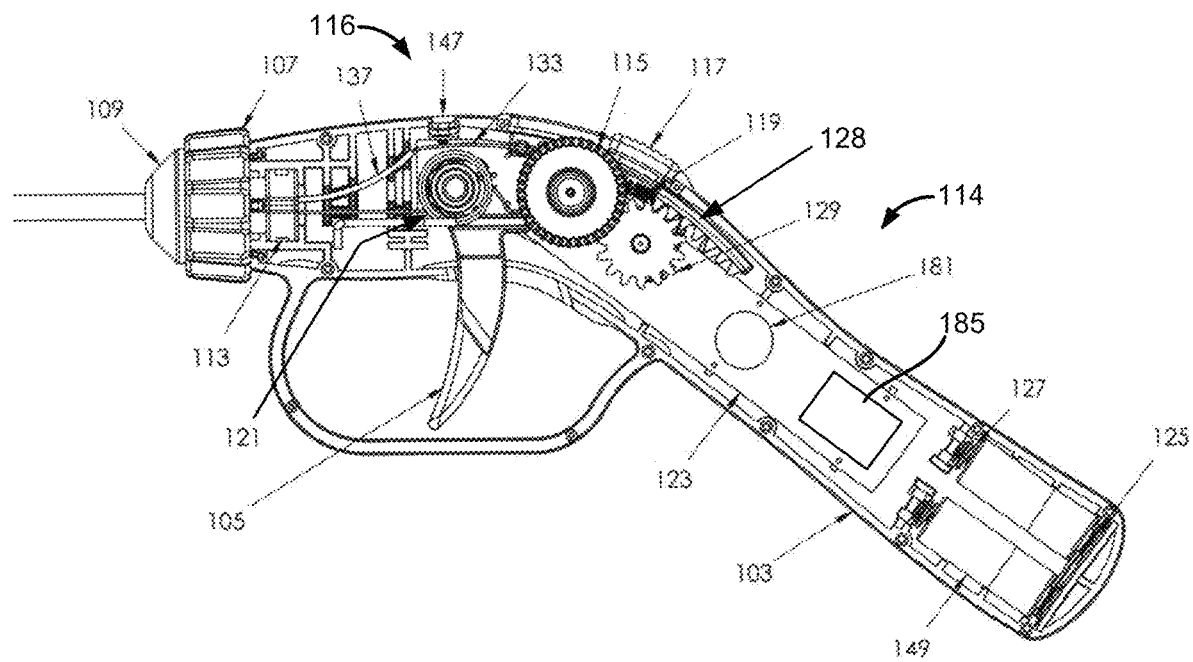
FIG. 4A illustrates a side view of the handle of the metal detection device with a left handle casing removed.

FIG. 4A illustrates a side view of the handle 102 with the left handle casing 101 removed in order to view certain components and mechanisms within the handle 102. FIG. 4A illustrates that the handle 102 can comprise a handle printed circuit board (PCB) 123. The handle PCB 123 can extend from a handle grip 114 of the handle 102 to a handle barrel 116.

The handle PCB 123 can be a rigid PCB. In other variations, the handle PCB 123 can be a flexible PCB.

The handle PCB 123 can serve as the main circuit board for electronic components housed within the handle 102. As shown in FIG. 4A, a microcontroller 185, a speaker 181, and certain potentiometers can be coupled to the handle PCB 123.

The microcontroller 185 can comprise one or more processors and memory units. The one or more processors of the microcontroller 185 can be programmed to execute instructions stored in the memory units to, among other things, determine a motion of certain components of the device 100, test a functionality of the device 100, obtain and process detection signals based on magnetic field measurements made by the magnetometers, and detect an RSI or other ferromagnetic object based on such processed detection signals.

In some variations, the microcontroller 185 can be a low-power reduced instruction set computer based (RSIC-based) microcontroller. The microcontroller 185 can be an 8-bit microcontroller. In other variations, the microcontroller can be a 16-bit or 32-bit microcontroller. For example, the microcontroller 185 can be the ATmega32U4 microcontroller distributed by Microchip Technology Inc.

The microcontroller 185 can comprise flash memory, static random-access memory (SRAM), electrically erasable programmable read-only memory (EEPROM), or a combination thereof. For example, the microcontroller 185 can comprise at least 32 kilobytes (KB) of flash memory, 2.5 KB of SRAM, and 1 KB of EEPROM.

The microcontroller 185 can have a CPU speed of at least 16 MIPS at 16 MHz. In other variations, the microcontroller 185 can have a CPU speed of 28 MIPS at 33 MHz or 36 MIPS at 40 MHz.

The microcontroller 185 can also comprise an analog-to-digital converter (ADC). For example, the microcontroller 185 can comprise a 12-channel 10-bit ADC. In other variations, the microcontroller 185 can comprise a 12-bit ADC or a 16-bit ADC. The ADC can convert voltage data obtained from the magnetometers (0V to about 5V) to digital data. For example, voltage data obtained from the magnetometers and other sensors can be converted to arbitrary signal bin units (see, e.g., FIGS. 13-17B).

Figure 4B:
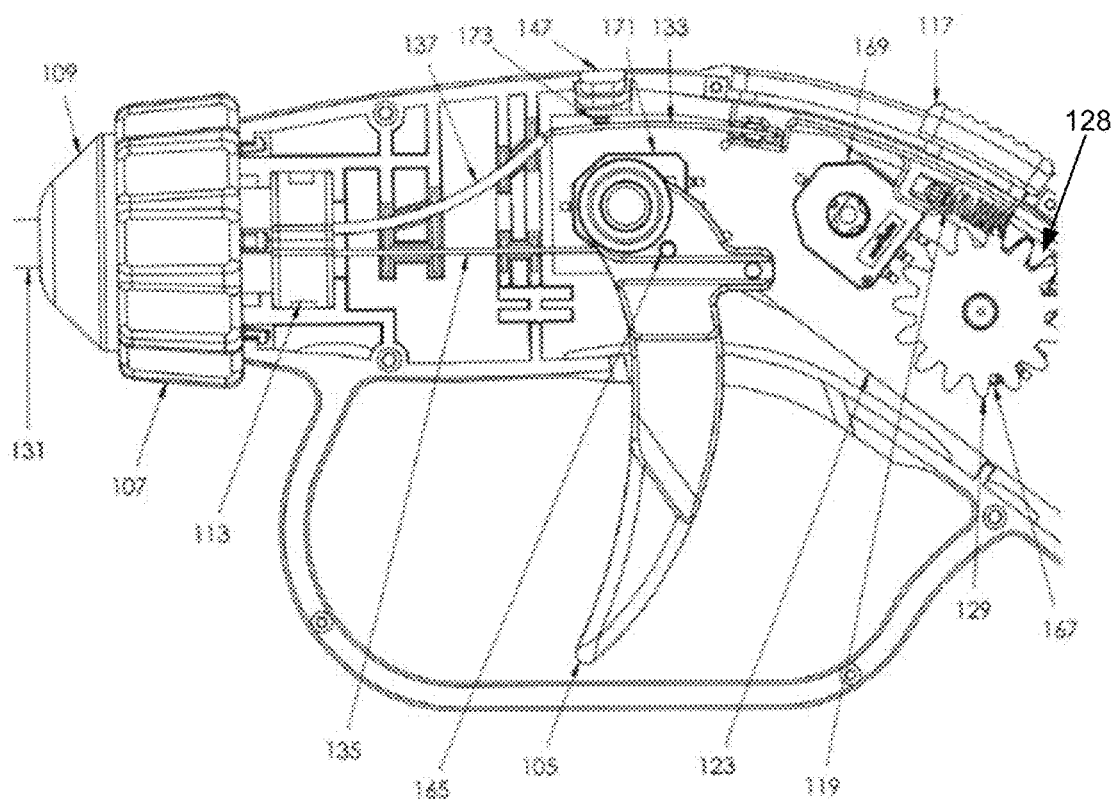
FIG. 4B illustrates a close-up side view of the handle of the metal detection device with the left handle casing removed.

Although not shown in FIGS. 4A and 4B, it is contemplated by this disclosure that the handle 102 can also comprise an inertial measurement unit (IMU). The IMU can provide up to six degrees of freedom (DoF). The IMU can be a 6-axis IMU comprising a 3-axis accelerometer and a 3-axis gyroscope. The IMU can measure tilt and angular rates and accelerations in three perpendicular axes. In some variations, the IMU can be a low-power and low-noise 16-bit IMU. For example, the IMU can be BMI055, MBI088, or BMI160 IMU provided by Bosch Sensortec GmbH. The IMU can be another instance of the IMU 159 shown in FIGS. 6 and 7A-7C. The IMU can be a handle PCB 123.

Data obtained from the IMU can be used as part of any calculations concerning a motion of the handle 102. For example, data obtained from the IMU 159 as well as the potentiometers can be used to determine whether an operator (e.g., a surgeon or other medical professional) has shaken or wobbled the handle 102 or is moving the handle 102 too rapidly. One or more processors of the microcontroller 185 can be programmed to execute further instructions to disregard a sudden motion of the handle 102 or a motion exceeding one or more motion thresholds based on acceleration data obtained from the 3-axis accelerometer and rotational data obtained from the 3-axis gyroscope.

The device 100 can comprise a number of output components coupled to the handle PCB 123. The output components can include one or more lights and/or audio components. The output components can be configured to generate a user output (e.g., a sound and/or light) to alert a user of a detected RSI or ferromagnetic object. The output components can also be configured to generate a user output to indicate a functionality or operational status of the device 100. For example, the user output can be generated by the output components to convey information concerning a battery life of the device 100, a standby indication, an error warning, a detection status, or a combination thereof.

The output components can include a speaker 181, a proximal light-emitting diode (LED) 173, a distal LED 183 (see FIG. 6A), or a combination thereof. The speaker 181 and/or the proximal LED 173 can be coupled to the handle PCB 123. In other variations, only the speaker 181 can be coupled to the handle PCB 123.

As shown in FIG. 4A, the speaker 181 can be positioned within the handle grip 114. In other variations, the speaker 181 can be positioned within the handle barrel 116.

The speaker 181 can be configured to transmit a sound or audio message to inform the operator of a detected RSI or other ferromagnetic object or to convey information concerning a functionality or operational status of the device 100. For example, speaker 181 can generate a sound or audio message to convey information concerning a battery life of the device 100, a standby indication, an error warning, a detection status, or a combination thereof.

The sound can be a beeping sound, a ringing sound, a chime, a pitched tonal sound, or a combination thereof. The audio message can be a pre-recorded message or phrase.

The proximal LED 173 can be positioned within the handle barrel 116. In other variations, the proximal LED 173 can be positioned in proximity to the nose cap 109 or along the handle grip 114.

The handle 102 can further comprise a light transmittance window 147. The light transmittance window 147 can be positioned directly over the proximal LED 173 or close to the proximal LED 173. The light transmittance window 147 can allow a light generated by the proximal LED 173 to be made visible to an operator. The light transmittance window 147 can also be referred to as a light pipe or light bar. The light transmittance window 147 can be made of a light-transmitting polymeric material (e.g., an acrylic polymer), a ceramic material, or a combination thereof.

The device 100 can also comprise a distal LED 183. The distal LED 183 can be coupled to a flexible circuit or circuit board in the distal sensing portion 136 (see FIG. 6A). The sensor housing 141 can comprise a light transmittance window or a light-transmitting portion to allow light generated by the distal LED 183 to be made visible to an operator via endoscopy.

The distal LED 183 can function similarly to the proximal LED 173. The same light or light patterns generated by the proximal LED 173 can also be generated by the distal LED 183 (and vice versa). The light or light patterns generated by the proximal LED 173 and/or the distal LED 183 can convey information concerning a battery life of the device 100, a standby indication, an error warning, a detection status, or a combination thereof.

For example, both the proximal LED 173 and the distal LED 183 can generate a green blinking light pattern (a heartbeat light pattern) to indicate that the device 100 is in operation. The proximal LED 173 can generate a red blinking light pattern to inform the operator that one or more electronic components or sensors within the sensor housing 141 are disconnected or the entire sensor housing 141 has broken off or is disconnected. The speaker 181 can also generate a warning sound when the one or more electronic components or sensors within the sensor housing 141 are disconnected or the entire sensor housing 141 has broken off or is disconnected.

The speaker 181 can also generate a beeping sound or beeping sound pattern when a detection signal is above a sensitivity or detection threshold to inform the operator that the device 100 has potentially detected an RSI or other ferromagnetic object. The sound (e.g., beeping sound or sound pattern) generated by the speaker 181 can correspond to the size of the detection signal above the sensitivity or detection threshold. For example, the speaker 181 can generate a louder instance of the beeping sound or sound pattern when the size of the detection signal above the sensitivity or detection threshold exceeds a predetermined size threshold. The proximal LED 173, the distal LED 183, or a combination thereof can also generate a light or light pattern (e.g., a sustained blue light or blinking blue light) when the detection signal is above the sensitivity or detection threshold. In some variations, the brightness of the light or light pattern generated by the proximal LED 173, the distal LED 183, or a combination thereof can correspond to the size of the detection signal above the sensitivity or detection threshold. For example, the proximal LED 173, the distal LED 183, or a combination thereof can generate a brighter instance of the light or light pattern when the size of the detection signal above the sensitivity or detection threshold exceeds a predetermined size threshold.

FIG. 4A also illustrates that the device 100 can comprise a power source configured to supply power to the device 100 and its various electronic components. In some variations, the power source can be a portable power source such as one or more batteries 149. As shown in FIG. 4A, one or more batteries 149 can be housed within the handle 102. For example, the handle grip 114 can comprise a battery holder or battery holding compartment comprising a positive battery terminal 125 and a negative battery terminal 127.

In some variations, the battery 149 can be a rechargeable battery. In these variations, the device 100 can comprise an input for receiving power from an external power source to charge the battery 149. In additional variations, the device 100 can comprise an input for receiving power from an external power source and the device 100 can be powered completely by the external power source without batteries 149.

As shown in FIGS. 4A and 4B, the handle 102 can further comprise a trigger 105, a trigger potentiometer 171 coupled to at least part of the trigger 105, and a trigger spring 121. A proximal segment of the pull cable 135 can be coupled to at least part of the trigger 105.

The trigger 105 can be actuated to control the bending of the flexible portion 145. As previously discussed, the trigger 105 can be connected to the flexible portion 145 by a pull cable 135 extending through the shaft 131 and the flexible portion 145. Squeezing the trigger 105 pulls the pull cable 135 and bends the flexible portion 145. Bending the flexible portion 145 brings the distal sensing portion 136 closer to the shaft 131.

As shown in FIG. 4B, the trigger 105 can comprise a pull cable hole 165. The pull cable 135 can extend through the pull cable hole 165 and be tied or otherwise secured to the trigger 105 at the pull cable hole 165. In other variations, a proximal segment or end of the pull cable 135 can extend into a cavity within the trigger 105 and be wound around a spool within the trigger 105. The pull cable 135 can also be attached to the trigger 105 via adhesives, clips, ties, ferrules, or a combination thereof.

As previously discussed, the pull cable 135 can run the length of the shaft 131 and the flexible portion 145 and a distal end of the pull cable 135 can be tied or otherwise coupled to the distal tube fitting 139 at a distal end of the device 100.

For example, the pull cable 135 can be thread through a hole defined in the distal tube fitting 139 and a knot can be tied to secure the distal end of the pull cable 135 to the distal tube fitting 139. In other variations, a ferrule or other type of ring, cap, or clip can be used to affix the distal end of the pull cable to the distal tube fitting 139.

In some variations, the pull cable 135 can be a braided cable or wire such as a braided stainless steel cable. In other variations, the pull cable 135 can be a polymeric cable or wire such as a nylon cable or wire.

The trigger spring 121 can spring load the trigger 105 such that the trigger 105 returns to its starting position after being squeezed. The trigger spring 121 can be a torsion spring. The trigger spring 121 can mate with features on the interior of the handle 102 to provide resistance.

Squeezing the trigger 105 can pull the pull cable 135 and bend the flexible portion 145 into the bent configuration 144. The flexible portion 145 can be flexible enough to allow flexure in any desired direction.

When the trigger 105 is released, the flexible portion 145 can be biased back into the straightened configuration 142 by one or more structures within the flexible portion 145. For example, the flexible portion 145 can be biased or otherwise pushed back into the straightened configuration 142 by a spring tube 137 (see, for example, FIGS. 4A-4B, 5A-5B, and 5D) extending through the flexible portion 145.

In other variations, the trigger 105 can be replaced with another type of mechanical actuator such as one or more levers, wheels, knobs, pulls, or a combination thereof. In additional variations, the trigger 105 can be replaced with an electrical actuator such as one or more buttons, switches, or a combination thereof.

FIG. 4B illustrates a close-up side view of the handle 102 with the left handle casing 101, the trigger spring 121, and the sensitivity wheel 115 removed for ease of viewing. FIG. 4B illustrates that a trigger potentiometer 171 can be coupled to a rotatable portion of the trigger 105. For example, the trigger potentiometer 171 can be coupled to a trigger axle (obscured in FIG. 4B) extending through the trigger potentiometer 171.

The trigger potentiometer 171 can be a rotary potentiometer. In some variations, the trigger potentiometer 171 can be mounted to part of the handle PCB 123. In other variations, the trigger potentiometer 171 can be mounted to another PCB within the handle 102.

The trigger potentiometer 171 can provide data concerning a trigger speed (e.g., how fast the trigger is pulled). Since bending the flexible portion 145 subjects the distal sensing portion 136 to sudden motions and brings the distal sensing portion 136 closer to the ferromagnetic shaft 131, the trigger potentiometer 171 provides data that can be used to adjust a sensitivity threshold or detection threshold.

For example, the one or more processors of the microcontroller 185 can be programmed to raise a sensitivity or detection threshold (i.e., decrease a detection sensitivity) to account for any magnetic field distortions caused by the shaft 131 when the distal sensing portion 136 is bent toward the shaft 131 and/or any sudden movements of the distal sensing portion 136. For example, data obtained from the trigger potentiometer 171 can also be used to determine whether an operator has jerked or yanked the distal sensing portion 136 by squeezing the trigger 105 too forcefully or quickly.

Raising the sensitivity or detection threshold (also referred to as lowering or decreasing the detection or sensitivity level) can be done to avoid false positive signals. When the trigger is squeezed or otherwise moves too quickly, this can create a sharp spike in the magnetic field detected. In these instances, the one or more processors of the microcontroller 185 can be programmed to execute instructions to determine that a trigger motion exceeds a trigger motion threshold or trigger motion threshold range, the one or more processors can then be programmed to execute further instructions to raise the programmed sensitivity or detection threshold (i.e., lower the sensitivity level of the device 100) in response to the sudden or uncontrolled movement of the trigger 105. This can be done to forestall or tamper any false positive signals. In this manner, data obtained from the trigger potentiometer 171 can be factored into detection algorithms run by the microcontroller 185.

The handle 102 can further comprise one or more sensitivity wheels 115 configured to adjust a programmed sensitivity or detection threshold in response to a rotation of the sensitivity wheel(s) 115. At least part of the sensitivity wheel(s) 115 can protrude out of cutout(s) defined along the handle casings to allow an operator to dial or rotate the sensitivity wheel(s) 115.

An operator can dial or rotate the sensitivity wheel 115 in order to raise or lower the programmed sensitivity or detection threshold. For example, an operator can dial or otherwise rotate at least one of the sensitivity wheels 115 forward (or in a distal direction) to increase the sensitivity level of the device 100. Increasing the sensitivity level of the device 100 can allow the device 100 to more accurately detect the presence of small or weakly magnetized RSIs or other ferromagnetic objects within the body of the subject. Increasing the sensitivity level of the device 100 can decrease a programmed sensitivity or detection threshold.

The operator can dial or otherwise rotate at least one of the sensitivity wheels 115 backward (or in a proximal direction) to decrease the sensitivity level of the device 100. Decreasing the sensitivity level of the device 100 can increase a programmed sensitivity or detection threshold. The operator can decrease the sensitivity level of the device 100 when false positive signals from ferromagnetic medical equipment in proximity to the patient (e.g., metallic surgical equipment or carts) makes it difficult for the operator to perceive actual detection signals.

The device 100 can comprise a number of discrete sensitivity levels. For example, the device 100 can comprise 11 discrete sensitivity levels with a default level being level 7. The device 100 can generate a user output (e.g., two successive beeps or beeping sounds) when the sensitivity level has reached either an upper (e.g., level 11) or lower limit (e.g., level 1).

The sensitivity wheel(s) 115 can be rotationally coupled to a sensitivity rotary potentiometer 169 (see FIG. 4B, the sensitivity wheels 115 are removed in FIG. 4B for ease of viewing). The sensitivity rotary potentiometer 169 can be coupled to the handle PCB 123.

The sensitivity rotary potentiometer 169 can provide data concerning a wheel rotation and, thereby, a sensitivity level desired by the operator.

The one or more processors of the microcontroller 185 can be programmed to execute instructions to smooth out potentiometer signals obtained from the sensitivity rotary potentiometer 169 to reduce signal noise and to observe such signals for consecutive up or down signal spikes as a result of the operator dialing at least one of the sensitivity wheels 115 forward or backward. The one or more processors of the microcontroller 185 can be programmed to execute instructions to adjust a sensitivity or detection threshold when either two consecutive sensitivity upward signal spikes or two consecutive downward signal spikes are detected. For example, the one or more processors of the microcontroller 185 can be programmed to execute instructions to lower the sensitivity or detection threshold (i.e., increase the sensitivity level) when two consecutive upward signal spikes from the sensitivity rotary potentiometer 169 are observed.

The sensitivity level of the device 100 can also be adjusted by the device 100 automatically (i.e., without the operator's input). For example, the sensitivity level of the device 100 can be decreased and the sensitivity or detection threshold can be increased if a trigger motion calculated from data obtained from the trigger potentiometer 171 exceeds a trigger motion threshold. Also, for example, the sensitivity level of the device 100 can be decreased and the sensitivity or detection threshold can be increased when the magnetometers are periodically reset to filter out any settling events or level changes. For example, the magnetometers can be reset periodically (e.g., every 5 seconds) using a mag reset function to realign the domains in the magnetometers with a current pulse. This is done in case the magnetometers are highly affected by a strong magnetic field. Resetting the magnetometers can cause a transient signal spike or bump. Raising the sensitivity or detection threshold at the same time the magnetometers are reset can reduce the likelihood of false positive signals.

Although sensitivity wheel(s) 115 are mentioned in the present examples, it is contemplated by this disclosure and it should be understood by one of ordinary skill that the sensitivity wheel(s) 115 are just one example of a sensitivity actuator. In other variations, the sensitivity actuator can be implemented one or more sliders, knobs, buttons, switches, or a combination thereof. In additional variations, the sensitivity actuator can be implemented as user interface controls presented through an electronic display or touchpad.

FIGS. 4A and 4B also illustrate that the handle 102 can comprise a test rod slider 117. In some variations, the test rod slider 117 can slide along a dorsal side of the handle barrel 116. The test rod slider 117 can be slid or otherwise translated forward (distally) or backward (proximally) in order to translate a test rod 133 axially within the shaft 131. Sliding the test rod slider 117 forward can extend or drive a distal end of the test rod 133 into the sensor housing 141 and in proximity to the magnetometers of the distal sensing portion 136.

The test rod 133 can be made in part of a ferromagnetic material. For example, the test rod 133 can be made in part of a ferromagnetic metal. The test rod 133 can be made in part of a magnetic stainless steel such as a ferritic stainless steel, martensitic stainless steel, or duplex stainless steel.

The test rod 133 can be flexible and bendable. For example, the test rod 133 can be implemented as a flexible ferromagnetic cable or rod.

The test rod 133 can have a known magnetic signature such that when the test rod 133 is extended into the sensor housing 141, a magnetic field distortion caused by the test rod 133 can be accounted for. The test rod 133 can be used to verify a functionality of the device 100 and/or re-zero a magnetic environment in-situ.

The test rod slider 117 can be spring-loaded by an extension spring 119 to pull the test rod slider 117 back to its default starting position (see, for example, FIG. 4B) when a distal force is not applied to the test rod slider 117. One end of the extension spring 119 can be grounded to the right handle 102 and the other end of the extension spring 119 can be attached or coupled to at least part of the test rod slider 117.

A proximal end of the test rod 133 can be secured or otherwise coupled to the test rod slider 117. For example, the proximal end of the test rod 133 can be secured to a proximal portion of the test rod slider 117 by adhesives, fasteners, ties, clips, or a combination thereof.

The test rod 133 can be partially housed within a spring tube 137. A distal end of the test rod 133 can extend out of the spring tube 137. A proximal end of the spring tube 137 can be secured or otherwise coupled to the right handle casing 103. For example, the proximal end of the spring tube 137 can be secured to features of the right handle casing 103 by adhesives, fasteners, ties, clips, or a combination thereof. The spring tube 137 can extend from the handle 102 through the shaft 131 and the flexible portion 145.

In addition to serving as a housing for the test rod 133, the spring tube 137 can also be used to bias the flexible portion 145 back to its unbent configuration 144 when the trigger 105 is released. The spring tube 137 can be made in part of polyethylene terephthalate (PET). In other variations, the spring tube 137 can be made of a polymeric material or copolymer exhibiting shape-memory characteristics. The spring tube 137 can also provide a degree of rigidity or structure to the flexible portion 145.

One advantage of using the spring tube 137 to house the test rod 133 and bias the flexible portion 145 back to its unbent configuration 144 is that the same component can serve multiple functions, thereby reducing the total number of components running through a small-diameter shaft. This also helps to reduce the overall complexity of the device 100.

The handle 102 further comprises a slider potentiometer 167 mounted or otherwise coupled to the handle PCB 123. The slider potentiometer 167 can be coupled via gears to at least part of the test rod slider 117.

For example, FIGS. 4A and 4B illustrate that the test rod slider 117 can be coupled to a rack gear 128 configured to interact with a spur gear 129. The spur gear 129 can be rotationally coupled to the slider potentiometer 167. For example, a gear axle extending from the spur gear 129 can be coupled to the slider potentiometer 167.

Data obtained from the slider potentiometer 167 can be used to determine a slider position of the test rod slider 117. The slider position can be indicative of the relative positioning of the test rod 133 with respect to the magnetometers of the distal sensing portion 136. For example, the slider position can be indicative of the relative positioning of the test rod 133 with respect to at least one of the first proximal magnetometer 202, the second proximal magnetometer 204, the first distal magnetometer 208, and the second distal magnetometer 210.

When the test rod 133 is driven by the test rod slider 117 into the sensor housing 141 and in proximity to the magnetometers, the one or more processors of the microcontroller 185 can be programmed to execute instructions to conduct certain detection diagnostics. For example, the one or more processors of the microcontroller 185 can be programmed to execute instructions to compare magnetic field measurements obtained from the magnetometers with known magnetic field values associated with the ferromagnetic test rod 133.

The one or more processors of the microcontroller 185 can be programmed to execute further instructions to instruct the output component (e.g., the speaker 181 or the LEDs) to generate a user output (e.g., a sound or light pattern) to inform an operator of the results of the diagnostic.

The test rod 133 can be used in combination with the sensitivity wheel 115 to gauge a functionality or operability of the device 100. For example, when an operator is not sure if the device 100 is functioning properly, the operator can increase the sensitivity level of the device 100 by dialing the sensitivity wheel 115 forward or in a distal direction and pushing the test rod slider 117 forward to translate the ferromagnetic test rod 133 into the sensor housing 141 and in proximity to the magnetometers. The operator can gain insight into the functionality of the device 100 based on the user output generated by the device 100 in this scenario.

Data obtained from the slider potentiometer 167 can also be used as part of any calculations or determinations concerning a motion (e.g., speed and/or acceleration) of the test rod 133. For example, data obtained from the slider potentiometer 167 can be used to determine whether an operator has extended or retracted the test rod 133 too quickly.

The device 100 can also automatically increase the sensitivity level when data obtained from the slider potentiometer 167 indicates that the test rod slider 117 is being pushed forward to test the functionality of the device 100. The device 100 can automatically increase the sensitivity level (thereby decreasing the sensitivity or detection threshold) to increase the chance that the test rod 133 is detected by the magnetometers. For example, the one or more processors of the microcontroller 185 can be programmed to execute instructions to determine that the test rod 133 is being advanced forward based on data or signals obtained from the slider potentiometer 167. The one or more processors of the microcontroller 185 can be programmed to execute further instructions to lower the sensitivity or detection threshold in response to the test rod 133 being advanced forward or into the sensor housing 141.

In other instances, the test rod 133 can be used to cancel out false positive signals or noise attributed to ferromagnetic objects in the sensing environment. For example, the test rod 133 can be used to cancel out false positive signals or noise attributed to ferromagnetic medical equipment in proximity to the patient (e.g., metallic surgical equipment or carts). Such noise can make it difficult for the operator to perceive actual detection signals. For example, an operator desiring to re-zero a magnetic environment can apply a distal force to the test rod slider 117 to extend the test rod 133 into the sensor housing 141 and maintain the test rod 133 in this extended configuration for a period of time above a predetermined time threshold. In response to the test rod 133 being maintained in this extended configuration, the one or more processors of the microcontroller 185 can be programmed to execute instructions to decrease a sensitivity level of the device 100 by raising a sensitivity or detection threshold until most (or a significant number of) false positive signals are below the new sensitivity or detection threshold except for signals attributed to the test rod 133. This new higher sensitivity or detection threshold can then be maintained even when the operator has let go of the test rod slider 117 and the test rod 133 is no longer extended into the sensor housing 141 and is in a retracted configuration. The operator can then undertake detection at this new lowered sensitivity level (i.e., with a higher sensitivity or detection threshold).

Figure 5A:
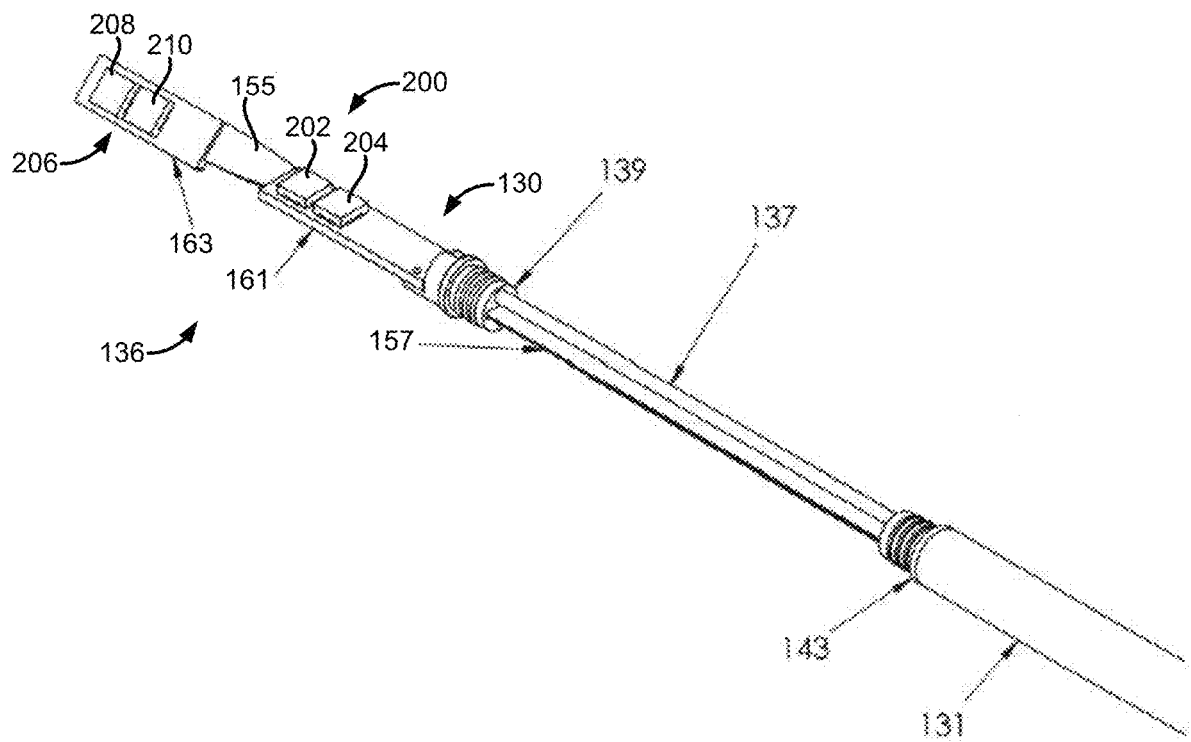
FIG. 5A illustrates an isometric view of a distal segment of the metal detection device with a sensor housing and the flexible portion removed and a test rod in a retracted configuration.

FIG. 5A illustrates an isometric view of a distal segment of the device 100 with the sensor housing 141 and the flexible portion 145 removed for ease of viewing and the test rod 133 in a retracted configuration 130. The retracted configuration 130 can be the default configuration of the test rod 133. A distal end of the test rod 133 can be within the spring tube 137 when in the retracted configuration 130. When in the retracted configuration 130, the test rod 133 can be sufficiently distanced from the magnetometers such that the magnetism of the test rod 133 does not significantly affect the detection of RSIs or other ferromagnetic metallic objects.

Figure 5B:
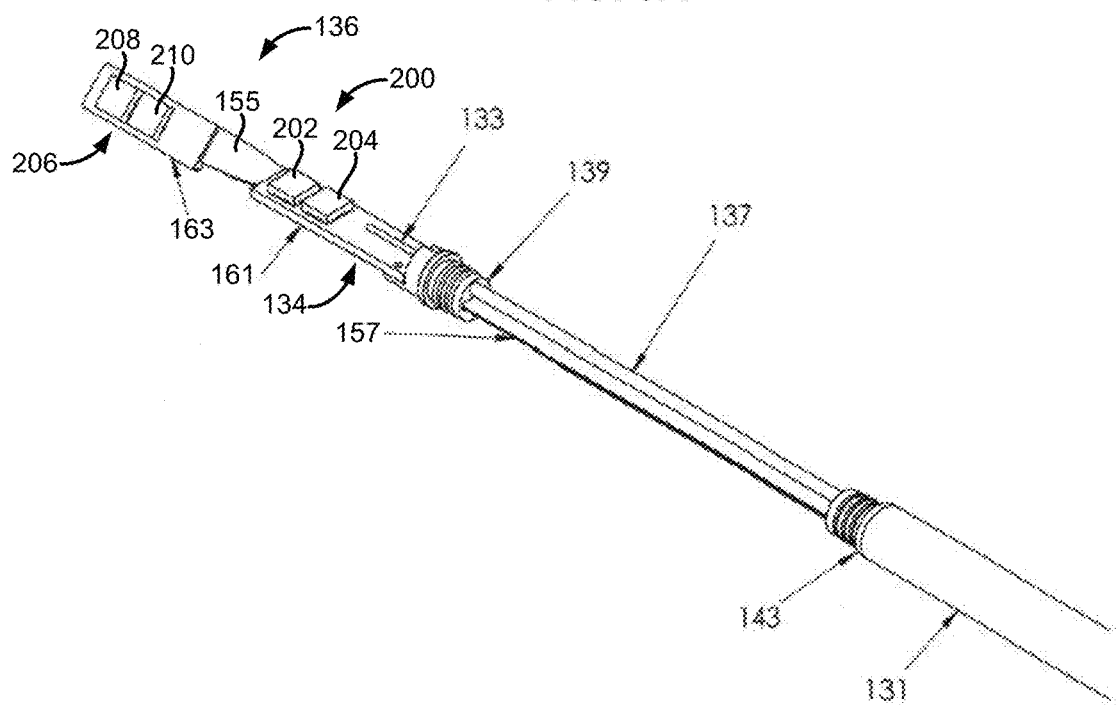
FIG. 5B illustrates an isometric view of the distal segment of the metal detection device with the sensor housing and the flexible portion removed and the test rod in an extended configuration.

FIG. 5B illustrates an isometric view of the same distal segment of the device 100 shown in FIG. 5A but with the test rod 133 in an extended configuration 134. The test rod 133 can be in the extended configuration 134 when an operator has advanced the test rod slider 117 on the handle 102 and is applying a distal force to the test rod slider 117 to maintain the test rod slider 117 in the advanced position (e.g., by keeping the operator's finger on the test rod slider 117). The distal end of the test rod 133 can be extended or advanced out of the spring tube 137 into the sensor housing 141 (not shown in FIG. 5B for ease of viewing) when the test rod 133 is in the extended configuration 134. When in the extended configuration 134, the test rod 133 can be in close enough proximity to the magnetometers of the distal sensing portion 136 such that the ferromagnetic test rod 133 is detectable by at least one of the magnetometers (a magnetic field distortion caused by the test rod 133 is detectable by at least one of the first proximal magnetometer 202, the second proximal magnetometer 204, the first distal magnetometer 208, and the second distal magnetometer 210).

The distal end of the test rod 133 can be separated from a second proximal magnetometer 204 by several millimeters when the test rod 133 is in the extended configuration 134. For example, the distal end of the test rod 133 can be separated from the second proximal magnetometer by between about 1.0 mm to about 5.0 mm when the test rod 133 is in the extended configuration 134. In other variations, the distal end of the test rod 133 can be separated from the second proximal magnetometer 204 by between about 5.0 mm to about 10.0 mm when the test rod 133 is in the extended configuration 134. In other variations, the distal end of the test rod 133 can be separated from the second proximal magnetometer by more than 10.0 mm or less than 1.0 mm when the test rod 133 is in the extended configuration 134. In additional variations, the distal end of the test rod 133 can be positioned over one or more of the magnetometers but not in contact with the magnetometers when the test rod 133 is in the extended configuration 134.

For example, in some variations, the distal tip of the test rod 133 can be positioned about 1.0 mm past the second proximal magnetometer 204 when the test rod 133 is in the extended configuration 134.

In alternative variations, the distal tip of the test rod 133 can be positioned about 1.0 mm past the first proximal magnetometer 202 when the test rod 133 is in the extended configuration 134.

In additional variations, the distal tip of the test rod 133 can be positioned about 1.0 mm past the first distal magnetometer 208 or the second distal magnetometer 210 when the test rod 133 is in the extended configuration 134. In these variations, the entire test rod 133 can be positioned over the magnetometers.

Figure 5C:
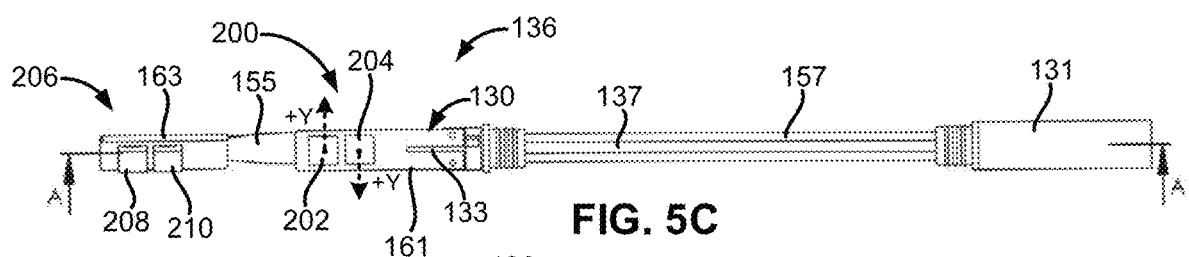
FIG. 5C illustrates a top plan view of the distal segment of the metal detection device with the sensor housing and the flexible portion removed and the test rod in the extended configuration.
Figure 5D:
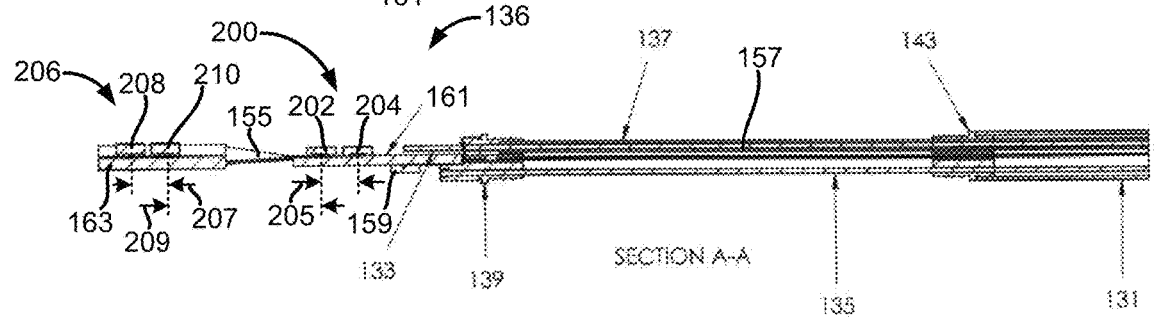
FIG. 5D illustrates a sectional view of the distal segment of the metal detection device along section A-A shown in FIG. 5C.

FIG. 5C illustrates a top plan view of the distal segment of the device 100 with the sensor housing 141 and the flexible portion 145 removed for ease of viewing and the test rod 133 in the extended configuration 134. FIG. 5D illustrates a sectional view of the same distal segment along section A-A shown in FIG. 5C.

FIGS. 5C and 5D illustrate that an elongate flex circuit 157 can couple one or more PCBs in the distal sensing portion 136 to the handle PCB 123. For example, the elongate flex circuit 157 can couple a proximal rigid PCB 161 to the handle PCB 123. The elongate flex circuit 157 allows the magnetometers, amplifiers, and other electronic components within the distal sensing portion 136 to be in electrical communication with the microcontroller 185 mounted to the handle PCB 123. The segment of the elongate flex circuit 157 extending through the flexible portion 145 can bend or flex when the flexible portion 145 is pulled into the bent configuration 144 in response to squeezing of the trigger 105.

The elongate flex circuit 157 or flexible printed circuit can comprise conductive metallic foils printed, adhered, laminated, deposited, and/or otherwise bonded to a flexible polymeric film such as a PET film or polyimide film. In other variations, the elongate flex circuit 157 can be a rigid-flex PCB or a flexible printed circuit having some rigidity.

The elongate flex circuit 157 can be positioned in between the spring tube 137 partially housing the test rod 133 and the pull cable 135 within the flexible portion 145 and the shaft 131. The pull cable 135 can be positioned closer to a bottom or ventral side of the flexible portion 145 and the shaft 131.

As previously discussed, the distal end of the pull cable 135 can be grounded or otherwise coupled to the distal tube fitting 139. The distal end of the pull cable 135 can be grounded or otherwise coupled to the distal tube fitting 139 below or inferior to the elongate flex circuit 157 as shown in FIG. 5D.

For example, the pull cable 135 can be thread through a hole defined in the distal tube fitting 139 and a knot can be tied to secure the distal end of the pull cable 135 to the distal tube fitting 139. In some variations, the hole on the distal tube fitting 139 can be positioned below or inferior to the elongate flex circuit 157 as. In other variations, a ferrule or other type of ring, cap, or clip can be used to affix the distal end of the pull cable to the distal tube fitting 139.

The spring tube 137 can be positioned closer to a top or dorsal side of the flexible portion 145 and the shaft 131. As shown in FIG. 5D, a distal of the spring tube 137 can be coupled to the distal tube fitting 139 above or superior to the elongate flex circuit 157.

One technical advantage of the arrangement of tubes, circuits, and cables within the flexible portion 145 is that the flexible portion 145 can be bent quickly and effectively and can, just as easily, recover its unbent or straightened configuration. For example, the spring tube 137 within the flexible portion 145 can allow the flexible portion 145 to spring back to its default straightened configuration. Moreover, the flexible portion 145 can bend without adversely affecting the test rod 133 within the spring tube 137.

The metal detection device 100 can be configured to undertake testing (for example, functionality testing) or re-zeroing even when the flexible portion 145 is bent. For example, the metal detection device 100 can be configured to undertake testing or re-zeroing even when the flexible portion 145 is bent between about 1° to about 90° or beyond 90°. Heretofore, to the best of applicant's knowledge, no surgical metal detectors have been designed with a bendable test rod 133 to allow for testing or re-zeroing when part of the elongated sensing segment of the device 100 is bent or curved.

FIGS. 5A-5D also illustrate that the distal sensing portion 136 can comprise a proximal gradiometer 200 comprising a first proximal magnetometer 202 and a second proximal magnetometer 204 and a distal gradiometer 206 comprising a first distal magnetometer 208 and a second distal magnetometer 210. For the purposes of this disclosure, the term magnetometer refers to a device or sensor for measuring components of a magnetic field and the term gradiometer refers to a combination of such devices or sensors for measuring a gradient of magnetic field components.

The first proximal magnetometer 202 and the second proximal magnetometer 204 can be mounted or otherwise coupled to a proximal PCB or circuit and the first distal magnetometer 208 and the second distal magnetometer 210 can be mounted or otherwise coupled to a distal PCB or circuit. In the variation shown in FIGS. 5A-5D and 6A-6B, the first proximal magnetometer 202 and the second proximal magnetometer 204 can be mounted or otherwise coupled to proximal rigid PCB 161. In this variation, the first distal magnetometer 208 and the second distal magnetometer 210 can be mounted or otherwise coupled to a distal rigid PCB 163.

The proximal rigid PCB 161 can be connected or otherwise coupled to the distal rigid PCB 163 by a distal flex circuit 155. In other variations, the first distal magnetometer 208 and the second distal magnetometer 210 can be mounted or otherwise coupled to a flex circuit.

Although FIGS. 5A-5D illustrate a variation of the device 100 comprising two gradiometers and four magnetometers, it is contemplated by this disclosure that the device 100 can comprise three or more gradiometers or only one gradiometer.

The first proximal magnetometer 202 can be positioned distally of the second proximal magnetometer 204. The first distal magnetometer 208 can be positioned distally of the second distal magnetometer 210.

The first proximal magnetometer 202 can be positioned distally in series with the second proximal magnetometer 204 such that the first proximal magnetometer 202 is positioned distally of the second proximal magnetometer 204 along a longitudinal axis (for example, the longitudinal axis 104 shown in FIG. 1A). The first distal magnetometer 208 can be positioned distally in series with the second distal magnetometer 210 such that the first distal magnetometer 208 is positioned distally of the second distal magnetometer 210.

FIG. 5D illustrates that the first proximal magnetometer 202 can be separated from the second proximal magnetometer 204 by a proximal magnetometer separation distance 205. In some variations, the proximal magnetometer separation distance 205 can be between about 4.00 mm and 5.00 mm. For example, the proximal magnetometer separation distance 205 can be between about 4.50 mm and 4.75 mm.

The first distal magnetometer 208 can be separated from the second distal magnetometer 210 by a distal magnetometer separation distance 207. In some variations, the distal magnetometer separation distance 207 can be between about 4.00 mm and 5.00 mm. For example, the distal magnetometer separation distance 207 can be between about 4.50 mm and 4.75 mm.

The second distal magnetometer 210 can be separated from the first proximal magnetometer 202 by a gradiometer separation distance 209. In some variations, the gradiometer separation distance 209 can be between about 18.00 mm and 20.00 mm. For example, the gradiometer separation distance 209 can be between about 18.50 mm and 18.85 mm.

One technical problem faced by the applicants is how to design a surgical magnetic detector to detect small or diminutive magnetic items such as small surgical needles or pieces of surgical equipment that have broken off during surgery. One technical solution discovered by the applicants is the device 100 disclosed herein having magnetometers and gradiometers positioned and spaced according to the dimensions provided heretofore. The applicants discovered that the separation distances disclosed herein (e.g., the magnetometer separation distances and/or the gradiometer separation distances) allow the device 100 to more effectively detect small needles or other small ferromagnetic sharps or items.

Moreover, the device 100 disclosed herein having magnetometers and gradiometers positioned and spaced according to the dimensions provided heretofore, as well as the magnetometer orientations, and unique signal combinations, can all help with sensing objects of interest and help with reducing signal size for erroneous signals caused by moving through native magnetic field lines in the operating room (e.g., magnetic field lines attributed to the earth, the hospital building, medical equipment, etc.)

The distal sensing portion 136 can also comprise an inertial measurement unit (IMU) 159. The IMU 159 can provide up to six degrees of freedom (DoF). The IMU 159 can be a 6-axis IMU comprising a 3-axis accelerometer and a 3-axis gyroscope. The IMU 159 can measure tilt and angular rates and accelerations in three perpendicular axes. In some variations, the IMU can be a low-power and low-noise 16-bit IMU. For example, the IMU 159 can be BMI055, MBI088, or BMI160 IMU provided by Bosch Sensortec GmbH.

Data obtained from the IMU 159 can be used as part of any calculations concerning a speed and acceleration of the distal sensing portion 136. For example, data obtained from the IMU 159 as well as the potentiometers can be used to determine whether an operator has jerked or yanked the distal sensing portion 136. One or more processors of the microcontroller 185 can be programmed to execute further instructions to disregard a sudden motion of at least one of the distal sensing portion 136 and the shaft 131 based on acceleration data obtained from the 3-axis accelerometer and rotational data obtained from the 3-axis gyroscope.

In some variations, the IMU 159 can be mounted to the proximal rigid PCB 161. In other variations, the IMU 159 can be mounted to the distal rigid PCB 163 or another part of the distal sensing portion 136.

In some variations, data received from the IMU 159 (for example, acceleration data from the 3-axis accelerometer and/or gyroscope data from the 3-axis gyroscope) can influence whether the device 100 lowers a sensitivity level or detection sensitivity. Lowering the sensitivity level or detection sensitivity can involve raising a sensitivity or detection threshold to avoid false positive signals. For example, when data received from the IMU 159 indicates that the distal sensing portion 136 is experiencing heightened or exaggerated motion (e.g., the operator rotates the shaft 131 too quickly or squeezes/lets go of the trigger too quickly), this can create a sharp spike in the magnetic field detected. In these instances, the one or more processors of the microcontroller 185 can be programmed to execute instructions to determine that the distal sensing portion 136 is experiencing heightened or exaggerated motion based on data obtained from the IMU 159 (for example, when motion data obtained from the IMU 159 exceeds a predetermined motion threshold or motion threshold range), the one or more processors can then be programmed to execute further instructions to raise a programmed sensitivity or detection threshold to lower a sensitivity of the device 100 in response to the sudden or uncontrolled movement of the distal sensing portion 136. This can be done to forestall or tamper any false positive signals.

In certain variations, the one or more processors can also be programmed to execute further instructions to divide signal or data obtained from the various magnetometers by a magnitude of the heightened motion signal or a scaled version of the heightened motion signal to reduce the likelihood of false positive signals created by the heightened motion. This can be considered an instance of motion blocking or scaling down the detection signal.

Figure 6A:
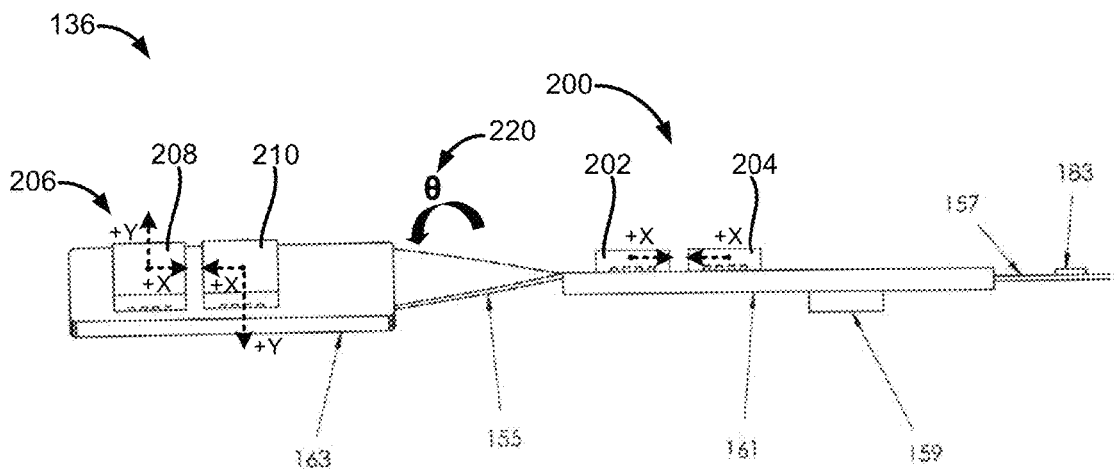
FIG. 6A illustrates a close up of the distal sensing portion of the metal detection device with the sensor housing removed.

FIG. 6A illustrates a side close-up view of one variation of the distal sensing portion 136 with the sensor housing 141 removed. The distal sensing portion 136 can comprise a proximal gradiometer 200 comprising a first proximal magnetometer 202 and a second proximal magnetometer 204 and a distal gradiometer 206 comprising a first distal magnetometer 208 and a second distal magnetometer 210.

Although FIGS. 5A-5D and 6A-6B illustrate the device 100 comprising two gradiometers and four magnetometers, it is contemplated by this disclosure that the device 100 can comprise three or more gradiometers or six or more magnetometers. In other variations, the device 100 can comprise only one gradiometer comprising two magnetometers or one gradiometer comprising two magnetometers and an additional magnetometer disposed distal or proximal to the one gradiometer.

The first proximal magnetometer 202, the second proximal magnetometer 204, the first distal magnetometer 208, and the second distal magnetometer 210 can be two-axis magnetometers, each having an x-axis and a y-axis. For example, each of the first proximal magnetometer 202, the second proximal magnetometer 204, the first distal magnetometer 208, and the second distal magnetometer 210 can have a positive x-axis (+x-axis), a negative x-axis (−x-axis), a positive y-axis (+y-axis), and a negative y-axis (−y-axis). Each of the x-axis and the y-axis can be considered a sensitive axis of the magnetometer.

The +x-axis of the first proximal magnetometer 202 can be oriented opposite the +x-axis of the second proximal magnetometer 204. The +y-axis of the first proximal magnetometer 202 can be oriented opposite the +y-axis of the second proximal magnetometer 204 (see FIGS. 5C and 6A).

The −x-axis of the first proximal magnetometer 202 can be oriented opposite the −x-axis of the second proximal magnetometer 204. The −y-axis of the first proximal magnetometer 202 can be oriented opposite the −y-axis of the second proximal magnetometer 204.

The sensitive axes (e.g., the x-axis and the y-axis) of the first proximal magnetometer 202 and the second proximal magnetometer 204 can be pointed in opposite directions to cancel out or reduce common magnetic field influences (e.g., the earth's magnetic field, magnetic field influences from medical equipment in the operating room, or field influences as a result of motion) such that local magnetic field distortions or influences are more pronounced or detectable and a larger part of the overall signal.

In other variations, only the +x-axis of the first proximal magnetometer 202 is oriented opposite the +x-axis of the second proximal magnetometer 204 or only the +y-axis of the first proximal magnetometer 202 is oriented opposite the +y-axis of the second proximal magnetometer 204.

Figure 6B:
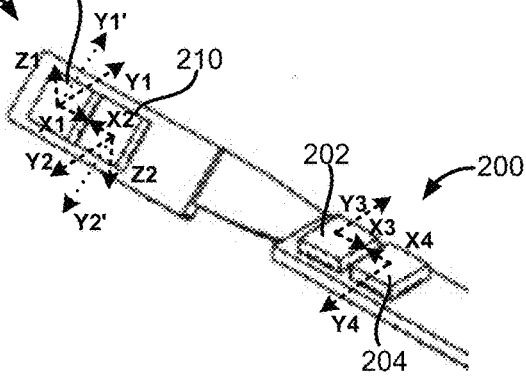
FIG. 6B illustrates a close-up perspective view of the distal sensing portion of the metal detection device with the sensor housing removed.

The +x-axis of the first distal magnetometer 208 can be oriented opposite the +x-axis of the second distal magnetometer 210 and the +y-axis of the first distal magnetometer 208 can be oriented opposite the +y-axis of the second distal magnetometer 210 (see FIGS. 6A and 6B).

In other variations, only the +x-axis of the first distal magnetometer 208 is oriented opposite the +x-axis of the second distal magnetometer 210 or only the +y-axis of the first distal magnetometer 208 is oriented opposite the +y-axis of the second distal magnetometer 210.

The sensitive axes (e.g., the x-axis and the y-axis) of the first distal magnetometer 208 and the second distal magnetometer 210 can be pointed in opposite directions to cancel out common magnetic field influences (e.g., the earth's magnetic field) such that local magnetic field distortions or influences are more pronounced or detectable.

Although reference is made to each of the magnetometers or magnetic sensors comprising an x-axis (e.g., +x-axis) and a y-axis (e.g., +y-axis), it is contemplated by this disclosure that any reference to a x-axis (e.g., +x-axis) or a y-axis (e.g., +y-axis) can also refer to a single-axis magnetometer where the magnetometer or magnetic sensor only has an x-axis or y-axis. Therefore, any references to four two-axis magnetometers (e.g., a first proximal magnetometer 202, a second proximal magnetometer 204, a first distal magnetometer 208, and a second distal magnetometer 210) can also be applied to eight one-axis magnetometers (e.g., a first proximal magnetometer, a second proximal magnetometer, a third proximal magnetometer, a fourth proximal magnetometer, a first distal magnetometer, a second distal magnetometer, a third distal magnetometer, and a fourth distal magnetometer). In some implementations, the distal sensing portion 136 can comprise four gradiometers with each gradiometer having two one-axis magnetometers.

In some variations, certain common magnetic field measurements obtained from the proximal gradiometer 200 (the first proximal magnetometer 202, the second proximal magnetometer 204, or a combination thereof) and the distal gradiometer 206 (the first distal magnetometer 208, the second distal magnetometer 210, or a combination thereof) can be canceled out or reduced in order to magnify or make more pronounced local magnetic field distortions or influences caused by RSIs or other ferromagnetic objects. For example, by canceling out common signals or common magnetic field influences (e.g., the earth's magnetic field or magnetic field distortions caused by surrounding ferromagnetic hospital equipment), local magnetic field distortions caused by an RSI or other ferromagnetic object closer to one gradiometer can cause a bigger signal at the closer gradiometer than the other gradiometer positioned farther away.

As will be discussed in more detail in the following sections, the one or more processors of the microcontroller 185 can be programmed to execute instructions stored in the memory units to calculate a differential signal from magnetic field measurements obtained from the first proximal magnetometer 202, the second proximal magnetometer 204, the first distal magnetometer 208, and the second distal magnetometer 210.

The distal sensing portion 136 can also comprise one or more operational amplifiers to amplify raw output signals from at least one of the first proximal magnetometer 202, the second proximal magnetometer 204, the first distal magnetometer 208, and the second distal magnetometer 210. The operational amplifiers can amplify the raw output signals from the magnetometers before such signals are transmitted to the ADC 186 or an ADC component of the microcontroller 185 within the handle 102. In some variations, the one or more operational amplifiers can be mounted to an underside of the PCBs within the distal sensing portion 136. For example, a first proximal operational amplifier and a second proximal operational amplifier can be mounted to an underside of the proximal rigid PCB 161 to amplify signals from the first proximal magnetometer 202 and the second proximal magnetometer 204, respectively. Also, for example, a first distal operational amplifier and a second distal operational amplifier can be mounted to an underside of the distal rigid PCB 163 to amplify signals from the first distal magnetometer 208 and the second distal magnetometer 210, respectively (see, for example, FIGS. 7A-7C).

At least one of the first proximal magnetometer 202, the second proximal magnetometer 204, the first distal magnetometer 208, and the second distal magnetometer 210 can be an anisotropic magnetoresistance (AMR) sensor. For example, at least one of the first proximal magnetometer 202, the second proximal magnetometer 204, the first distal magnetometer 208, and the second distal magnetometer 210 can be a two-axis AMR sensor. At least one of the first proximal magnetometer 202, the second proximal magnetometer 204, the first distal magnetometer 208, and the second distal magnetometer 210 can be a solid-state AMR sensor designed for low-field magnetic sensing.

As s more specific example, at least one of the first proximal magnetometer 202, the second proximal magnetometer 204, the first distal magnetometer 208, and the second distal magnetometer 210 can be an HMC 1052 AMR sensor (Part No. HMC1052L-TR) distributed by Honeywell International Inc.

In other variations, at least one of the first proximal magnetometer 202, the second proximal magnetometer 204, the first distal magnetometer 208, and the second distal magnetometer 210 can be a three-axis AMR sensor.

AMR sensors can make use of a magneto-resistive material (e.g., permalloy) to act as a magnetometer. Permalloy is an alloy containing roughly 80% nickel and 20% iron. The alloy's resistance depends on the angle between the metallization and the direction of current flow. In a magnetic field, magnetization rotates toward the direction of the magnetic field and the rotation angle depends on the external field's magnitude. For example, the AMR sensors can include thin strips of permalloy (e.g., NiFe magnetic film) whose electrical resistance varies with a change in the magnetic field.

In some variations, the magnetometers can be any type of magneto-resistive sensor that provides a change in resistance in response to a change in a magnetic field along a given axis. In other variations, the magnetometers can be any type of vector magnetometer for measuring the vector components of a magnetic field.

The magnetometers (any one of the first proximal magnetometer 202, the second proximal magnetometer 204, the first distal magnetometer 208, and the second distal magnetometer 210) can comprise a communication interface that can transmit magnetic field measurements using a communication protocol. The magnetometers can operate with a low voltage power supply such as, for example, a power supply providing voltage less than about 2.0 V, 2.5V, 3.0V, 3.5V, 4.0V, 4.5V, 5.0V, 5.5V, or 6.0V. The magnetometers can be designed to be surface mounted to the PCBs of the distal sensing portion 136. For example, the first proximal magnetometer 202 and the second proximal magnetometer 204 can be surface mounted to the proximal rigid PCB 161 and the first distal magnetometer 208 and the second distal magnetometer 210 can be surface mounted to the distal rigid PCB 163.

FIG. 6A also illustrates that the device 100 can comprise a distal LED 183. The distal LED 183 can be mounted to a distal end of the elongate flex circuit 157 near the proximal rigid PCB 161. In other variations, the distal LED 183 can be mounted to the proximal rigid PCB 161, the distal flex circuit 155, or the distal rigid PCB 163.

The sensor housing 141 (see, for example, FIGS. 1A, 1B, 3A, 3B, and 7C) can comprise a light transmittance window or a light transmitting portion to allow light generated by the distal LED 183 to be made visible to an operator via endoscopy.

The distal LED 183 can function similar to the proximal LED 173. The same light or light patterns generated by the distal LED 183 can also be generated by the proximal LED 173 (and vice versa). The light or light patterns generated by the distal LED 183 and/or the proximal LED 173 can convey information concerning a battery life of the device 100, a standby indication, an error warning, a detection status, or a combination thereof.

FIGS. 5A-5D and 6A-6B also illustrate that the distal rigid PCB 163 can be angularly rotated with respect to the proximal rigid PCB 161. The distal rigid PCB 163 can be maintained in this rotated or twisted configuration with respect to the proximal rigid PCB 161.

For example, the distal rigid PCB 163 can be maintained in this rotated or twisted configuration by the sensor housing 141 (not shown in FIG. 6A for ease of viewing). Also, for example, the distal rigid PCB 163 can be maintained in this rotated or twisted configuration by one or more fixation components such as one or more clips, clasps, space fillers, or a combination thereof.

The distal rigid PCB 163 can be rotated by a twist angle 220. In some variations, the twist angle 220 can be about 45 degrees.

In other variations, the twist angle 220 can be about 60 degrees, between about 45 degrees and 60 degrees, or less than about 45 degrees. In certain variations, the twist angle 220 can be about 30 degrees.

In some variations, the twist angle 220 can refer to an angle of rotation of at least one of the second distal magnetometer 210 and the first distal magnetometer 208 with respect to the first proximal magnetometer 202.

The distal rigid PCB 163 can be rotated about the distal flex circuit 155 connecting the proximal rigid PCB 161 to the distal rigid PCB 163. While FIGS. 5A-5D and 6A-6B illustrate the distal rigid PCB 163 rotated in a counterclockwise rotational direction when viewed from a proximal end of the distal sensing portion 136 to a distal end of the distal sensing portion 136, it is contemplated by this disclosure that the distal rigid PCB 163 can also be rotated in a clockwise rotational direction when viewed from the proximal end of the distal sensing portion 136 to the distal end of the distal sensing portion 136.

In some variations, one of the axes of the magnetometers on the distal rigid PCB 163 can be aligned with one of the axes of the magnetometers on the proximal rigid PCB 161. For example, each of the x-axes of the first distal magnetometer 208 and the second distal magnetometer 210 can be axially aligned with or positioned along the same axial plane as the x-axes of the first proximal magnetometer 202 and the second proximal magnetometer 204. In these variations, the other axis of the magnetometers on the distal rigid PCB 163 can be out of alignment with the other axis of the magnetometers on the proximal rigid PCB 161. For example, each of the y-axes of the first distal magnetometer 208 and the second distal magnetometer 210 can be out of alignment or rotated (for example, by the twist angle 220) with respect to the y-axes of the first proximal magnetometer 202 and the second proximal magnetometer 204.

Although FIGS. 6A and 6B illustrate the x-axes of the magnetometers as being axially aligned or in planar alignment and the y-axes being out of alignment, it is contemplated by this disclosure that the y-axes of the magnetometers can be axially aligned or in planar alignment and the x-axes can be out of alignment.

Twisting, contorting, or otherwise rotating the distal rigid PCB 163 with respect to the proximal rigid PCB 161 can allow the magnetometers of the distal gradiometer 206 to provide magnetic field measurements in at least one additional axis. For example, when the magnetometers of the distal gradiometer 206 are two-axis magnetometers (for example, magnetometers have an x-axis and a y-axis), twisting, contorting, or otherwise rotating the distal rigid PCB 163 can allow the magnetometers of the distal gradiometer 206 to provide magnetic field measurements in a third axis when one of the axes of the magnetometers on the distal rigid PCB 163 are axially aligned or in planar alignment with the same axis on the proximal rigid PCB 161 (for example, when the x-axes are substantially axially aligned or positioned along the same axial plane as the x-axes on the other board). In this example, the y-axes of the magnetometers on the distal rigid PCB 163 would provide additional magnetic field measurements in a third axis.

In addition, although FIGS. 5A-5D and 6A-6B illustrate the distal rigid PCB 163 as being twisted, contorted, or otherwise rotated, it is contemplated by this disclosure that the proximal rigid PCB 161 can be twisted, contorted, or otherwise rotated.

One technical advantage of twisting, contorting, or otherwise rotating one of the gradiometer circuit boards with respect to the other gradiometer circuit board (e.g., the distal rigid PCB 163 with respect to the proximal rigid PCB 161) is to allow the applicant to use smaller and cheaper two-axis magnetometers for sensing rather than having to rely on expensive and bulkier three-axis magnetometers. As previously discussed, twisting, contorting, or otherwise rotating one of the gradiometer circuit boards can allow the magnetometers on the twisted or rotated board to be used as pseudo "three-axis magnetometers" such that the magnetometers provide magnetic field measurements in an additional axis. In this manner, the twist or rotation can allow the applicant to achieve three-dimensional detection sensitivity with two-dimensional sensors.

For example, FIG. 6B illustrates that when the distal rigid PCB 163 is twisted or rotated, the y-axes of the first distal magnetometer 208 and the second distal magnetometer 210 (now referred to as Y1' and Y2', respectively) can be broken up into y-vector components (Y1 and Y2, respectively) substantially aligned with the y-axes of the first proximal magnetometer 202 and the second proximal magnetometer 204 and new z-vector components (Z1 and Z2, respectively) that have no equivalents on the proximal gradiometer 200. The new z-vector components can act as a pseudo third axis such that additional magnetic field measurements can be obtained along this additional axis.

Another technical advantage of twisting, contorting, or otherwise rotating one of the gradiometer circuit boards with respect to the other gradiometer circuit board (e.g., the distal rigid PCB 163 with respect to the proximal rigid PCB 161) is that differentials or comparisons of magnetic field values can be taken from magnetometer-pairs on the same gradiometer board but also from magnetometers on different gradiometer boards. These differentials or comparisons can be used to cancel out or reduce common magnetic field influences in order to magnify or make more pronounced local magnetic field distortions or influences caused by RSIs or other ferromagnetic objects.

Figure 7A:
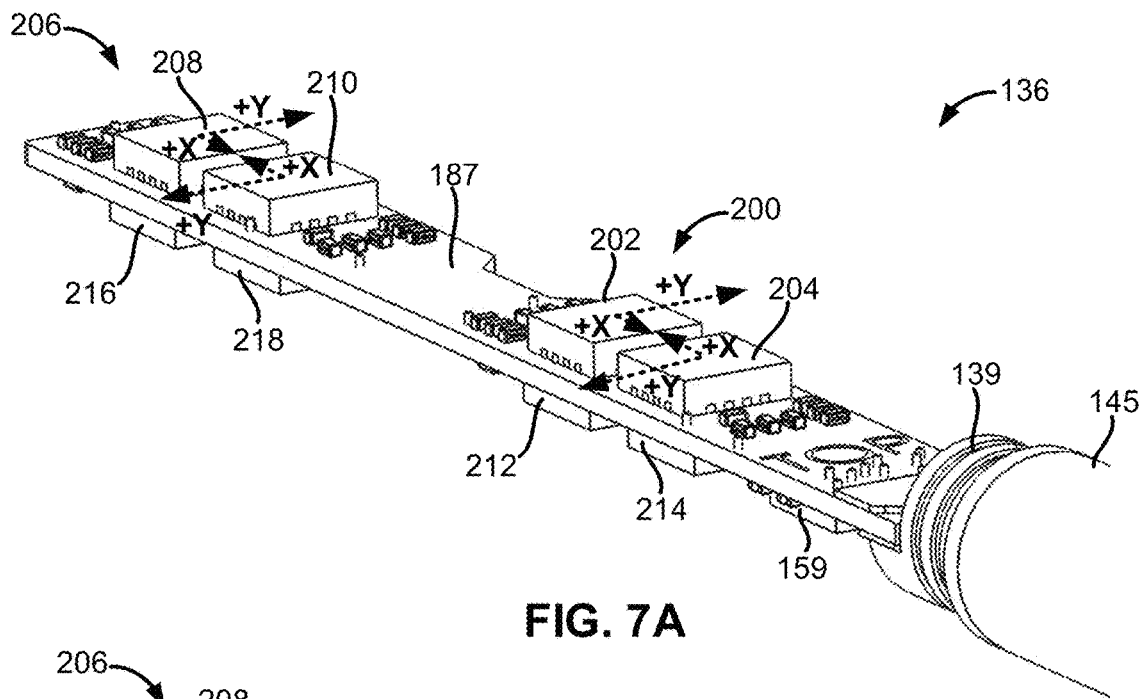
FIG. 7A illustrates an isometric view of another variation of the distal sensing portion of the metal detection device with the sensor housing removed.
Figure 7B:
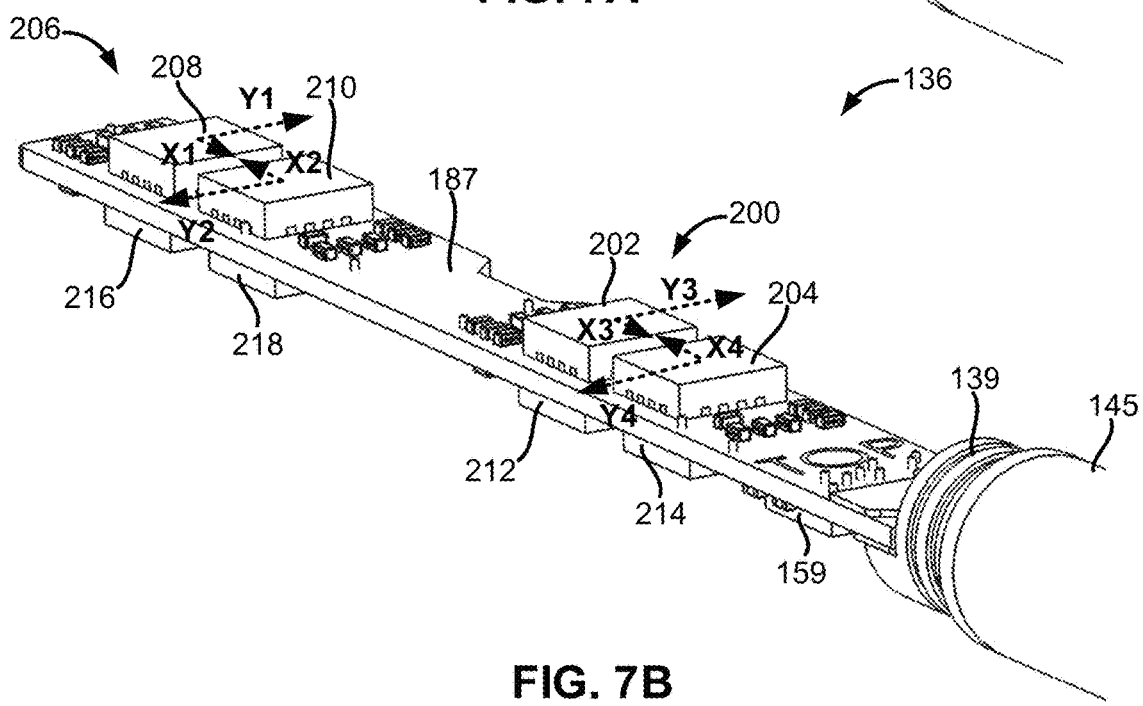
FIG. 7B illustrates a close-up isometric view of the distal sensing portion of FIG. 7A.

FIGS. 7A and 7B illustrate isometric views of another variation of the distal sensing portion 136 of the metal detection device with the sensor housing 141 removed. In this variation, the distal rigid PCB 163, the distal flex circuit 155, and the proximal rigid PCB 161 can be replaced by a singular rigid PCB 187. Also, in this variation, the magnetometers of the distal gradiometer 206 are not rotated with respect to the magnetometers of the proximal gradiometer 200.

As illustrated in FIGS. 7A and 7B, axes of the first proximal magnetometer 202 and the second proximal magnetometer 204 are either aligned or orthogonal to axes of the first distal magnetometer 208 and the second distal magnetometer 210. For example, the x-axes of the first distal magnetometer 208 and the second distal magnetometer 210 can be axially aligned with or positioned along the same axial plane as the x-axes of the first proximal magnetometer 202 and the second proximal magnetometer 204. Also, for example, the y-axes of the first distal magnetometer 208 and the second distal magnetometer 210 can be orthogonal to the x-axes of the first proximal magnetometer 202, the second proximal magnetometer 204, the first distal magnetometer 208, and the second distal magnetometer 210.

Although FIGS. 7A and 7B illustrate the circuit board of the distal sensing portion 136 as a singular rigid PCB 187, it is contemplated by this disclosure that the singular rigid PCB 187 can also be implemented as two rigid PCBs connected by a flexible circuit. In this variation, a fixation component.

The +x-axis of the first proximal magnetometer 202 can be oriented opposite the +x-axis of the second proximal magnetometer 204. The +y-axis of the first proximal magnetometer 202 can be oriented opposite the +y-axis of the second proximal magnetometer 204.

The +x-axis of the first distal magnetometer 208 can be oriented opposite the +x-axis of the second distal magnetometer 210 and the +y-axis of the first distal magnetometer 208 can be oriented opposite the +y-axis of the second distal magnetometer 210.

In some variations, the +x-axis of the second distal magnetometer 210 can be oriented opposite the +x-axis of the first proximal magnetometer 202. In these and other variations, the +y-axis of the second distal magnetometer 210 can be oriented opposite the +y-axis of the first proximal magnetometer 202.

FIG. 7B is the same figure as FIG. 7A except the +x-axes and the +y-axes are now replaced with labels to represent measurements obtained by the magnetometers along such axes. Magnetic field measurements obtained along the positive x-axis of the first distal magnetometer 208 is now referred to as X1, the positive y-axis of the first distal magnetometer 208 is now referred to as Y1, the positive x-axis of the second distal magnetometer 210 is now referred to as X2, the positive y-axis of the second distal magnetometer 210 is now referred to as Y2, the positive x-axis of the first proximal magnetometer 202 is now referred to as X3, the positive y-axis of the first proximal magnetometer 202 is now referred to as Y3, the positive x-axis of the second proximal magnetometer 204 is now referred to as X4, and the positive y-axis of the second proximal magnetometer 204 is now referred to as Y4.

Equations 1-17 below are equations devised by the applicant to calculate a differential signal from magnetic field measurements obtained from the first proximal magnetometer 202, the second proximal magnetometer 204, the first distal magnetometer 208, and the second distal magnetometer 210. The one or more processors of the microcontroller 185 can be programmed to execute instructions to calculate the differential signal using any of the equations below.

$$(X1+X2)-(X3+X4)+((Y1+Y2)-(Y3+Y4))= X1+X2-X3-X4+Y1+Y2-Y3-Y4$$
Equation 1 (also referred to as an on-axis local differential signal):

$$(X1+X4)-(X3+X2)+((Y1+Y4)-(Y3+Y2))=X1-X2-X3+X4+Y1-Y2-Y3+Y4$$
Equation 2 (also referred to as an on-axis global differential signal):

$$(X1+X2)-(X3+X4)+((Y1-Y2)-(Y3-Y4))=X1+X2-X3-X4+Y1-Y2-Y3+Y4$$
Equation 3 (also referred to as an on-axis Y local differential signal):

$$(X1+X4)-(X3+X2)+((Y1-Y4)-(Y3-Y2))=X-X2-X3+X4+Y1+Y2-Y3-Y4$$
Equation 4 (also referred to as an on-axis Y global differential signal):

$$(X1+X2)-(X3+X4)-((Y1+Y2)-(Y3+Y4))=X1+X2-X3-X4-Y1-Y2+Y3-Y4$$
Equation 5 (also referred to as an on-axis ortho local differential signal):

$$(X1+X4)-(X3+X2)-((Y1+Y4)-(Y3+Y2))=X1-X2-X3+X4-Y1+Y2+Y3-Y4$$
Equation 6 (also referred to as an on-axis ortho global differential signal):

$$(X1+Y2)-(X3+Y4)+((Y1+X2)-(Y3+X4))=X1+X2-X3-X4+Y1+Y2-Y3-Y4$$
Equation 7 (also referred to as an off-axis local differential magnetometer signal):

$$(X1+Y1)-(X2+Y2)+((Y3+X3)-(Y4+X4))=X1-X2+X3-X4+Y1-Y2+Y3-Y4$$
Equation 8 (also referred to as an off-axis super local differential signal):

$$(X1+Y4)-(X3+Y2)+((Y1+X4)-(Y3+X2))=X1-X2-X3+X4+Y1-Y2-Y3+Y4$$
Equation 9 (also referred to as an off-axis global differential signal):

$$(X1+Y3)-(X2+Y4)+((Y1+X3)-(Y2+X4))=X1-X2+X3-X4+Y1-Y2+Y3-Y4$$
Equation 10 (also referred to as an off-axis super global differential signal):

$$(X1+Y2)-(X3+Y4)-((Y1+X2)-(Y3+X4))=X1-X2+X3-X4-Y1+Y2+Y3-Y4$$
Equation 11 (also referred to as an off-axis ortho local differential signal):

$$(X1+Y4)-(X3+Y2)-((Y1+X4)-(Y3+X2))=X1+X2-X3-X4-Y1-Y2+Y3+Y4$$
Equation 12 (also referred to as an off-axis ortho global differential magnetometer signal):

$$(X1+Y1)-(X2+Y2)-((Y3+X3)-(Y4+X4))=X1-X2-X3+X4+Y1-Y2-Y3+Y4$$
Equation 13 (also referred to as an off-axis ortho super local differential signal):

$$(X1+Y3)-(X2+Y4)-((Y1+X3)-(Y2+X4))=X1-X2+X3-X4-Y1+Y2+Y3-Y4$$
Equation 14 (also referred to as off-axis ortho super global differential signal):

$$(X1-X2)-(X3-X4)+((Y1-Y2)-(Y3-Y4))=X1-X2-X3+X4+Y1-Y2-Y3+Y4$$
Equation 15 (also referred to as full global differential magnetometer signal):

$$(X1-X2)-(X3-X4)-((Y1-Y2)-(Y3-Y4))=X1-X2-X3+X4-Y1+Y2+Y3-Y4$$
Equation 16 (also referred to as full global ortho differential signal):

$$(-X1+X2)-(-X3+X4)+((-Y1+Y2)-(-Y3+Y4))=-X1+X2+X3-X4-Y1+Y2+Y3-Y4$$

Equation 17 (also referred to as inverse full global differential signal):

$$abs(X1-X1zero)+abs(X2-X2zero)+abs(X3-X3zero)+abs(X4-X4zero)+abs(Y1-Y1zero)+abs(Y2-Y2zero)+abs(Y3-Y3zero)+abs(Y4-Y4zero)$$

Equation 18 (also referred to as a zeroed-sum signal or a "soup" signal):

As shown above, Equations 2, 9, 13, and 15 produced the same final result despite the initial groupings being different. Moreover, equations 1 and 7 also produced the same net result.

Equation 18 is a zeroed sum (meaning the first reading or reference reading is subtracted from the signal going forward) of the absolute value of all of the magnetometers that were investigated as a potential high sensitivity candidate signal. The signal obtained from Equation 18 is also referred to as a "soup" signal. Since it does not have the advantage of subtracting common signals created from moving through earth's magnetic field lines this signal is much more susceptible to signals caused by moving through magnetic field lines in the room than Equations 2 or 6 which can have up to 4-5 times better needle detection to motion signal ratios.

One advantage of calculating the differential signal using the equations disclosed herein is that common magnetic field influences (e.g., the earth's magnetic field, magnetic field influences from medical equipment in the operating room, or field influences as a result of motion) are canceled out or reduced and local magnetic field distortions or influences are more noticeable and become a larger part of the overall signal.

It should be noted that the positive and negative signs in the aforementioned equations take into account that the magnetometers of the device 100 are configured in the manner shown in FIGS. 7A and 7B. For example, adding X1 and X2 is actually subtracting the two signals and subtracting X1 from X2 is actually adding the two signals.

In some circumstances, the differential signal calculated using equations 2, 9, 13, and 15 can be more pronounced or noticeable than the signals calculated using the other equations. In other circumstances, the differential signal calculated using equation 6 can be more pronounced or noticeable than the signals calculated using the other equations. Moreover, the differential signal calculated using equations 2, 9, 13, and 15 demonstrated nice cancellations of signals caused by moving through magnetic field lines in the operating room compared to more localized magnetic field distortions attributed to small stainless steel RSIs or other ferromagnetic objects.

The one or more processors of the microcontroller 185 can be programmed to execute further instructions to calculate the differential signal using more than one of the aforementioned equations and to switch between or cycle through different equations. For example, the one or more processors of the microcontroller 185 can be programmed to execute further instructions to calculate the differential signal using Equation 2 (the on-axis global differential signal) as well as Equations 3 (the on-axis Y local differential signal), 5 (the on-axis ortho local differential signal), and 6 (the on-axis ortho global differential signal).

Although reference is made above to each of the magnetometers or magnetic sensors comprising an x-axis (e.g., +x-axis) and a y-axis (e.g., +y-axis), it is contemplated by this disclosure that any reference to a x-axis (e.g., +x-axis) or a y-axis (e.g., +y-axis) can also refer to a single-axis magnetometer where the magnetometer or magnetic sensor only has an x-axis or y-axis. Therefore, any references to four two-axis magnetometers (e.g., a first proximal magnetometer 202, a second proximal magnetometer 204, a first distal magnetometer 208, and a second distal magnetometer 210) can also be applied to eight one-axis magnetometers (e.g., a first proximal magnetometer, a second proximal magnetometer, a third proximal magnetometer, a fourth proximal magnetometer, a first distal magnetometer, a second distal magnetometer, a third distal magnetometer, and a fourth distal magnetometer). In some implementations, the distal sensing portion 136 can comprise four gradiometers with each gradiometer having two one-axis magnetometers. For example, in the equations above, any references to X1, X2, X3, X4, Y1, Y2, Y3, and Y4 can also refer to one axis of each of a first magnetometer, a second magnetometer, a third magnetometer, a fourth magnetometer, a fifth magnetometer, a sixth magnetometer, a seventh magnetometer, and an either magnetometer, respectively.

A user or operator of the device 100 can also apply a user input (e.g., dialing the sensitivity wheel(s) 115 forward or backward) to instruct the one or more processors of the microcontroller 185 to switch between or cycle through different equations to calculate the differential signal.

Referring back to FIG. 6B, below is an additional equation (Equation 19) devised by the applicant to calculate a differential signal from magnetic field measurements obtained from the first proximal magnetometer 202, the second proximal magnetometer 204, the first distal magnetometer 208, and the second distal magnetometer 210 when the distal rigid PCB 163 is twisted or rotated by a twist angle (e.g., 45 degrees):

$$(X1+X2)-(X3+X4)+(\tfrac{1}{2}*Y1+\tfrac{1}{2}*Y2)-(Y3+Y4)+(\tfrac{1}{2}*Z1+\tfrac{1}{2}*Z2)=X1+X2-X3-X4+(\tfrac{1}{2}*Y1)+(\tfrac{1}{2}*Y2)-Y3-Y4+(\tfrac{1}{2}*Z1)+(\tfrac{1}{2}*Z$$

Equation 19 (also referred to as an on-axis distal twist local differential signal):

As will be discussed in more detail in the following sections, the one or more processors of the microcontroller 185 can be programmed to execute instructions to calculate the differential signal using any of the above equations.

The one or more processors of the microcontroller 185 can be programmed to execute instructions to calculate the differential signal using any combination of these equations at various points in time or other equations by themselves or in a sequence to evaluate local magnetic field distortions from different perspectives over time. At high speed these various perspectives can be combined to form an ensemble signal during use as small field distortions pass by the device.

The one or more processors of the microcontroller 185 can be programmed to execute further instructions to apply one or more filters (e.g., a high-pass filter and/or a low-pass filter) to the differential signal to obtain a detection signal. A smoothing function can also be applied to the detection signal.

In other variations, the one or more processors of the microcontroller 185 can be programmed to execute instructions to take the derivative or apply a derivative function to or take the derivative of the differential signal to obtain the detection signal.

The one or more processors of the microcontroller 185 can be programmed to execute further instructions to compare the detection signal against a sensitivity or detection threshold. The output component (e.g., speaker and/or LED(s)) can then be instructed to generate a user output (e.g., a beeping sound and/or a bright light) when the detection signal exceeds a sensitivity or detection threshold.

In some variations, whether a signal filter is applied or whether a derivative is taken is determined based on a sensitivity level set by the operator of the device 100 (e.g., surgeon or another medical professional). For example, the operator can dial the sensitivity wheel(s) 115 forward or in a distal direction until the sensitivity level or detection sensitivity of the device 100 is at level 8 or above. When the sensitivity level is at a level 8 or higher, the one or more processors of the microcontroller 185 can be programmed to execute instructions to apply one or more filters to the differential signal to obtain the detection signal but not take the derivative.

In another scenario, the operator can dial the sensitivity wheel(s) 115 backward or in a proximal direction until the sensitivity level or detection sensitivity of the device 100 is at level 7 or below. When the sensitivity level is at a level 7 or lower, the one or more processors of the microcontroller 185 can be programmed to execute instructions to take the derivative and apply one or more motion blocking algorithms to obtain the detection signal.

In any case, the detection signal is compared against a sensitivity or detection threshold and the output component(s) are instructed to generate the user output when the detection signal exceeds the sensitivity or detection threshold.

As shown in FIGS. 7A and 7B, the distal sensing portion 136 can further comprise one or more operational amplifiers coupled to the rigid PCB 187. The one or more operational amplifiers can be configured to amplify raw output signals from the various magnetometers before such signals are transmitted to the ADC 186 or an ADC component of the microcontroller 185 within the handle 102. For example, the operational amplifiers can comprise a first proximal operational amplifier 212, a second proximal operational amplifier 214, a first distal operational amplifier 216, and a second distal operational amplifier 218. The first proximal operational amplifier 212 can amplify a raw output signal of the first proximal magnetometer 202. The second proximal operational amplifier 214 can amplify a raw output signal of the second proximal magnetometer 204. The first distal operational amplifier 216 can amplify a raw output signal of the first distal magnetometer 208. The second distal operational amplifier 218 can amplify a raw output signal of the second distal magnetometer 210.

The first proximal operational amplifier 212 can be mounted on an underside of the circuit board (for example, the rigid PCB 187 or the proximal rigid PCB 161) carrying the first proximal magnetometer 202. The second proximal operational amplifier 214 can be mounted on an underside of the circuit board (for example, the rigid PCB 187 or the proximal rigid PCB 161) carrying the second proximal magnetometer 204. The first distal operational amplifier 216 can be mounted on an underside of the circuit board (for example, the rigid PCB 187 or the distal rigid PCB 163) carrying the first distal magnetometer 208. The second distal operational amplifier 218 can be mounted on an underside of the circuit board (for example, the rigid PCB 187 or the distal rigid PCB 163) carrying the second distal magnetometer 210.

In other variations, the operational amplifiers (e.g., the first proximal operational amplifier 212, the second proximal operational amplifier 214, the first distal operational amplifier 216, the second distal operational amplifier 218, or a combination thereof) can be mounted to the handle PCB 123 or a circuit board housed in another portion of the device 100.

Figure 7C:
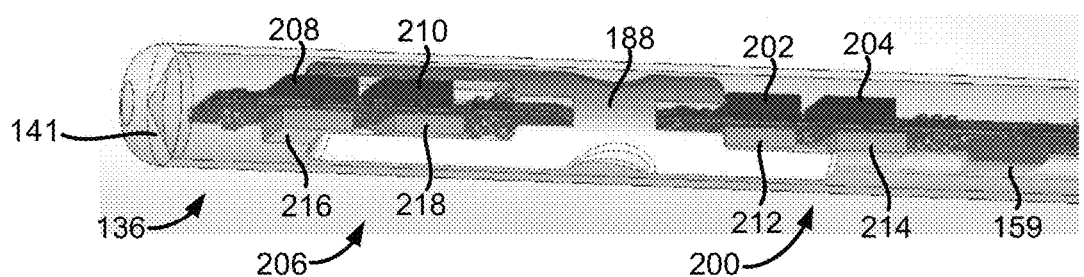
FIG. 7C illustrates another variation of the distal sensing portion with a sensor housing covering the distal sensing portion.

FIG. 7C illustrates a sensor housing 141 covering the distal sensing portion 136. As previously discussed, the sensor housing 141 can have a housing diameter 138 (see FIGS. 3A and 3B). The housing diameter 138 can be between about 3.0 mm to about 10.0 mm (e.g., about 5.0 mm).

FIG. 7C also illustrates that a fixation component 188 within the sensor housing 141 can secure the electronic components within the sensor housing 141 such that the electronic components (e.g., the magnetometers or op amps) do not become uncoupled or detached when the distal sensing portion 136 is bent toward the shaft or the shaft 131 is rotated.

In some variations, the fixation component 188 can be a polymeric holder or clip. In other variations, the fixation component 188 can be a clasp or other type of space filler.

As previously discussed, when the distal rigid PCB 163 is rotated, contorted, or otherwise rotated with respect to the proximal rigid PCB 161, another instance of the fixation component 188 can also be used to maintain the distal rigid PCB 163 in its rotated, contorted, or otherwise rotated configuration.

Figure 8A:
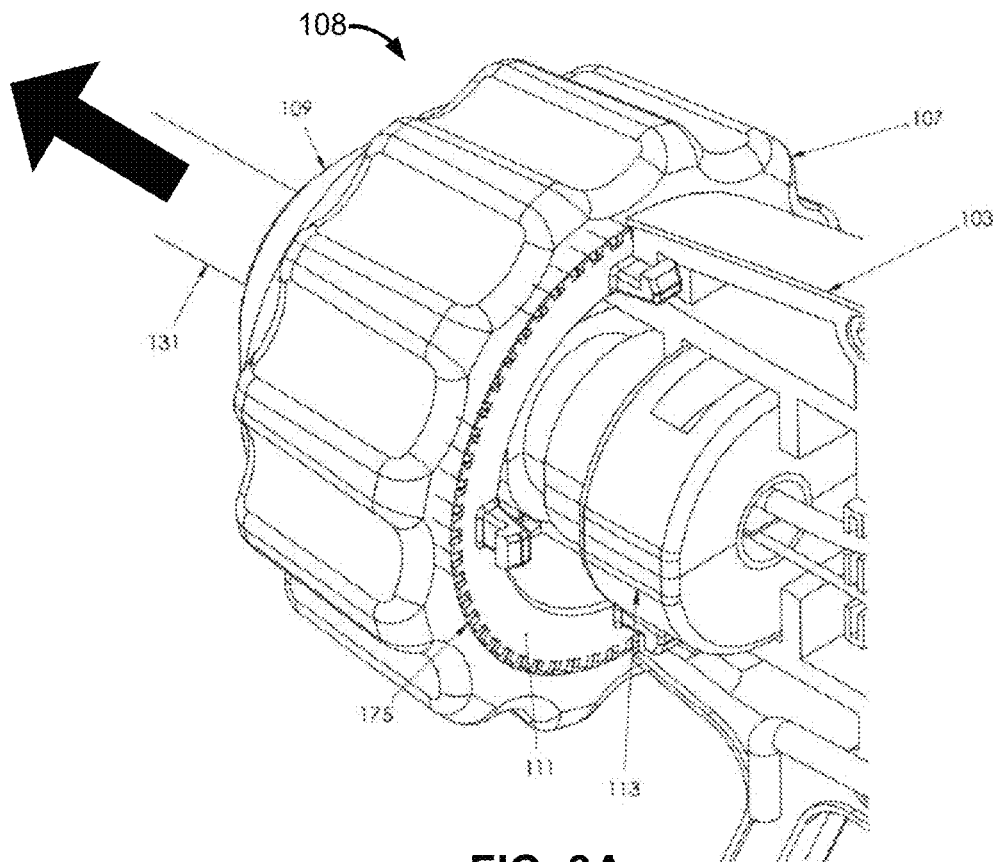
FIG. 8A illustrates a rear close-up isometric view of a clocking ring of the metal detection device in a locked position.
Figure 8B:
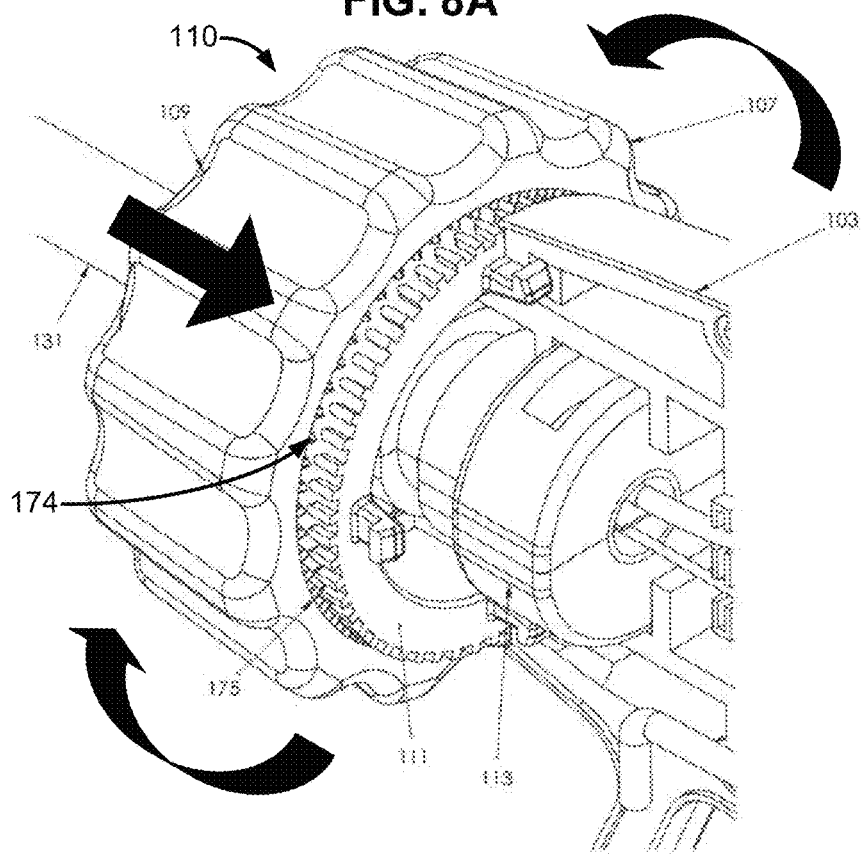
FIG. 8B illustrates a rear close-up isometric view of the clocking ring in an unlocked position.

FIGS. 8A and 8B illustrate rear close-up isometric views of the clocking ring 107 in a locked position 108 and an unlocked position 110, respectively. The left handle casing 101 is removed in FIGS. 8A-8B to better illustrate components within the handle 102. FIGS. 8A-8B illustrate that the shaft can be coupled to a tube boss 113 positioned within the handle 102. The clocking ring 107 can be rotationally fixed to the tube boss 113 such that rotation of the clocking ring 107 can rotate the tube boss 113 and, thereby, the shaft 131. The clocking ring 107 can be defined by grooves or furrows to allow an operator to more easily translate and rotate the clocking ring 107.

The locking ring 111 can be translationally and rotationally fixed to the left handle casing 101 and the right handle casing 103 via snap clips or other fasteners. The locking ring 111 can comprise a plurality of locking splines 175 defined around the circumference of the locking ring 111. The clocking ring 107 can comprise a plurality of reciprocal locking splines 174 for engaging with the locking splines 175 on the locking ring 111.

As shown in FIG. 8A, the clocking ring 107 can be positioned over the locking ring 111 when the clocking ring 107 is in a locked position 108. The locking splines 175 on the locking ring 111 can interlock with the reciprocal locking splines 174 of the clocking ring 107 to inhibit rotation of the clocking ring 107.

The clocking ring 107 can be pushed or slid distally forward into an unlocked position 110. The clocking ring 107 can be pushed or slid distally in a direction of the shaft 131 as shown by the enlarged arrow in FIG. 8A. For example, an operator (e.g., a surgeon or other medical professional) can hold the handle 102 with one hand and push or slide the clocking ring 107 forward with the other hand.

FIG. 8B illustrates that the reciprocal locking splines 174 of the clocking ring 107 can be disengaged from the locking splines 175 of the locking ring 111 when the clocking ring 107 is in the unlocked position 110. The clocking ring 107 can be rotated, in a clockwise direction or counterclockwise direction, when in the unlocked position 110. Rotating the clocking ring 107 can rotate the tube boss 113 and the shaft 131 (as well as the flexible portion 145 and the distal sensing portion 136).

Once the operator has rotated the clocking ring 107 to the desired rotational position, the operator can pull or slide the clocking ring 107 back onto the locking ring 111 to lock the clocking ring 107 in place. The operator can pull or slide the clocking ring 107 back onto the locking ring 111 in a direction of the handle proximal end as shown by the enlarged arrow in FIG. 8B. The operator can continue to unlock and lock the clocking ring 107 to achieve a desired rotation of the shaft 131.

The operator can rotate the clocking ring 107 while simultaneously squeezing the trigger 105 to bend the flexible portion 145. The ability to rotate the shaft 131 while also bending the flexible portion 145 can allow an operator to probe various body cavities or lumens and sweep behind or around organs with minimal movement of the user's hands. One technical advantage of the device 100 is the multiple degrees of freedom afforded by the control mechanism disclosed herein.

Figure 8C:
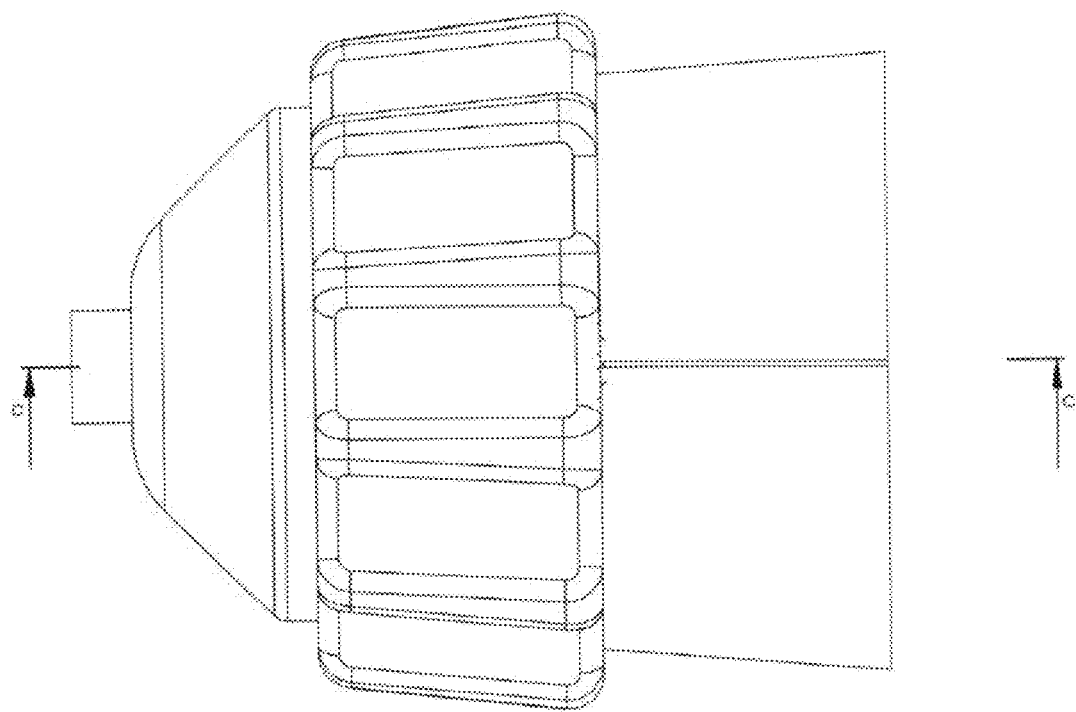
FIG. 8C illustrates a close-up side view of the clocking ring in the locked position.
Figure 8D:
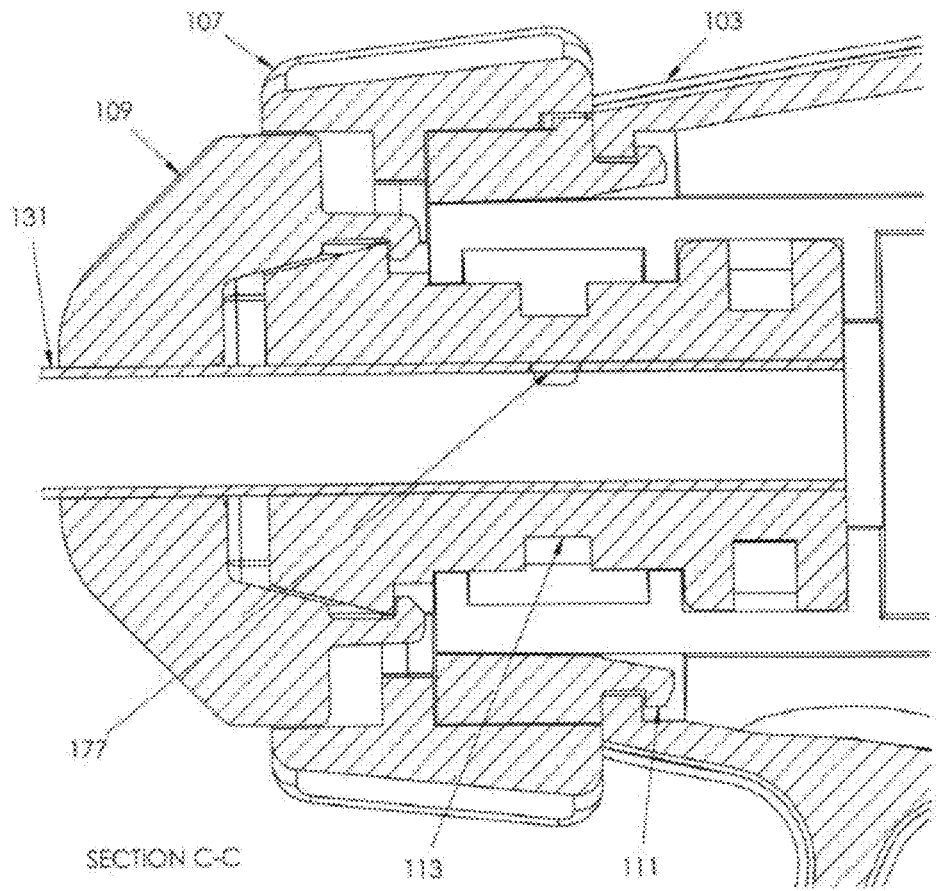
FIG. 8D illustrates a sectional view of the clocking ring in the locked position along section C-C shown in FIG. 8C.
Figure 8E:
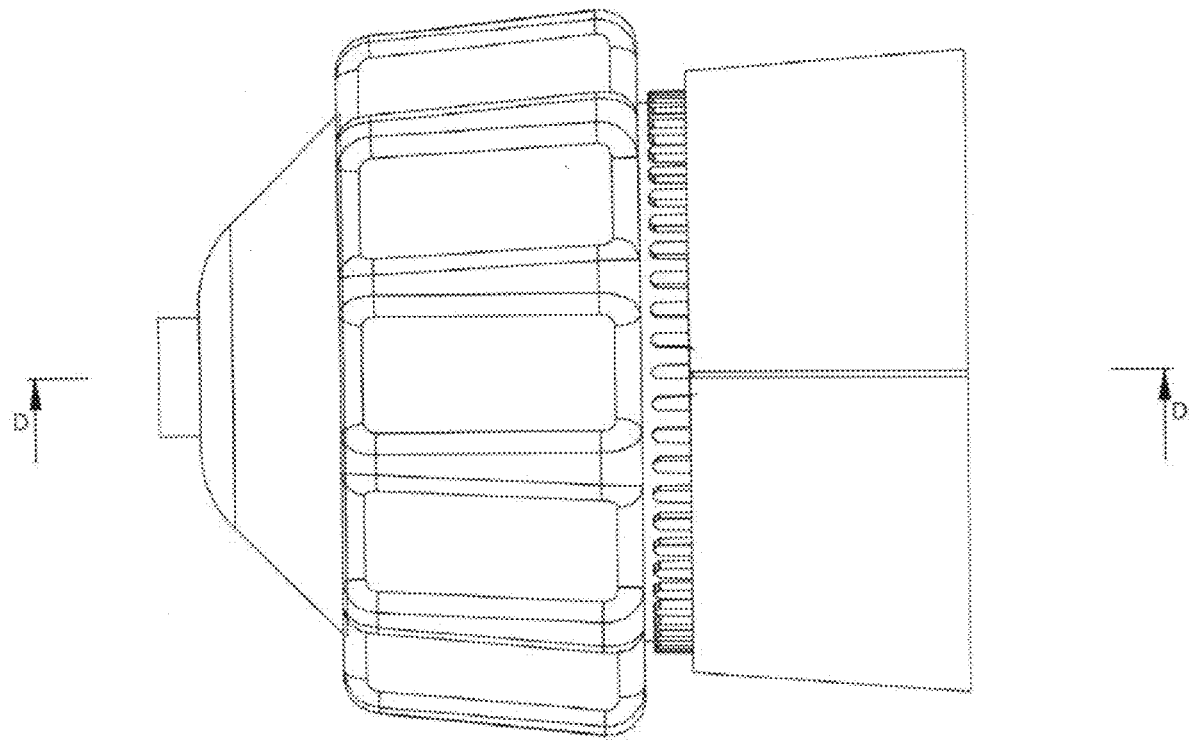
FIG. 8E illustrates a close-up side view of the clocking ring in the unlocked position.
Figure 8F:
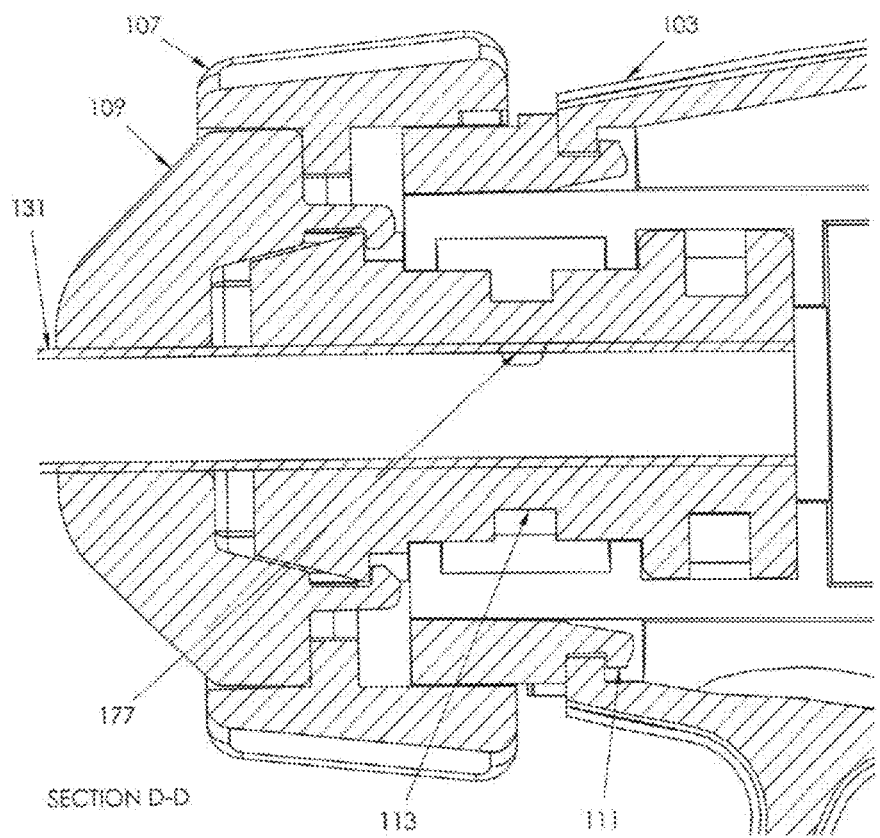
FIG. 8F illustrates a sectional view of the clocking ring in the unlocked position along section D-D shown in FIG. 8E.

FIG. 8C illustrates a close-up side view of the clocking ring 107 in the locked position 108 and FIG. 8D illustrates a sectional view of the clocking ring 107 in the locked position 108 along section C-C shown in FIG. 8C. FIG. 8E illustrates a close-up side view of the clocking ring 107 in the unlocked position 110 and FIG. 8F illustrates a sectional view of the clocking ring 107 in the unlocked position 110 along section D-D shown in FIG. 8E. The spring tube 137, test rod 133, and flexible circuits within the shaft 131 are not shown in FIGS. 8C-8F for ease of viewing.

FIGS. 8C-8F illustrate that a nose cap 109 can be coupled to the tube boss 113 within the handle 102 via snap clips or other fasteners. The outer surface of the nose cap 109 can serve as a bearing surface or receiving surface for the clocking ring 107 as the clocking ring 107 is pushed distally or pulled proximally. The nose cap 109 can also serve as a bearing surface for the clocking ring 107 as the clocking ring 107 is rotated by the operator.

FIGS. 8D and 8F also illustrate that a shaft locking boss 177 can extend from a radially inner surface of the tube boss 113 into a mating hole on the shaft 131. This can allow the tube boss 113 to be rotationally and translationally coupled to the shaft 131.

Figure 8G:
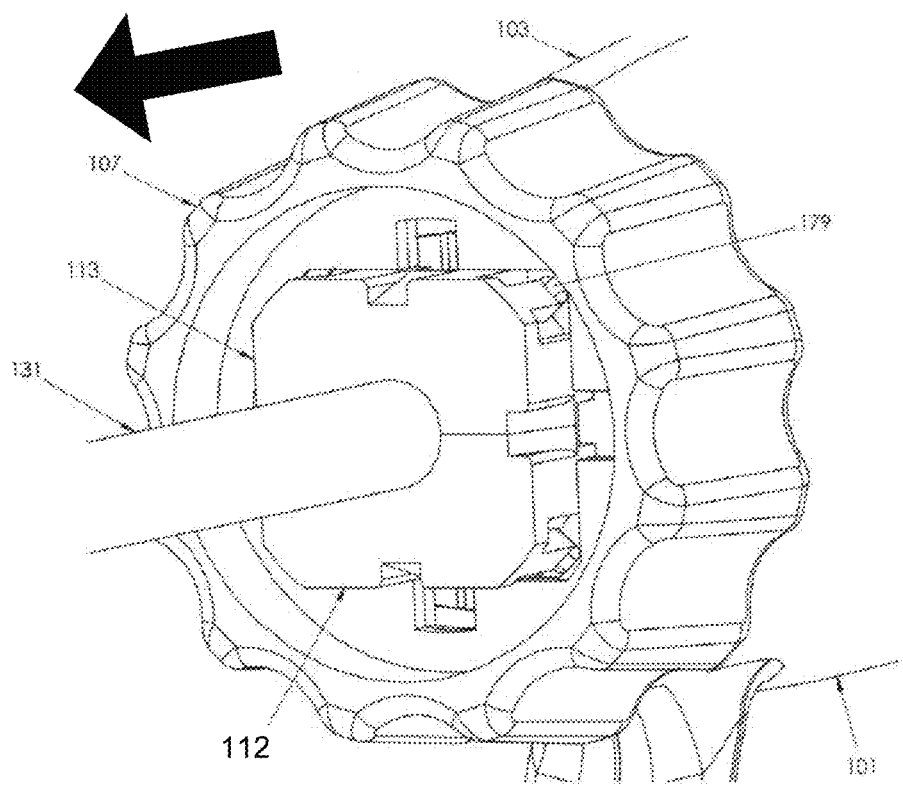
FIG. 8G illustrates a front close-up isometric view of the clocking ring in the locked position with a nose cap removed.
Figure 8H:
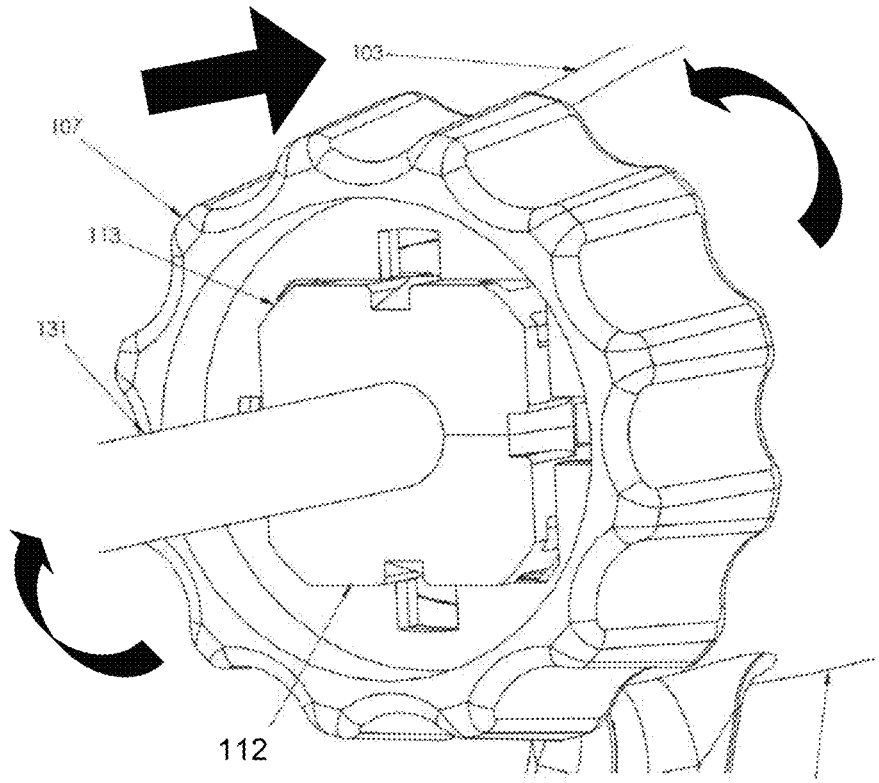
FIG. 8H illustrates a front close-up isometric view of the clocking ring in the unlocked position with the nose cap removed.

FIGS. 8G and 8H illustrate front close-up isometric views of the clocking ring 107 in the locked position 108 and the unlocked position 110, respectively, with the nose cap 109 removed for use of viewing. FIGS. 8G and 8H illustrate that a distal end 112 of the tube boss 113 can comprise a polygonal feature, such as a substantially square-shaped block, that can mate with a square-shaped cutout (or another polygonal-shaped cutout) in the clocking ring 107 in order to rotationally couple the clocking ring 107 to the tube boss 113.

The tube boss 113 can comprise a number of clocking ring detents 179 that can interfere with reciprocal features on an inner surface of the clocking ring 107. The clocking ring detents 179 can prevent the clocking ring 107 from translating distally (i.e., from being unlocked) without sufficient force applied by an operator (e.g., a surgeon or other medical professional). Once sufficient distal force is applied to the clocking ring 107, the clocking ring detents 179 can deform or deflect and allow the clocking ring 107 to translate distally (as shown by the enlarged arrow in FIG. 8G) and become free to rotate.

FIG. 8H illustrates that the clocking ring 107, in its unlocked position 110, can be rotated in a clockwise or counterclockwise rotational direction. When the clocking ring 107 is in the unlocked position 110, the clocking ring detents 179 can be positioned behind or proximal to the interfering features on the clocking ring 107. When the operator desires to lock the shaft 131 into place, the operator can apply sufficient force to pull the clocking ring 107 backward or proximally in a direction of the enlarged arrow (e.g., in a direction of the handle proximal end) such that the clocking ring detents 179 once again engages with the interfering features on the clocking ring 107.

Figure 9A:
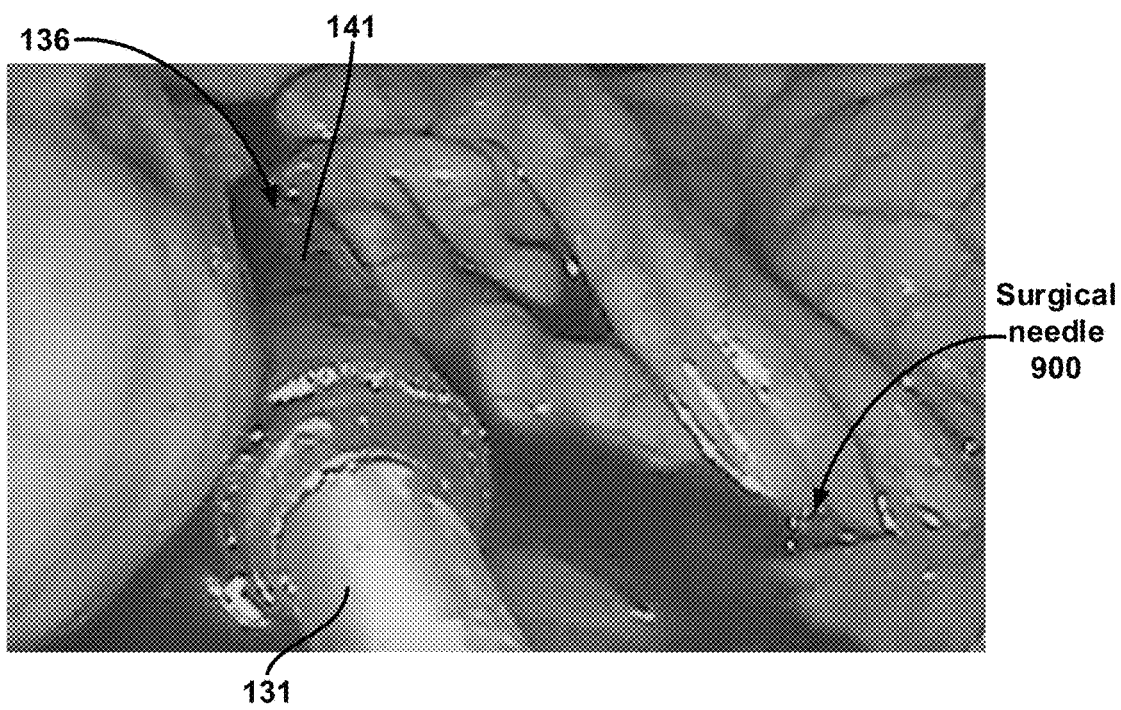
FIG. 9A is a black-and-white image of a variation of the metal detection device used to detect a surgical needle in a porcine bowel.
Figure 9B:
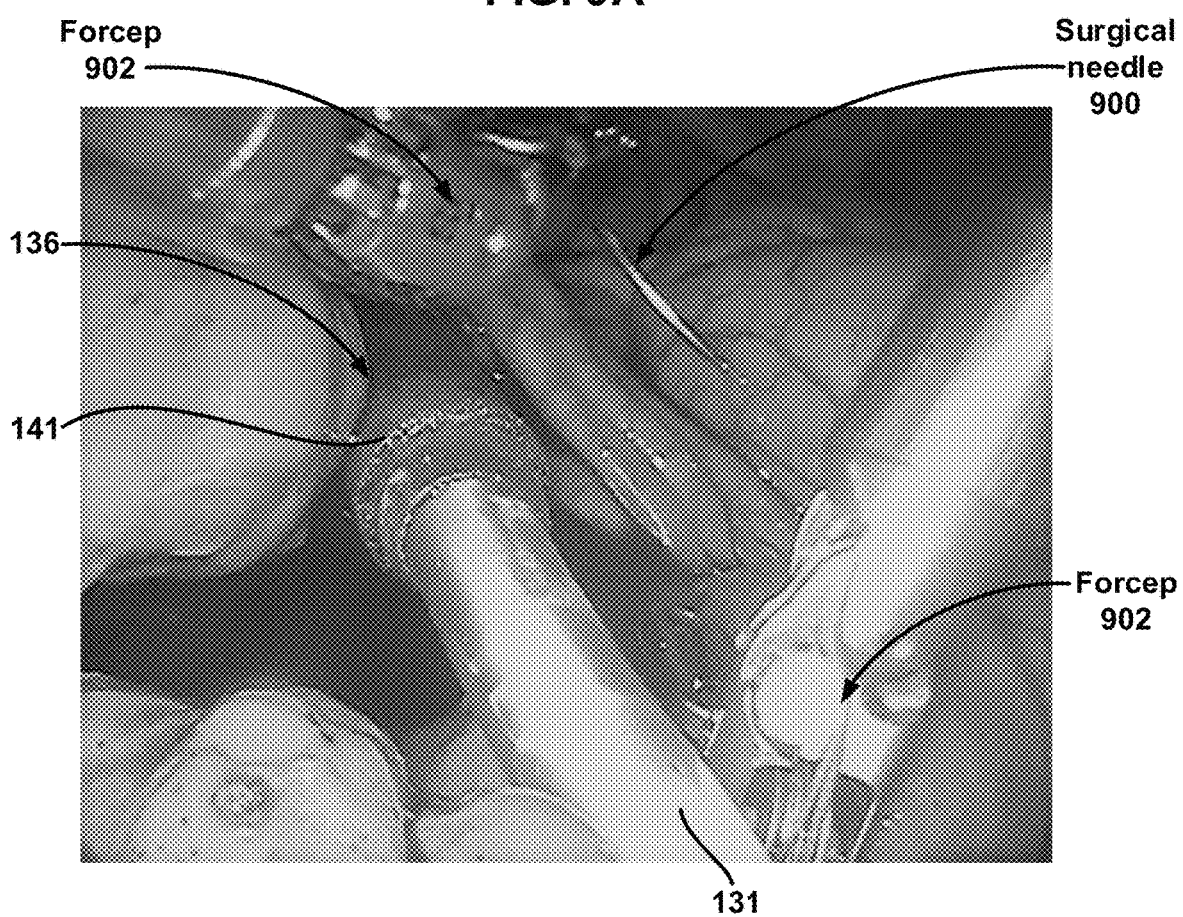
FIG. 9B is a black-and-white image of forceps used to retrieve the surgical needle upon detection by the metal detection device.

FIG. 9A is an image of the metal detection device 100 used to detect a surgical needle 900 within a body cavity of a subject. FIG. 9B is an image of forceps 902 used to retrieve the surgical needle 900 upon detection by the metal detection device 100. FIGS. 9A and 9B illustrate that upon detection by the device 100, forceps 902 or other surgical graspers can be used to retrieve the surgical needle 900 (or other RSI) from the body of the subject.

In other variations not shown in the figures, the device 100 can comprise one or more permanent magnets, electromagnets, or a combination thereof. The one or more permanent magnets, electromagnets, or a combination thereof can be positioned within the distal sensing portion 136. The one or more permanent magnets, electromagnets, or a combination thereof can be positioned along a segment of the shaft 131. In these variations, detection of the RSI or ferromagnetic object can be conducted with the electromagnet powered off or demagnetized. Once the RSI or other ferromagnetic objected is detected by the device 100, an operator can turn on or magnetize the electromagnet and use the electromagnet and/or permanent magnet to magnetically attract the RSI or ferromagnetic object.

The electromagnet can have a variable field strength. In some variations, an operator can adjust the field strength of the electromagnet between one or more strength levels based on the size or magnetism of the RSI or ferromagnetic object.

Figure 10A:
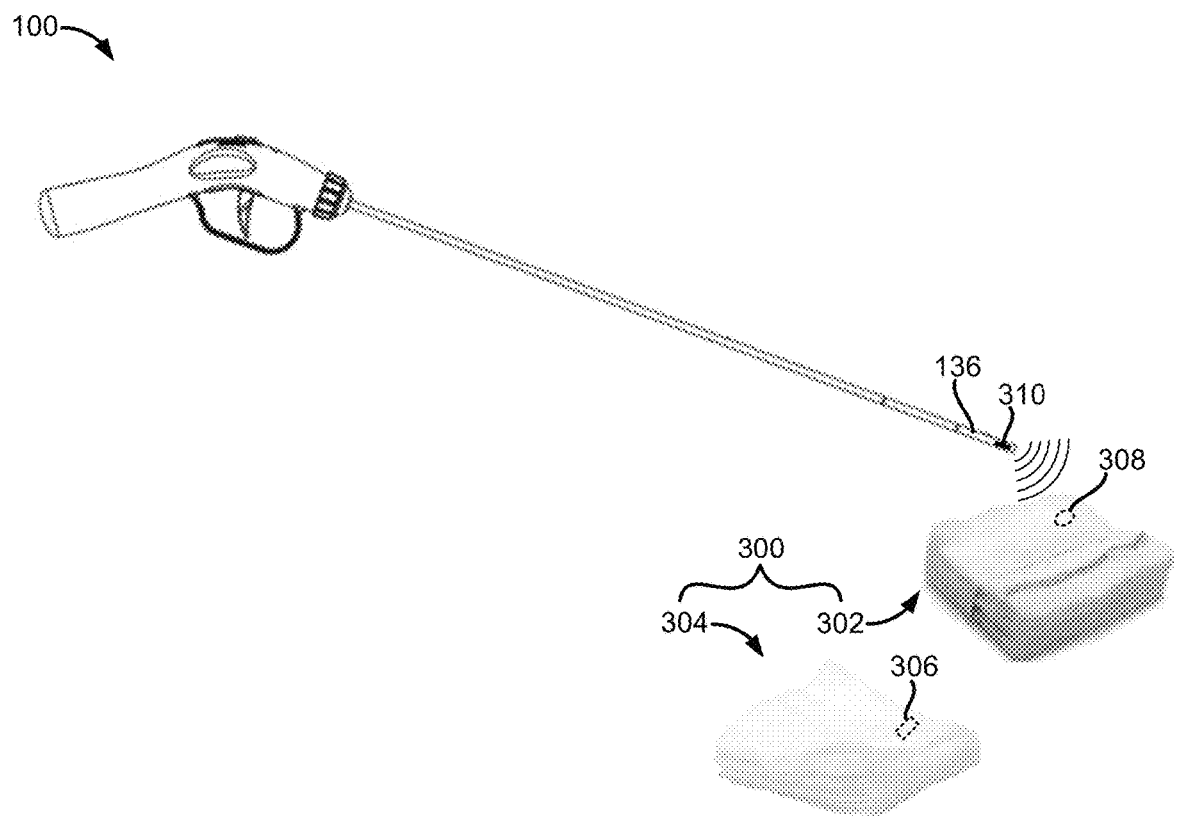
FIG. 10A illustrates a variation of the metal detection device used to detect RFID-tagged sponges or sponges having one or more metallic markers within a body of a patient.

FIG. 10A illustrates that the metal detection device 100 disclosed herein can also be used to undertake intracorporeal detection of surgical sponges 300 including RFID-tagged sponges 302 and metallic-marked sponges 304 tagged with one or more metallic markers 306. Surgical sponges 300 often rank highest among all RSIs. In one study, sponge products accounted for 68% of all RSIs. See Cima, Robert R., et al. "Using a data-matrix-coded sponge counting system across a surgical practice: impact after 18 months." The Joint Commission Journal on Quality and Patient Safety 37.2 (2011): 51-AP3.

The metallic-marked sponges 304 can be tagged or otherwise embedded with one or more ferromagnetic metallic markers 306 or ferromagnetic metallic tags. For example, the metallic-marked sponges 304 can comprise ferromagnetic beads, wires, threads, or a combination hereof embedded or interwoven with fabric or other material making up at least part of the sponge.

The RFID-tagged sponges 302 can comprise an RFID tag 308 embedded within one or more layers of the sponge. The RFID tag 308 can be a passive RFID transponder. In other variations, the RFID tag 308 can be an active RFID transponder having its own power source.

As shown in FIG. 10A, the device 100 can comprise an RFID reader 310 within the distal sensing portion 136. The distal sensing portion 136 can comprise the various magnetometers and other electronic components disclosed herein in addition to the RFID reader 310. The RFID reader 310 can be configured to read one or more RFID tags 308 within the RFID-tagged sponges 302. The RFID reader 310 can be electrically coupled to or be in electrical communication with the microcontroller 185 such that the microcontroller 185 can instruct the RFID reader 310 to transmit an interrogating pulse to the RFID tag(s) 308 to obtain identifying information or data concerning the RFID-tagged sponges 302.

The RFID reader 310 can allow the device 100 to account for missing or retained RFID-tagged sponges 302 and to locate such RFID-tagged sponges 302 intraoperatively within a body cavity of the patient.

In these and other variations, the device 100 can also be used to locate misplaced or retained metallic-marked sponges 304 using the magnetometers and magnetic detection algorithms disclosed herein. For example, an operator or medical professional can adjust the sensitivity of the device 100 using the sensitivity wheel(s) 115 until the device 100 generates a user output to indicate the presence of a metallic-marked sponge 304 within a body cavity of the patient.

Figure 10B:
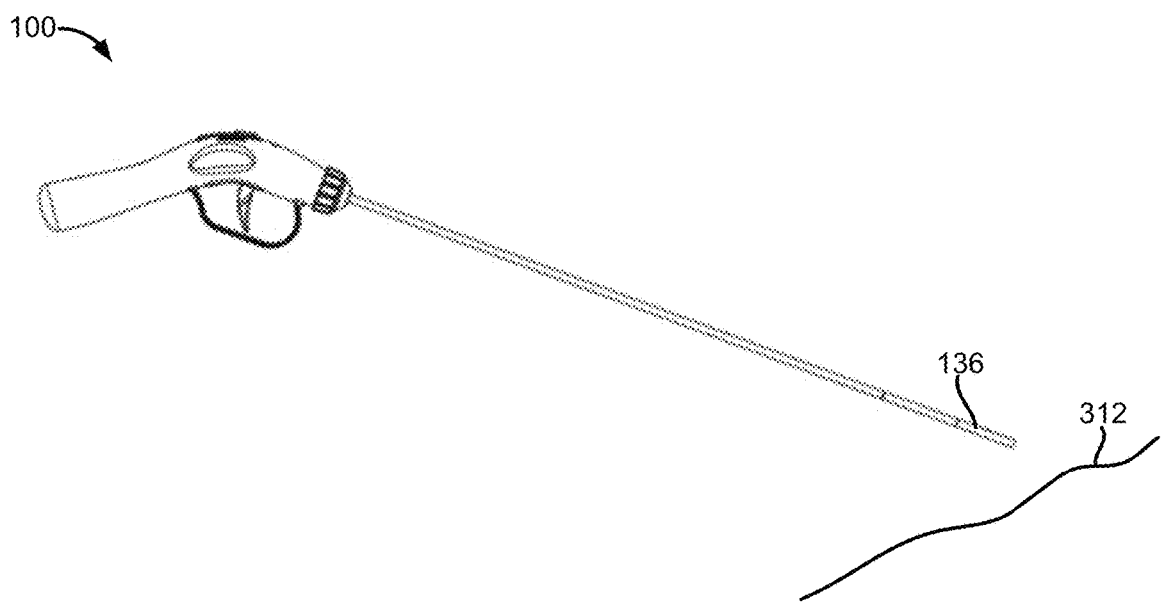
FIG. 10B illustrates the metal detection device used to detect wires within the body of a patient.

FIG. 10B illustrates that the metal detection device 100 disclosed herein can also be used to undertake intracorporeal detection of ferromagnetic wires 312 such as surgical wires, guidewires, intravascular wires, or a combination thereof. In these and other variations, the device 100 can also be used to locate or detect ferromagnetic catheters, sheaths, tubes, clips, other medical instruments, or fragments/segments thereof.

Moreover, the metal detection device 100 disclosed herein can also be used to undertake intracorporeal detection of non-ferromagnetic wires, catheters, sheaths, tubes, clips, or other medical instruments that have been tagged with a ferromagnetic tag or plate.

Figure 11A:
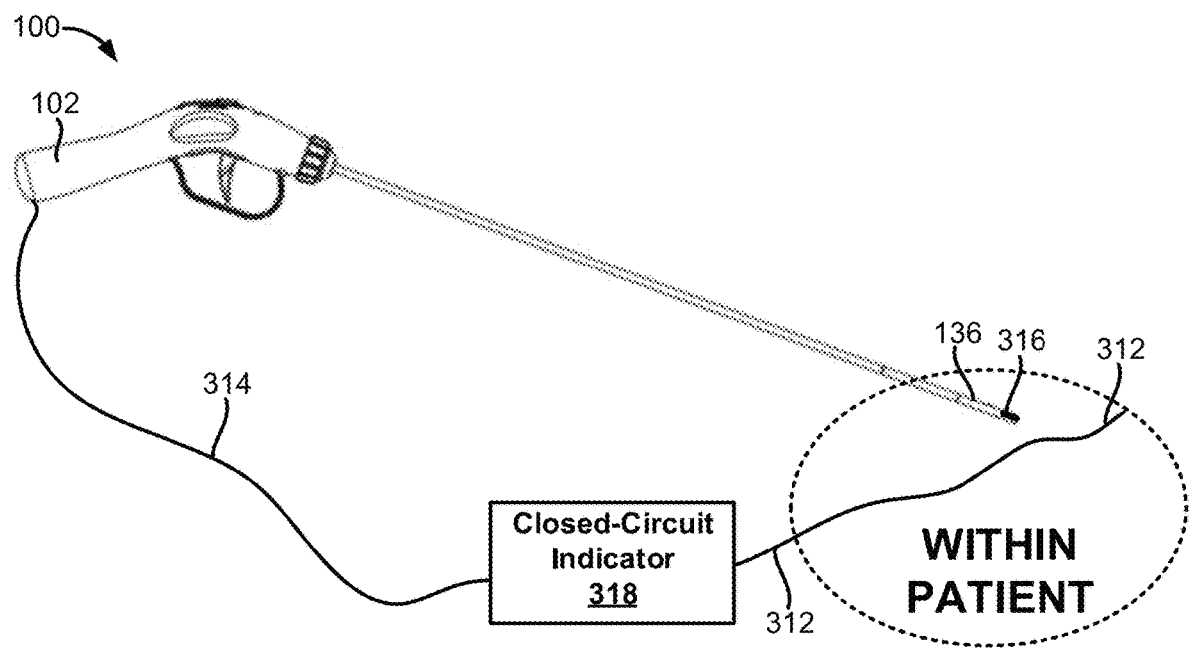
FIG. 11A illustrates a variation of the metal detection device used to detect a wire within a body of a patient through a closed-circuit detection mechanism.

FIG. 11A illustrates another variation of the metal detection device 100 comprising a linking cable 314 extending from the device 100 (e.g., a proximal end or handle 102 of the device 100) and electrically coupled to a closed-circuit indicator 318 disposed outside of the body of the patient. A proximal end of a wire 312, such as a ferromagnetic guidewire or surgical wire, can be extended outside or otherwise exit the body of the patient and be electrically coupled to the closed-circuit indicator 318. The distal end of the wire or a segment of the wire 312 can be within the body of the patient. As shown in FIG. 11A, the device 100 can comprise a conductive element 316, such as a conductive patch, at a distal end of the device 100. For example, the conductive element 316 can extend from the distal sensing portion 136 out of the sensor housing 141 or be disposed along the shaft 131. The conductive element 316 can be in electrically coupled to or be in electrical communication with the linking cable 314.

When the conductive element 316 makes contact with the wire 312 within the body of the patient, the closed-circuit indicator 318 can generate a signal or output (e.g., a sound or auditory instruction, a light or light pattern, or a combination thereof) to indicate that a closed circuit is achieved by the conductive element 316 making contact with the wire 312 within the body of the patient. This mechanism can be used to detect the location of the wire 312 within the patient. This is especially important when the wire 312 is not visible to a surgeon or other medical professional directly or via endoscopy.

Figure 11B:
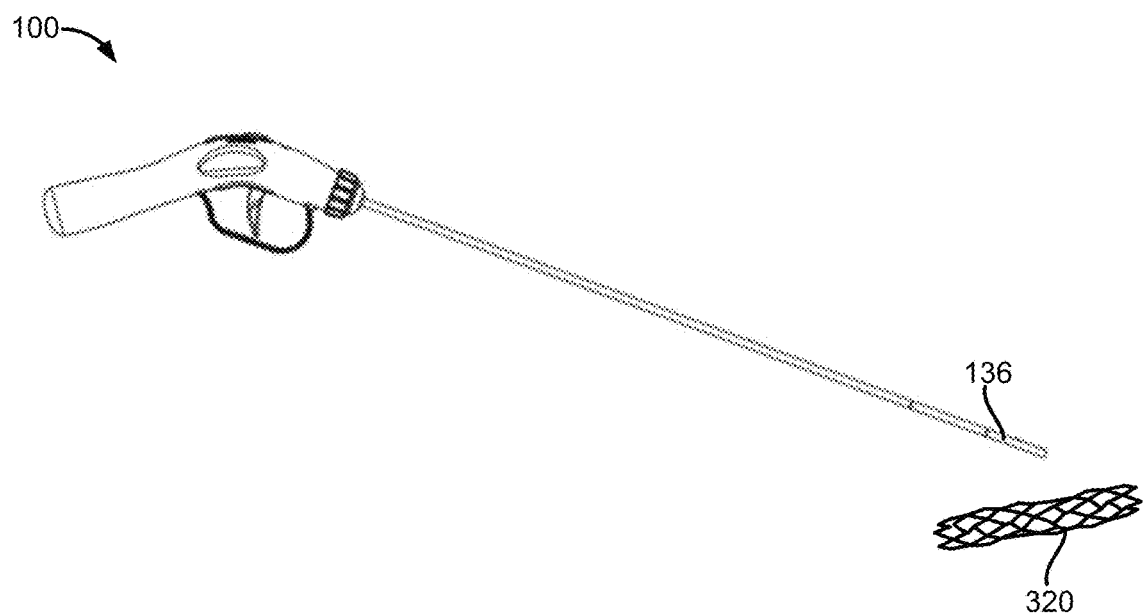
FIG. 11B illustrates the metal detection device used to detect a stent or other implantable scaffold within a body of a patient.

FIG. 11B illustrates that the metal detection device 100 disclosed herein can also be used to undertake intracorporeal detection of ferromagnetic stents 320 or other supporting scaffolds. The device 100 can be used to detect or verify an implantation site of the stent 320 or supporting scaffold. The device 100 can also be used to detect a non-ferromagnetic stent 320 or supporting scaffold coated with a metallic coating or tagged with one or more metallic markers.

In some variations, where ferromagnetic or metallic-marked wires, stents, or scaffolds are used to support organs, lumens, or cavities of a patient, the device 100 can be used to not only detect such wires, stents, or scaffolds (e.g., for possible removal or inspection) but also to detect or pinpoint the location of such organs, lumens, or cavities for further procedures.

Figure 12:
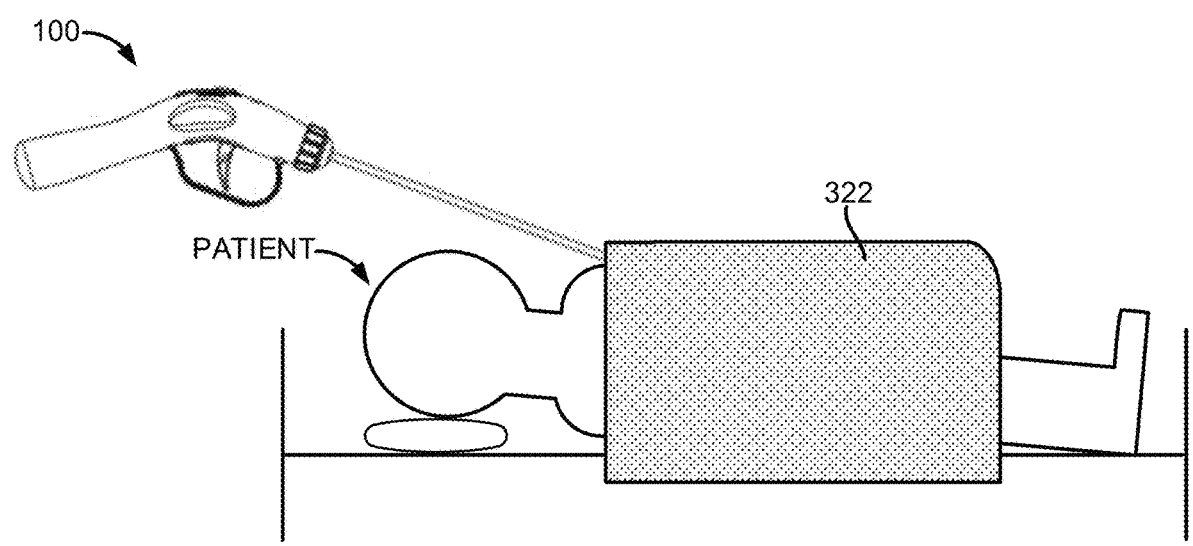
FIG. 12 illustrates a variation of a magnetic blanket or shield used to at least partially cover or shield a body cavity or body part of a patient when the metal detection device is undertaking magnetic detection within the body cavity or body part.

FIG. 12 illustrates that the metal detection device 100 can be used when the body cavity or body part of the patient is at least partially covered, shielded, or ensconced by a magnetic blanket 322 or magnetic shield. In some variations, the magnetic blanket 322 can comprise a plurality of magnets embedded or otherwise disposed within layers of the blanket.

For example, the magnetic blanket 322 can be used to cover an abdomen of the patient when the device 100 is used to detect RSIs or retained sharps within the abdomen of the patient.

The magnetic blanket 322 or shield can be used to create a controlled magnetic environment. The magnetic blanket 322 or shield can also be used to enhance certain signals or magnetic field distortions generated by certain RSIs (e.g., RFID-tagged sponges 302) once the distal sensing portion 136 of the device 100 is within the body cavity of the patient and the detection sensitivity of the device is adjusted such that the magnetic field distortion created by the magnetic blanket 322 or shield is accounted for.

The magnetic blanket 322 or shield can be used to at least partially cover, shield, or ensconce a body cavity or body part of the patient when the device 100 is used to undertake intracorporeal detection of RSIs, implants, surgical tools, or a combination thereof within the body cavity or body part. For example, the magnetic blanket 322 or shield can be used to at least partially cover, shield, or ensconce a body cavity or body part of the patient when the device 100 is used to undertake intracorporeal detection of needles, sponges 300, wires 312, stents 320 or other scaffolds, ferromagnetic or metallically-marked catheters, sheaths, or other surgical equipment, or parts or combinations thereof.

Alternatively or additionally, the magnetic blanket 322 can be used to wrap certain needles, wires, or other tools before surgery in order to magnetize such needles, wires, or tools to make such needles, wires, or tools more easily detectable by the device 100.

Figure 13:
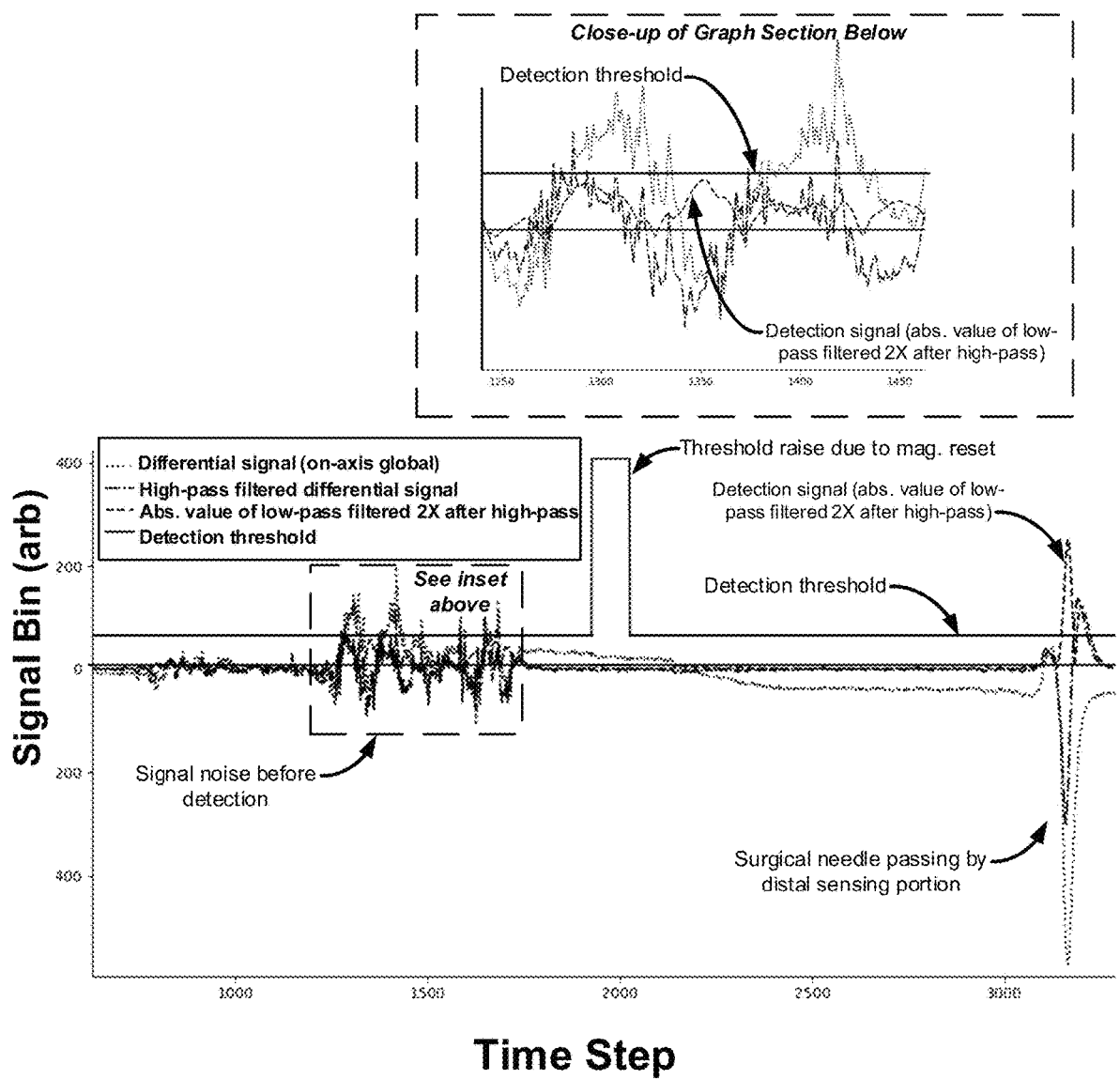
FIG. 13 is a signal diagram illustrating the distal sensing portion of the metal detection device passing over a surgical needle.

FIG. 13 is a signal diagram illustrating the distal sensing portion 136 of the device 100 passing over a surgical needle (e.g., a 5-0.13 mm surgical needle). The device 100 can be operating in a high speed and high sensitivity mode in the scenario shown in FIG. 13. In this mode, the sensitivity wheel(s) 115 can be dialed forward or distally such that the sensitivity level is above a starting default level (e.g., level 8, 9, 10, or 11). In this mode, the one or more processors of the microcontroller 185 can be programmed to execute instructions to apply one or more signal filters (e.g., a high-pass filter, a low-pass filter, or a combination thereof) to the differential signal to obtain the detection signal. Moreover, each time step in FIG. 13 can represent approximately 1.5 milliseconds.

For example, the one or more processors of the microcontroller 185 can be programmed to execute instructions to first calculate a differential signal from magnetic field measurements obtained from the first proximal magnetometer 202, the second proximal magnetometer 204, the first distal magnetometer 208, and the second distal magnetometer 210. More specifically, the one or more processors of the microcontroller 185 can be programmed to execute instructions to calculate the differential signal using any of the equations 1-18 above. In the scenario shown in FIG. 13, the differential signal is calculated using equation 2 (also referred to as an on-axis global differential signal).

The one or more processors of the microcontroller 185 can be programmed to execute further instructions to apply a high-pass filter to the differential signal (e.g., the on-axis global differential signal). The high-pass filter can get rid of low-frequency noise in the differential signal. For example, the high-pass filter can get rid of drift and offset and bring the average signal back to zero.

The one or more processors of the microcontroller 185 can be programmed to execute additional instructions to apply a number of low-pass filters to the high-pass filtered signal. For example, the one or more processors of the microcontroller 185 can be programmed to execute additional instructions to apply a second order low-pass filter (also known as a two-pole filter) to get rid of high-frequency noise in the high-pass filtered signal. The low-pass filter or second order filter (or two-pole filter) can more aggressively cut off high frequency noise. In some variations, the high-pass filter can have a cutoff of 5.5 Hz and the low-pass filter can have a cutoff of 10 Hz.

The one or more processors of the microcontroller 185 can be programmed to execute further instructions to take the absolute value of the low-pass filtered signal and to apply a smoothing function (smoothPoints=10) to the low-pass filtered signal to obtain the detection signal.

The one or more processors of the microcontroller 185 can be programmed to execute additional instructions to compare the detection signal against a sensitivity threshold or detection threshold. Moreover, the one or more processors of the microcontroller 185 can be programmed to execute further instructions to instruct the output component (e.g., the speaker and/or LED lights) to generate a user output (e.g., a beeping sound, a flashing light, a light of increasing intensity, or a combination thereof) when the detection signal exceeds the sensitivity or detection threshold.

As shown in FIG. 13, the detection signal exceeds the detection threshold when the distal sensing portion 136 is passed over the surgical needle. The inset in FIG. 13 also illustrates that signal noise before the detection is addressed by the filter steps which produces a more accurate detection signal that would not result in false positive detection.

FIG. 13 also illustrates that the sensitivity level of the device 100 can be decreased and the sensitivity or detection threshold can be automatically increased when the magnetometers are periodically reset to filter out any settling events or level changes.

Figure 14:
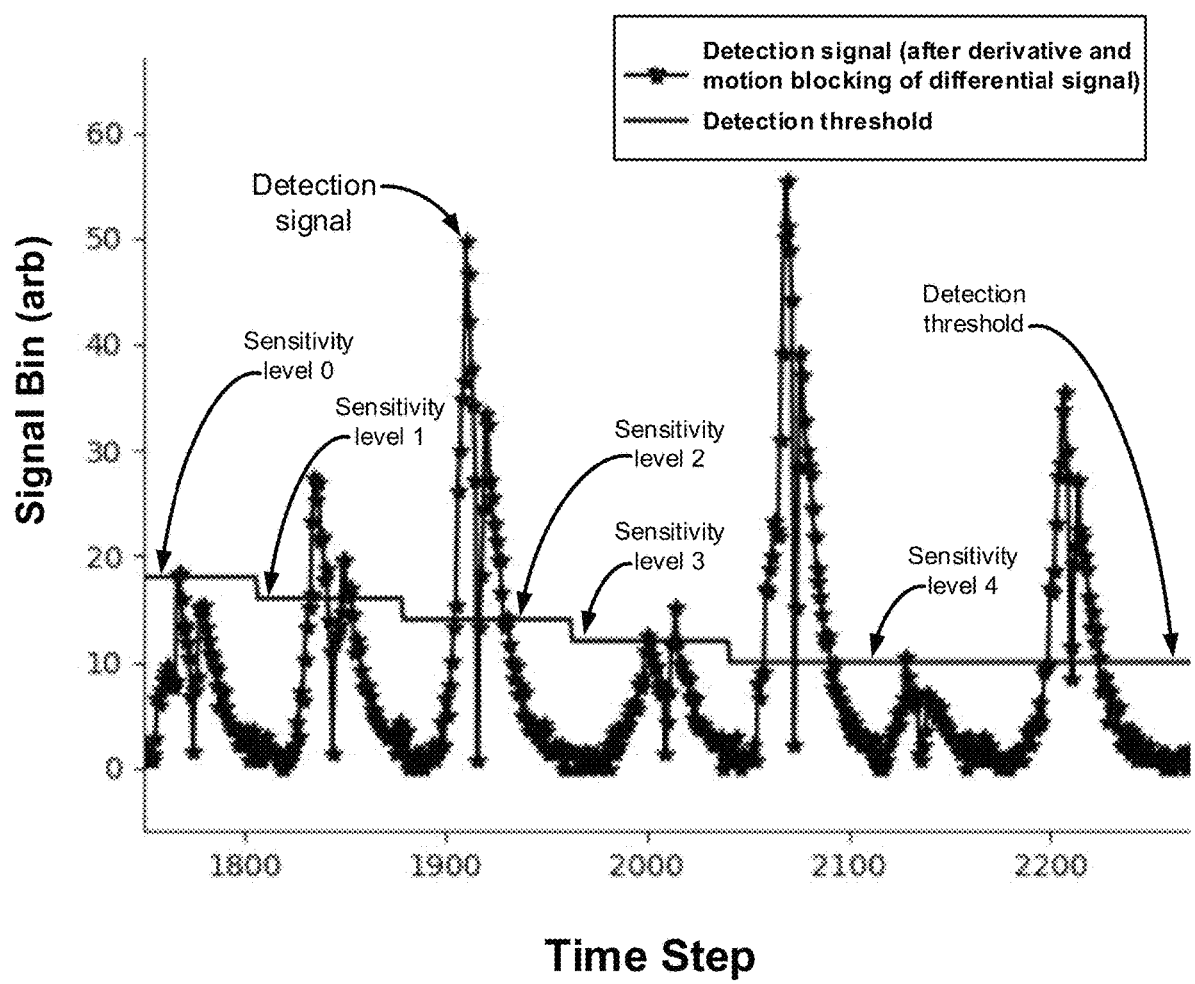
FIG. 14 is a signal diagram illustrating a test rod being extended and a sensitivity level of the metal detection device being adjusted.

FIG. 14 is a signal diagram illustrating an operator (e.g., a surgeon or other medical professional) adjusting the sensitivity level of the device 100 at the same time that the operator is also sliding the test rod slider 117 forward to test the functionality of the device using the test rod 133. The device 100 can be operating in a low speed and low sensitivity mode in the scenario shown in FIG. 14 (e.g., a sensitivity level of 7 or below). In this mode, the one or more processors of the microcontroller 185 can be programmed to execute instructions to apply a derivative and apply a motion blocking algorithm to the differential signal to obtain the detection signal. The motion blocking algorithm or motion blocker signal will be discussed in more detail in the following sections (see, e.g., FIGS. 17A and 17B). Moreover, each time step in FIG. 14 can represent approximately 28 milliseconds.

FIG. 14 illustrates that the operator can raise the sensitivity level (i.e., lower the sensitivity threshold) by dialing the sensitivity wheel(s) 115 forward or distally. The operator can raise the sensitivity level (for example, from level 0 to level 4) to ensure that the test rod 133 is sensed by the distal sensing portion 136.

Each spike in the detection signal can represent an instance where a distal segment of the test rod 133 is extended out of the spring tube 137 and into the sensor housing 141 in proximity to the magnetometers. The larger spikes can be instances in which the test rod 133 is extended further into the sensor housing 141 in close proximity to the magnetometers. The smaller spikes can be instances in which the distal segment of the test rod 133 is extended only slightly into the sensor housing 141 or being retracted back into the spring tube 137.

Figure 15:
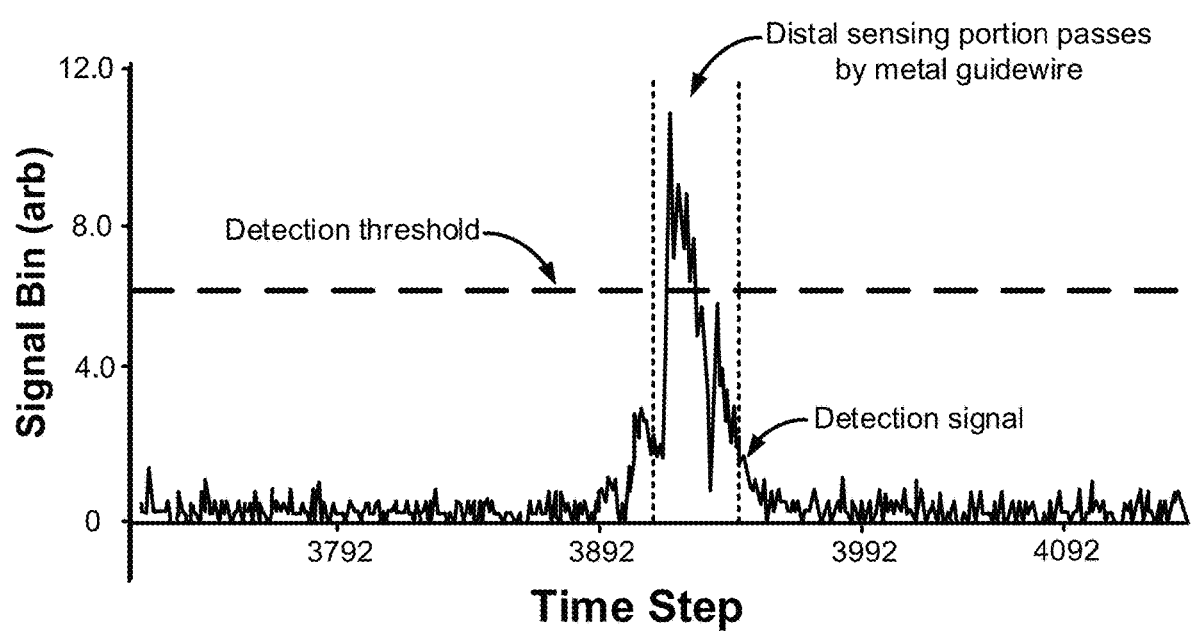
FIG. 15 is a signal diagram illustrating a distal sensing portion of the metal detection device passing over part of a metal guidewire.

FIG. 15 is a signal diagram illustrating the distal sensing portion 136 passing over part of a metal guidewire. For example, the guidewire can be a straight fixed core guidewire made in part of stainless steel. As shown in FIG. 15, the detection signal can exceed a sensitivity threshold or detection threshold when the distal sensing portion 136 passes over part of the metal guidewire. In this example, the distal sensing portion 136 is within 10 mm of the metal guidewire when the distal sensing portion 136 passes over the metal guidewire.

The output component (e.g., the speaker 181, the proximal LED 173, the distal LED 183, or a combination thereof) can generate a user output (e.g., a beeping sound, a flashing light or a brighter light, or a combination thereof) to alert a user that the distal sensing portion 136 has passed over the metal guidewire.

The device 100 can be operating in a low speed and low sensitivity mode in the scenario shown in FIG. 15. In this mode, the sensitivity wheel(s) 115 can be dialed backward or proximally such that the sensitivity level is below a starting default level (e.g., level 7 or below). Also, in this mode, the one or more processors of the microcontroller 185 can be programmed to execute instructions to apply a derivative to the differential signal to obtain the detection signal. Moreover, each time step in FIG. 15 can represent approximately 28 milliseconds.

Figure 16A:
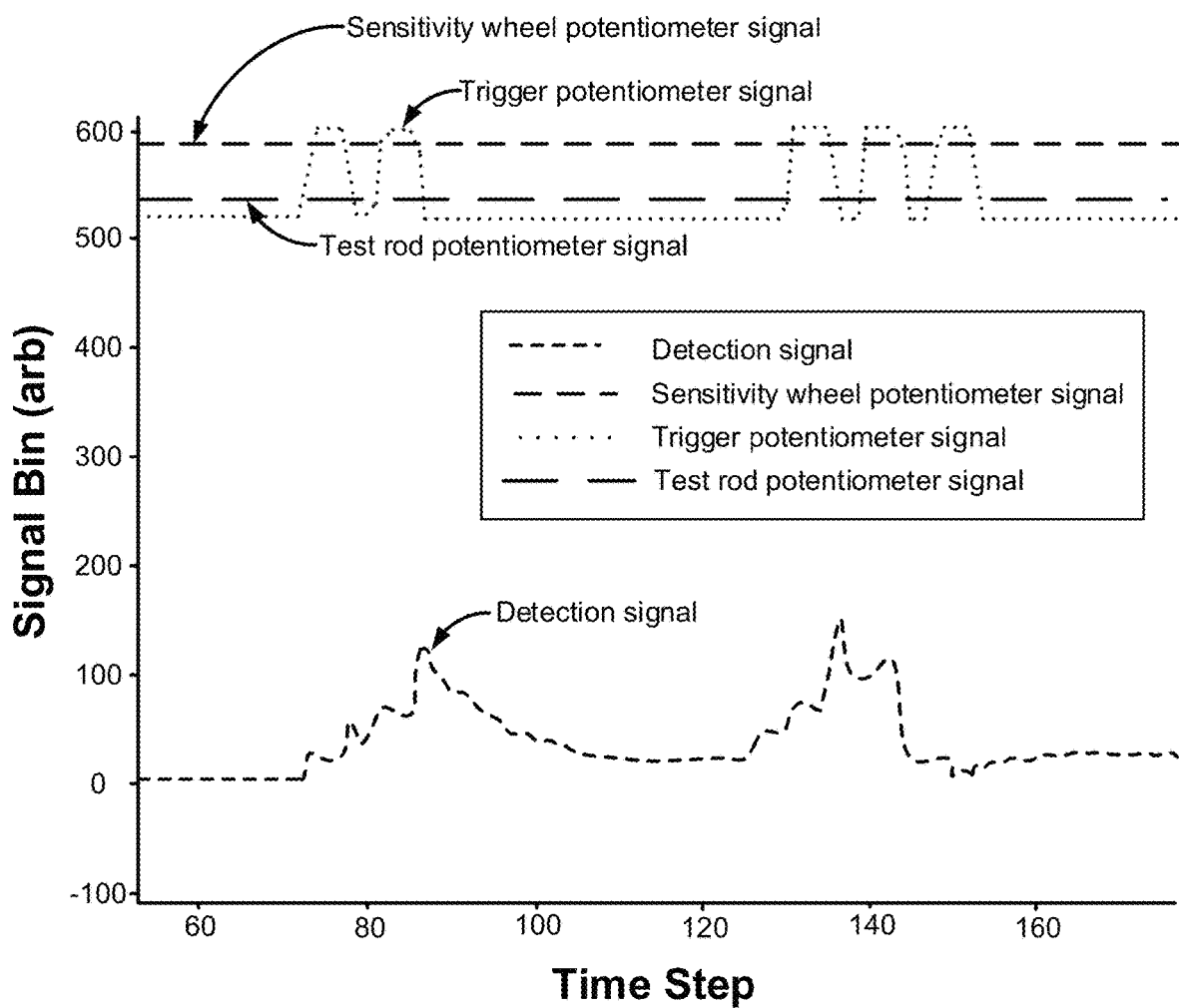
FIG. 16A is a signal diagram illustrating the effects on a detection signal as the trigger of the metal detection device is pulled.

FIG. 16A is a signal diagram illustrating the effects on the detection signal as the trigger 105 is pulled. As shown in FIG. 16A, the trigger 105 is squeezed twice in succession and then squeezed three additional times in succession after a brief period where the trigger 105 is not actuated. Each time the trigger 105 is squeezed, a spike in the trigger potentiometer signal is observed. As seen in FIG. 16A, the sensitivity wheel(s) 115 and the test rod slider 117 are not actuated during this period as evidenced by the flat sensitivity wheel potentiometer signal and the test rod potentiometer signal, respectively.

The device 100 can be operating in a low speed and low sensitivity mode in the scenario shown in FIG. 16A. In this mode, the sensitivity wheel(s) 115 can be dialed backward or proximally such that the sensitivity level is below a starting default level (e.g., level 7 or below). Also, in this mode, the one or more processors of the microcontroller 185 can be programmed to execute instructions to apply a derivative to the differential signal to obtain the detection signal. Moreover, each time step in FIG. 16A can represent approximately 28 milliseconds.

FIG. 16A shows that the detection signal jump or spikes each time the trigger 105 is squeezed, even when no RSIs or other ferromagnetic sharps are detected. The detection signal can jump or spike as a result of the distal sensing portion 136 moving in response to the flexible portion 145 bending or curling from the trigger pull.

Figure 16B:
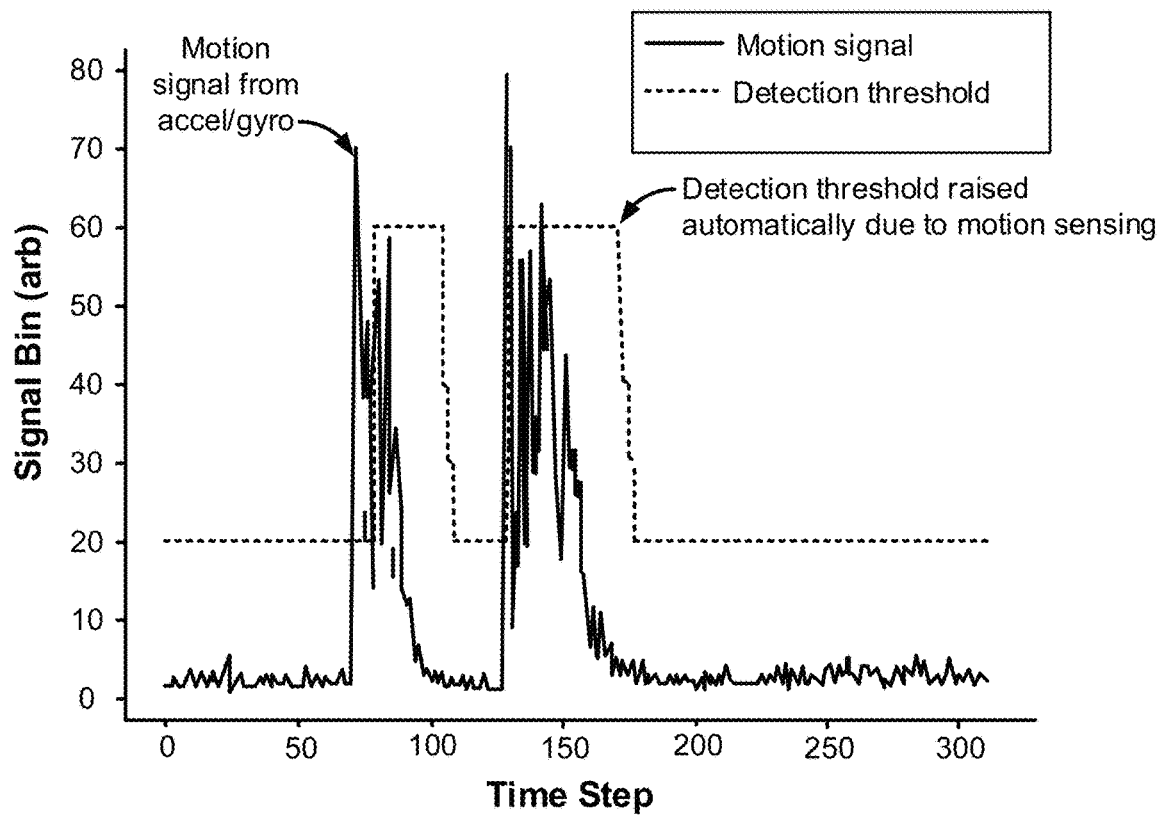
FIG. 16B is a signal diagram illustrating the metal detection device automatically raising a sensitivity threshold or detection threshold in response to the trigger pulling scenario shown in FIG. 16A.

FIG. 16B is a signal diagram illustrating the device 100 automatically raising the sensitivity threshold or detection threshold in response to the trigger pulling scenario shown in FIG. 16A. For example, the one or more processors of the microcontroller 185 can be programmed to execute instructions to observe a motion signal from the accelerometer and gyroscope of the IMU 159 disposed in the distal sensing portion 136. When the motion signal exceeds a preset or predetermined motion threshold, the one or more processors of the microcontroller 185 can be programmed to execute further instructions to automatically raise the sensitivity threshold or detection threshold such that the sensitivity level or detection sensitivity of the device 100 is lowered. As shown in FIG. 16B, the sensitivity or detection threshold is raised during the two instances (the two trigger pulls and the three trigger pulls) when the trigger 105 is pulled in succession.

Figure 16C:
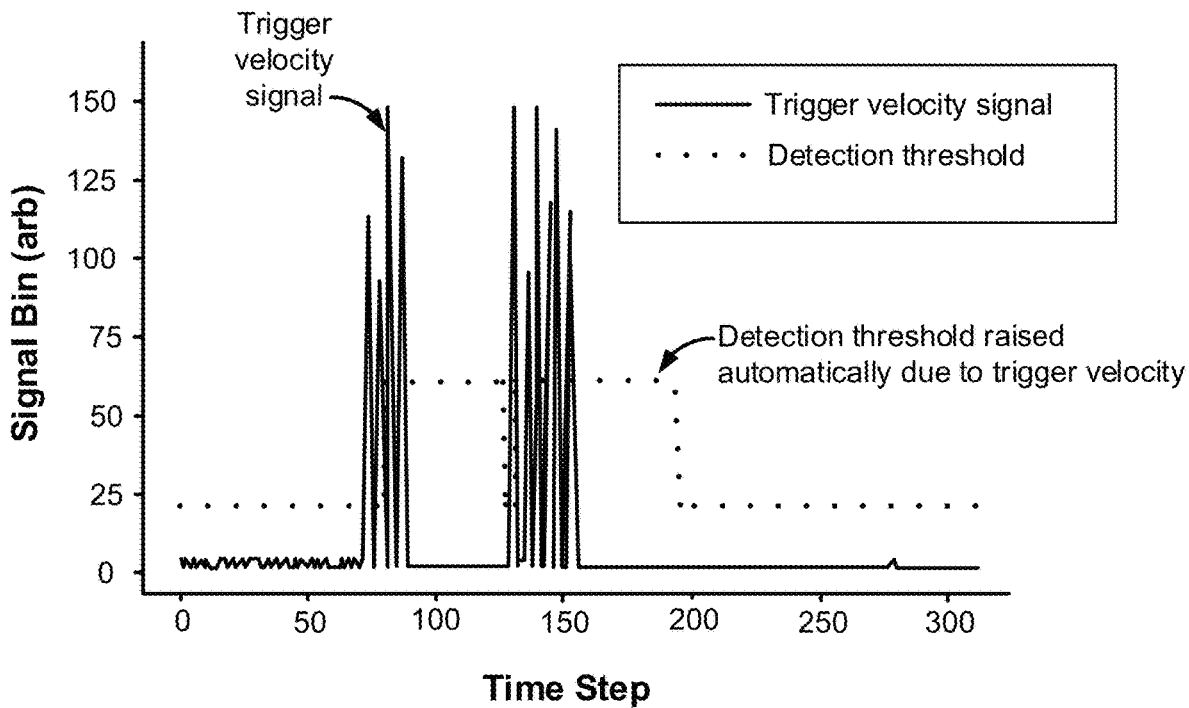
FIG. 16C is another signal diagram illustrating the metal detection device automatically raising the sensitivity threshold or detection threshold in response to the trigger pulling scenario shown in FIG. 16A.

FIG. 16C is another signal diagram illustrating the device 100 automatically raising the sensitivity threshold or detection threshold in response to the trigger pulling scenario shown in FIG. 16A. the one or more processors of the microcontroller 185 can be programmed to execute instructions to observe a trigger velocity signal from the trigger potentiometer 171 indicative of a trigger speed. When the trigger velocity signal exceeds a preset or predetermined velocity threshold (e.g., when the trigger 105 is pulled too fast), the one or more processors of the microcontroller 185 can be programmed to execute further instructions to automatically raise the sensitivity threshold or detection threshold such that the sensitivity level or detection sensitivity of the device 100 is lowered. As shown in FIG. 16C, the sensitivity or detection threshold is raised during the two instances when the trigger 105 is pulled in succession.

Figure 17A:
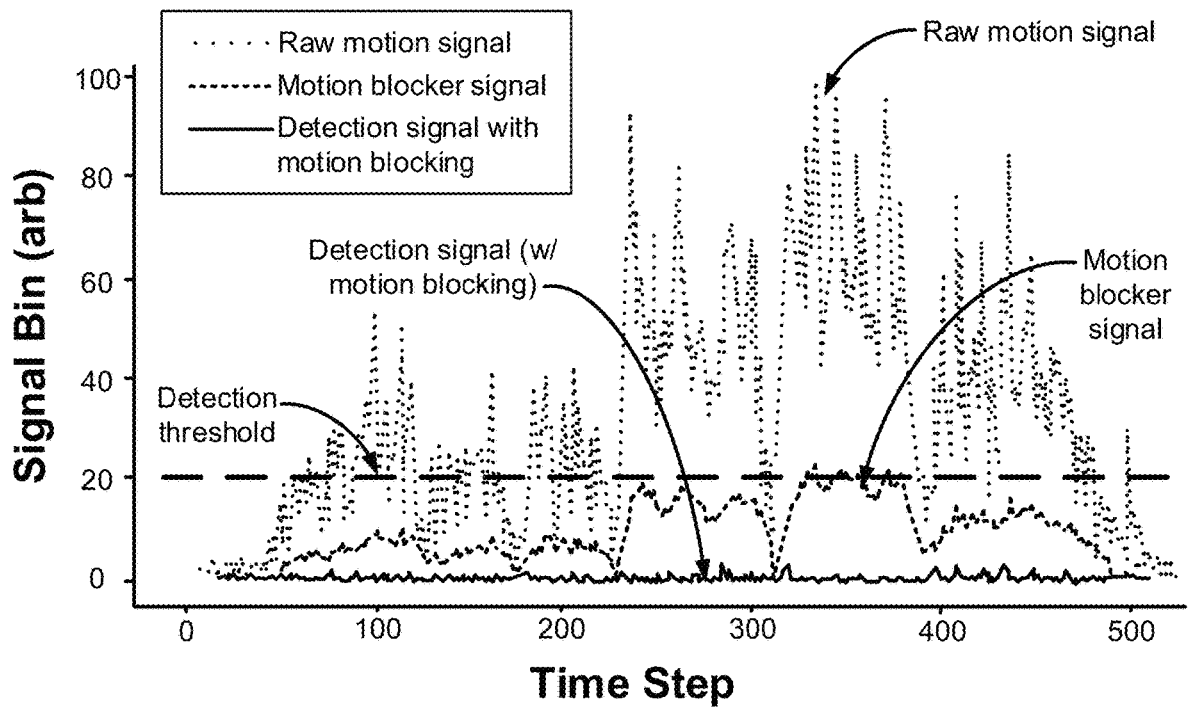
FIGS. 17A and 17B are signal diagrams illustrating a motion blocking or blocker signal used to scale down the detection signal in the event a distal sensing portion of the metal detection device is subjected to sudden motions.
Figure 17B:
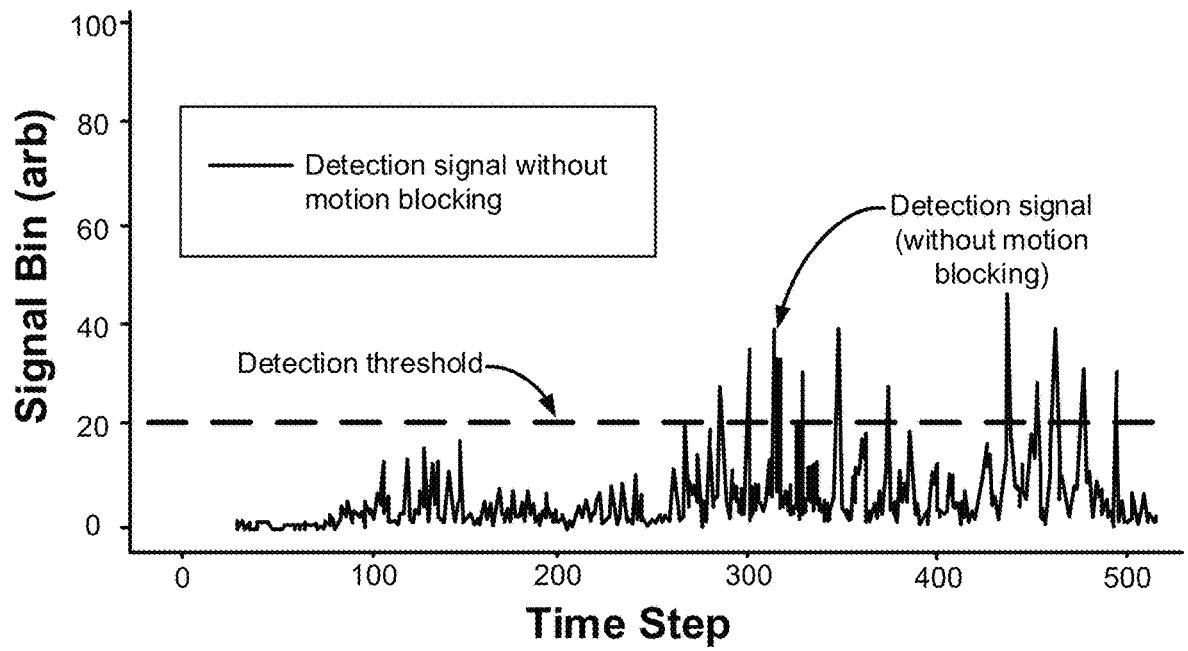

FIGS. 17A and 17B are signal diagrams illustrating a motion blocking or blocker signal used to scale down the detection signal in the event the distal sensing portion 136 is subjected to sudden motions. The device 100 can be operating in a low speed and low sensitivity mode in the scenarios shown in FIGS. 17A and 17B. In this mode, the sensitivity wheel(s) 115 can be dialed backward or proximally such that the sensitivity level is below a starting default level (e.g., level 7 or below). Also, in this mode, the one or more processors can be programmed to execute instructions to apply a derivative to the differential signal to obtain the detection signal. Moreover, each time step in FIGS. 17A and 17B can represent approximately 28 milliseconds.

FIG. 17A illustrates a raw motion signal calculated from data received from the accelerometer and gyroscope of the IMU 159. The device 100 can use the raw motion signal to calculate a motion blocker signal to scale down the detection signal. For example, the one or more processors of the microcontroller 185 can be programmed to execute instructions to calculate the motion blocker signal by comparing the raw motion signal against a motion threshold. For example, the motion blocker signal can be 1 when the raw motion signal falls below the motion threshold. However, the motion blocker signal can be raised based on the size of the raw motion signal. The size of the motion blocker signal can substantially track the size of the raw motion signal when the raw motion signal exceeds the motion threshold. The one or more processors of the microcontroller 185 can be programmed to execute further instructions to divide a detection signal by the motion blocker signal to obtain a more motion-resistant detection signal. FIG. 17A illustrates the detection signal after undergoing motion blocking. An example detection threshold is also provided in FIG. 17A to illustrate how the detection signal (with motion blocking) remains below the detection threshold, thereby preventing false positive detections.

FIG. 17B illustrates the detection signal without having undergone the aforementioned motion blocking steps. As shown in FIG. 17B, the detection signal (without motion blocking) exceeds the same detection threshold shown in FIG. 17A on multiple occasions, thereby increasing the likelihood of numerous false positive detections.

Figure 18:
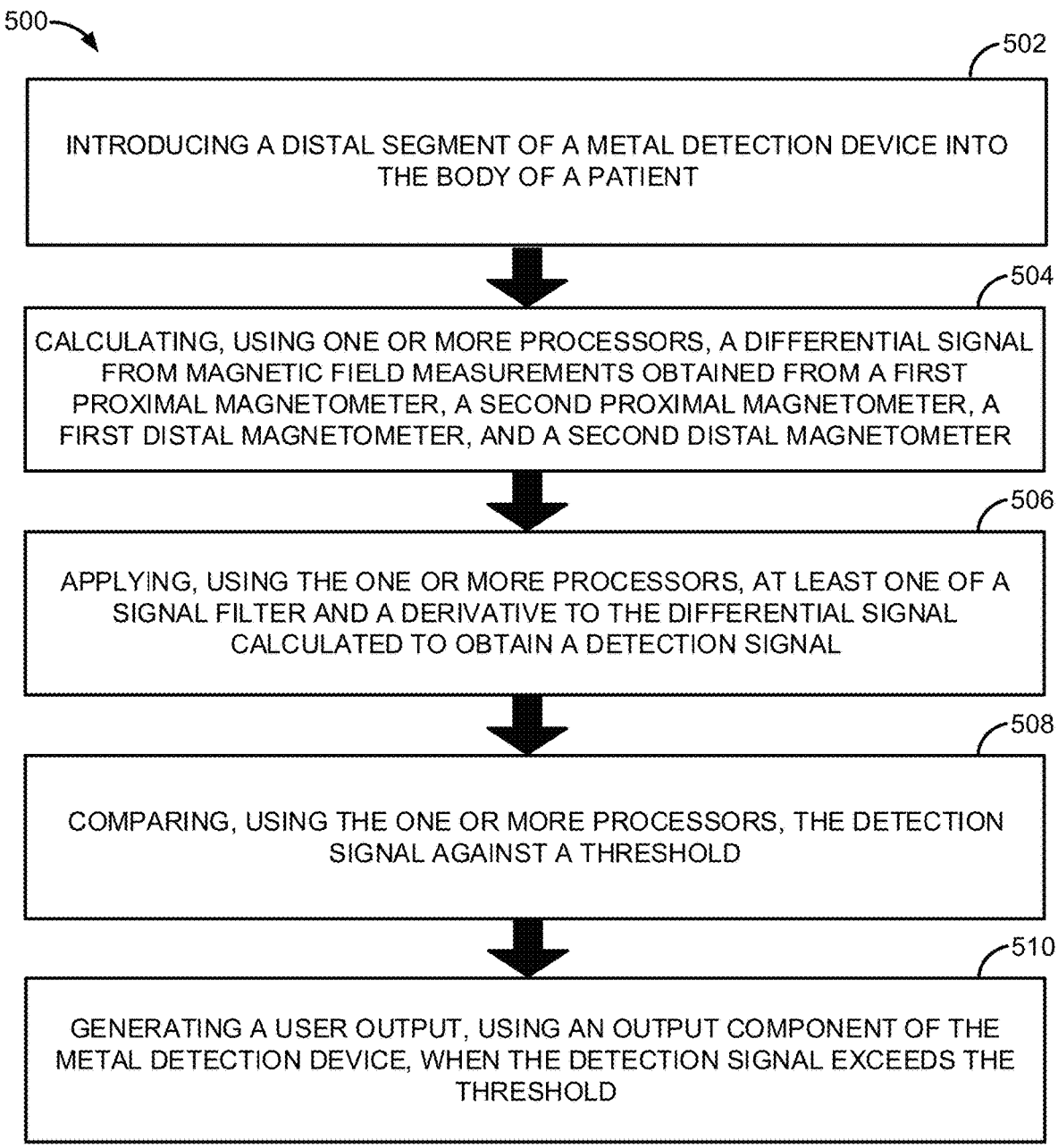
FIG. 18 illustrates a method of detecting a magnetic object within the body of a patient.

FIG. 18 illustrates a method 500 of detecting a magnetic object within the body of a patient. The method 500 comprises introducing a part of the metal detection device 100 into the body of the patient in step 502. The metal detection device 100 can comprise a handle 102, a shaft 131 extending from the handle 102, and a microcontroller 185 comprising one or more processors and memory units, an output component, and a distal sensing portion 136 positioned distally of the shaft 131. The distal sensing portion 136 can comprise a proximal gradiometer 200 comprising a first proximal magnetometer 202 and a second proximal magnetometer 204 and a distal gradiometer 206 comprising a first distal magnetometer 208 and a second distal magnetometer 210.

The method 500 can also comprise calculating, using the one or more processors, a differential signal from magnetic field measurements obtained from the first proximal magnetometer 202, the second proximal magnetometer 204, the first distal magnetometer 208, and the second distal magnetometer 210 in step 504.

The method 500 can also comprise applying, using the one or more processors, at least one of a signal filter and a derivative to the differential signal calculated to obtain a detection signal in step 506. The method 500 can further comprise comparing, using the one or more processors, the detection signal against a sensitivity threshold or detection threshold in step 508. The method 500 can also comprise generating a user output, using the output component, when the detection signal exceeds the sensitivity or detection threshold in step 510. The detection signal can exceed the sensitivity or detection threshold when the distal sensing portion 136 passes by or passes over a ferromagnetic RSI or another ferromagnetic object.

Figure 19:
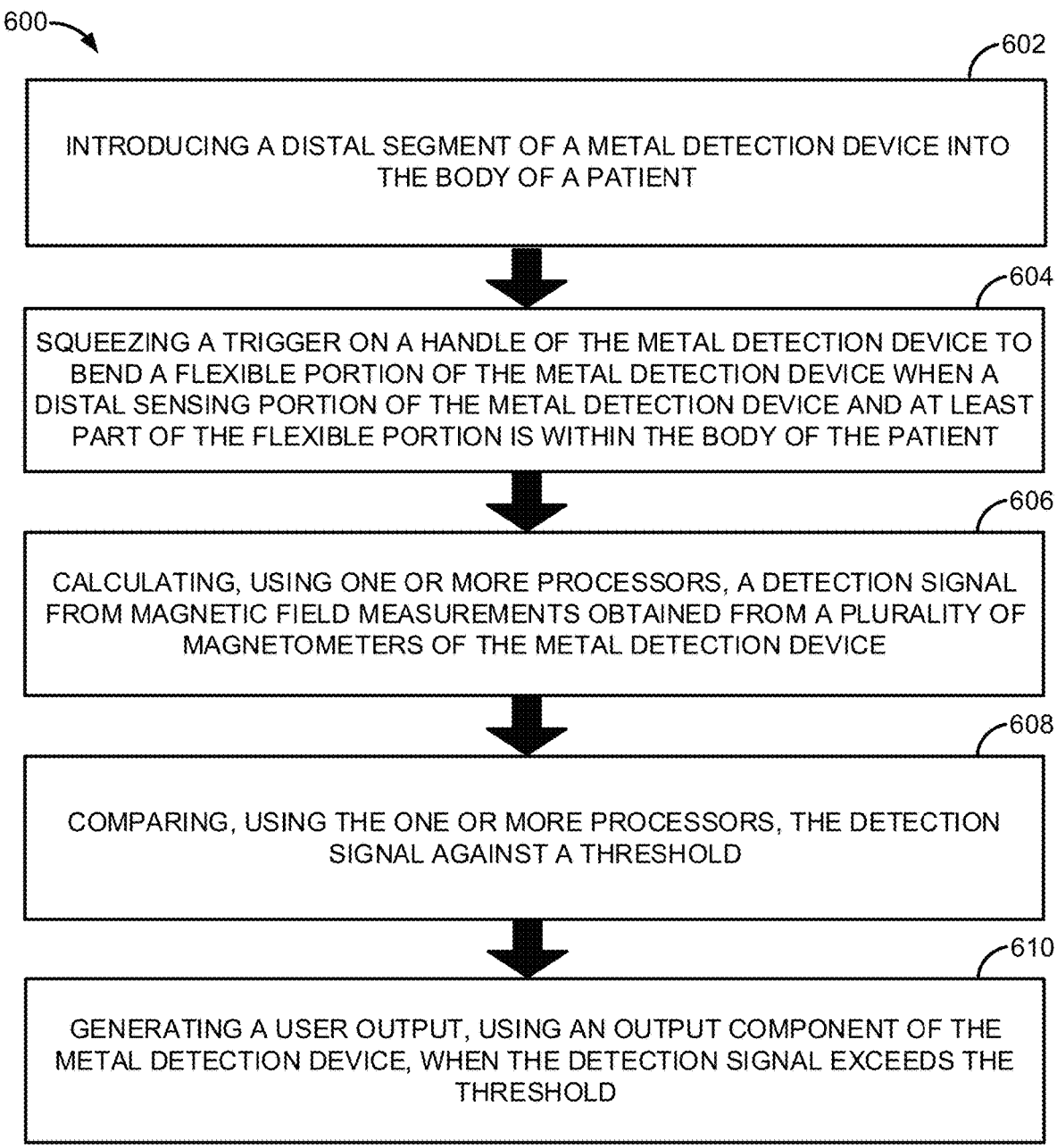
FIG. 19 illustrates another method of detecting a magnetic object within the body of a patient.

FIG. 19 illustrates another method 600 of detecting a magnetic object within a body of a patient. The method 600 can comprise introducing a part of a metal detection device 100 (e.g., the distal segment of the metal detection device 100) into the body of the patient in step 602. The metal detection device 100 can comprise a handle 102, a shaft 131 extending from the handle 102, a distal sensing portion 136 positioned distally of the shaft 131, a flexible portion 145 connecting the shaft 131 to the distal sensing portion 136, and a microcontroller 185 comprising one or more processors and memory units, and an output component.

The distal sensing portion 136 can comprise a plurality of magnetometers. For example, the distal sensing portion 136 can comprise a proximal gradiometer 200 comprising a first proximal magnetometer 202 and a second proximal magnetometer 204 and a distal gradiometer 206 comprising a first distal magnetometer 208 and a second distal magnetometer 210.

The method 600 can also comprise squeezing a trigger 105 on the handle 102 to bend the flexible portion 145 when the distal sensing portion 136 and at least part of the flexible portion 145 is within the body of the patient in step 604. The method 600 can further comprise calculating, using the one or more processors, a detection signal from magnetic field measurements obtained from the plurality of magnetometers in step 606. Calculating the detection signal can further comprise calculating, using the one or more processors, a differential signal from magnetic field measurements obtained from the first proximal magnetometer, the second proximal magnetometer, the first distal magnetometer, and the second distal magnetometer. Moreover, the method 600 can also comprise applying at least one of a signal filter and a derivative to the differential signal calculated to obtain the detection signal.

The method 600 can further comprise comparing, using the one or more processors, the detection signal against a sensitivity threshold or detection threshold in step 608. The method 600 can also comprise generating a user output, using the output component, when the detection signal exceeds the sensitivity threshold or detection threshold in step 610. The detection signal can exceed the sensitivity or detection threshold when the distal sensing portion 136 passes by or passes over a ferromagnetic RSI or another ferromagnetic object.

The method 600 can also comprise determining a trigger speed based on data obtained from a trigger potentiometer 171 within the handle 102. The trigger potentiometer 171 can be coupled to the trigger 105. The method 600 can further comprise adjusting, using the one or more processors, the sensitivity or detection threshold based on the trigger speed.

Figure 20:
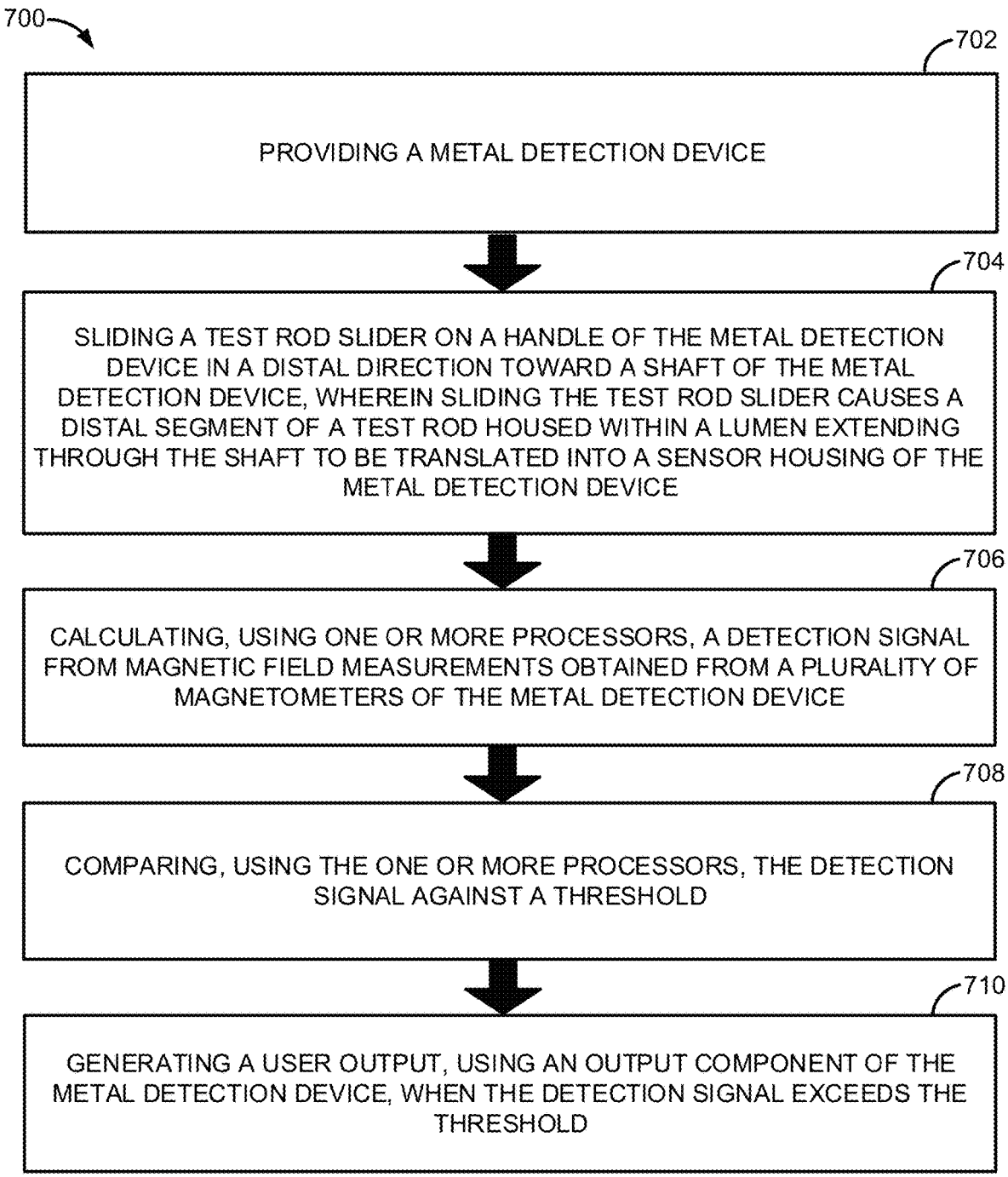
FIG. 20 illustrates a method of testing a functionality of a metal detection device.

FIG. 20 illustrates a method 700 of testing a functionality of a metal detection device 100. The method 700 can comprise providing a metal detection device 100 in step 702. The metal detection device 100 can comprise a handle 102, a shaft 131 extending from the handle 102, a distal sensing portion 136 positioned distally of the shaft 131, a flexible portion 145 connecting the shaft 131 to the distal sensing portion 136, and a microcontroller 185 comprising one or more processors and memory units, and an output component.

The distal sensing portion 136 can comprise a plurality of magnetometers. For example, the distal sensing portion 136 can comprise a proximal gradiometer 200 comprising a first proximal magnetometer 202 and a second proximal magnetometer 204 and a distal gradiometer 206 comprising a first distal magnetometer 208 and a second distal magnetometer 210.

The method 700 can also comprise sliding a test rod slider 117 on the handle 102 in a distal direction toward the shaft 131. Sliding the test rod slider 117 causes a distal segment of a test rod 133 housed within a lumen extending through the shaft 131 to be translated into the sensor housing 141 in step 704.

The method 700 can also comprise calculating, using the one or more processors, a detection signal from magnetic field measurements obtained from the plurality of magnetometers when the distal segment of the test rod 133 is translated into the sensor housing 141 in step 706. The method 700 can further comprise comparing, using the one or more processors, the detection signal against a sensitivity threshold or detection threshold in step 708. The method 700 can also comprise generating a user output, using the output component, when the detection signal exceeds the sensitivity threshold in step 710.

Each of the individual variations or embodiments described and illustrated herein has discrete components and features which may be readily separated from or combined with the features of any of the other variations or embodiments. Modifications may be made to adapt a particular situation, material, composition of matter, process, process act(s) or step(s) to the objective(s), spirit or scope of the present invention.

Methods recited herein may be carried out in any order of the recited events that is logically possible, as well as the recited order of events. Moreover, additional steps or operations may be provided or steps or operations may be eliminated to achieve the desired result.

Furthermore, where a range of values is provided, every intervening value between the upper and lower limit of that range and any other stated or intervening value in that stated range is encompassed within the invention. Also, any optional feature of the inventive variations described may be set forth and claimed independently, or in combination with any one or more of the features described herein. For example, a description of a range from 1 to 5 should be considered to have disclosed subranges such as from 1 to 3, from 1 to 4, from 2 to 4, from 2 to 5, from 3 to 5, etc. as well as individual numbers within that range, for example 1.5, 2.5, etc. and any whole or partial increments therebetween.

All existing subject matter mentioned herein (e.g., publications, patents, patent applications) is incorporated by reference herein in its entirety except insofar as the subject matter may conflict with that of the present invention (in which case what is present herein shall prevail). The referenced items are provided solely for their disclosure prior to the filing date of the present application. Nothing herein is to be construed as an admission that the present invention is not entitled to antedate such material by virtue of prior invention.

Reference to a singular item, includes the possibility that there are plural of the same items present. More specifically, as used herein and in the appended claims, the singular forms "a," "an," "said" and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Unless defined otherwise, all technical and scientific terms used herein have the same meaning as commonly understood by one of ordinary skill in the art to which this invention belongs.

In understanding the scope of the present disclosure, the term "comprising" and its derivatives, as used herein, are intended to be open-ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. Also, the terms "part," "section," "portion," "member" "element," or "component" when used in the singular can have the dual meaning of a single part or a plurality of parts. As used herein, the following directional terms "forward, rearward, above, downward, vertical, horizontal, below, transverse, laterally, and vertically" as well as any other similar directional terms refer to those positions of a device or piece of equipment or those directions of the device or piece of equipment being translated or moved. Finally, terms of degree such as "substantially", "about" and "approximately" as used herein mean a reasonable amount of deviation (e.g., a deviation of up to ±0.1%, ±1%, ±5%, or ±10%, as such variations are appropriate) from the specified value such that the end result is not significantly or materially changed.

This disclosure is not intended to be limited to the scope of the particular forms set forth, but is intended to cover alternatives, modifications, and equivalents of the variations or embodiments described herein. Further, the scope of the disclosure fully encompasses other variations or embodiments that may become obvious to those skilled in the art in view of this disclosure.

We claim:

1. A metal detection device, comprising:
a handle;
a shaft extending from the handle;
a distal sensing portion positioned distally of the shaft, wherein the distal sensing portion comprises one or more magnetometers, wherein each of the one or more magnetometers comprises one or more axes;
an output component configured to generate a user output to alert a user of a detected object;
a microcontroller comprising one or more processors and memory units, wherein the one or more processors are programmed to execute instructions stored in the memory units to:
calculate a detection signal from magnetic field measurements obtained from the one or more magnetometers,
compare the detection signal against a threshold, and
instruct the output component to generate the user output when the detection signal exceeds the threshold;
a flexible tubing coupling the distal sensing portion to the shaft, wherein the flexible tubing is bendable and comprises a straightened configuration and a bent configuration;
wherein the handle further comprises:
a trigger configured to control bending of the flexible tubing, wherein the trigger is connected to the flexible tubing by a pull cable extending through the shaft and the flexible tubing, wherein squeezing the trigger pulls the pull cable to bend the flexible tubing,
a clocking ring coupled to the shaft, wherein the shaft is rotatable with respect to a longitudinal axis of the shaft in response to a rotation of the clocking ring, and
a locking ring, wherein the locking ring comprises a plurality of locking splines configured to obstruct the clocking ring from rotating, wherein the clocking ring is configured to be pushed in a distal direction to free the clocking ring from the locking splines of the locking ring, and wherein the clocking ring is rotatable after being pushed in the distal direction; and
a test rod configured to translate into and retract out of a sensor housing covering the distal sensing portion to verify a functionality of the metal detection device, wherein the one or more processors are configured to execute instructions to adjust the threshold according to a location of the test rod.

2. The metal detection device of claim 1, wherein the test rod comprises a ferromagnetic material.

3. The metal detection device of claim 1, wherein one or more processors can be configured to compare magnetic field measurements obtained from the one or more magnetometers with magnetic field measurements associated with the test rod.

* * * * *